US007393852B2

(12) United States Patent
Chen et al.

(10) Patent No.: US 7,393,852 B2
(45) Date of Patent: Jul. 1, 2008

(54) PIPERAZINE DERIVATIVES AND METHODS OF USE

(75) Inventors: Jian J. Chen, Newbury Park, CA (US); Ben C. Askew, Newbury Park, CA (US); Kaustav Biswas, Calabasas, CA (US); Jennifer N. Chau, Santa Ana, CA (US); Derin C. D'Amico, Newbury Park, CA (US); Scott Harried, Woodland Hills, CA (US); Thomas Nguyen, Thousand Oaks, CA (US); Wenyuan Qian, Camarillo, CA (US); Jiawang Zhu, Simi Valley, CA (US); Christopher H. Fotsch, Thousand Oaks, CA (US); Aiwen Li, Westlake Village, CA (US); Qingyian Liu, Camarillo, CA (US); Nobuku Nishimura, West Hills, CA (US); Tanya Peterkin, Woodland Hills, CA (US); Babak Riahi, Woodland Hills, CA (US); Chester Chenguang Yuan, Newbury Park, CA (US); Nianhe Han, Thousand Oaks, CA (US); Rana Nomak, Westlake Village, CA (US); Kevin Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 492 days.

(21) Appl. No.: 10/874,086

(22) Filed: Jun. 21, 2004

(65) Prior Publication Data

US 2005/0014749 A1 Jan. 20, 2005

Related U.S. Application Data

(60) Provisional application No. 60/480,303, filed on Jun. 20, 2003.

(51) Int. Cl.
*A61K 31/54* (2006.01)
*A61K 31/4965* (2006.01)
*C07D 241/04* (2006.01)
*C07D 265/30* (2006.01)
*C07D 279/12* (2006.01)

(52) U.S. Cl. ............................. 514/255.01; 514/227.5; 514/237.5; 544/59; 544/158; 544/384

(58) Field of Classification Search .............. 514/227.5, 514/237.5, 255.01; 544/59, 158, 384
See application file for complete search history.

(56) References Cited

U.S. PATENT DOCUMENTS

| 2005/0124654 | A1 | 6/2005 | Groneberg et al. |
| 2005/0234044 | A1 | 10/2005 | Groneberg et al. |
| 2006/0025400 | A1* | 2/2006 | Askew et al. ............ 514/210.2 |

FOREIGN PATENT DOCUMENTS

| EP | 0 641 779 | | 8/1994 |
| EP | 1 106 615 | A1 | 6/2001 |
| WO | WO 92/12140 | | 7/1992 |
| WO | WO 02/06222 | A1 | 1/2002 |
| WO | WO 02/099388 | A2 | 12/2002 |
| WO | WO 03/007958 | | 1/2003 |
| WO | WO 03/007958 | A1 | 1/2003 |
| WO | WO 2004/033436 | | 4/2004 |
| WO | WO 2004/054584 | | 7/2004 |
| WO | WO 2004/054584 | A1 | 7/2004 |
| WO | WO 2004/083173 | | 9/2004 |
| WO | WO 2004/083173 | A3 | 9/2004 |

OTHER PUBLICATIONS

Bailey, et al., Tetrahedron Letters, *Piperzine-2,3,5-triones in the synthesis of constrained peptides*, 40, 7557-7560 (1999).
Su, et al., JACS Communications, *Discovery of a Potent, Non-Peptide Brandykinin B₁ Receptor Anatagonist*, A-B, S1-S7 (2003).
Park Choo, H.Y. et al., "Synthesis of Piperazine Derivative and Evaluation of Their Antihistamine and Antibradykinin Effects," *Bioorganic & Medicinal Chemistry Letters*, vol. 9, pp. 2727-2730, (1999).

* cited by examiner

*Primary Examiner*—Johann Richter
*Assistant Examiner*—Ebenezer Sackey
(74) *Attorney, Agent, or Firm*—Richard V. Person; Rekha P. Bansal

(57) ABSTRACT

Selected compounds are effective for treatment of pain and diseases, such as inflammation mediated diseases. The invention encompasses novel compounds, analogs, prodrugs and pharmaceutically acceptable derivatives thereof, pharmaceutical compositions and methods for prophylaxis and treatment of diseases and other maladies or conditions involving pain, inflammation, and the like. The subject invention also relates to processes for making such compounds as well as to intermediates useful in such processes.

42 Claims, No Drawings

PIPERAZINE DERIVATIVES AND METHODS OF USE

This application claims the benefit of U.S. Provisional Application No. 60/480,303, filed Jun. 20, 2003, which is hereby incorporated by reference.

FIELD OF THE INVENTION

This invention is in the field of pharmaceutical agents and specifically relates to compounds, compositions, uses and methods for treating inflammation-related disorders, including pain.

BACKGROUND OF THE INVENTION

More than two million people in the United States alone are incapacitated by chronic pain on any given day (T. Jessell & D. Kelly, Pain and Analgesia in PRINCIPLES OF NEURAL SCIENCE, third edition (E. Kandel, J. Schwartz, T. Jessell, eds., (1991)). Unfortunately, current treatments for pain are only partially effective, and many cause lifestyle altering, debilitating, and/or dangerous side effects. For example, non-steroidal anti-inflammatory drugs ("NSAIDs") such as aspirin, ibuprofen, and indomethacin are moderately effective against inflammatory pain but they are also renally toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixeletine simultaneously inhibit pain and cause loss of normal sensation. In addition, when used systemically, local anesthetics are associated with adverse cardiovascular effects. Thus, there is currently an unmet need in the treatment of chronic pain.

Pain is a perception based on signals received from the environment and transmitted and interpreted by the nervous system (for review, see M. Millan, Prog. Neurobiol. 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediate the pathophysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacological Rev, 32(1), 1-46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, J. Biol. Chem. 269, 21583-21586 (1994); Hess et al, Biochem. Biophys. Res. Commun. 184, 260-268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysio-logical responses to bradykinin are mediated by B2 receptors.

B1 receptors, on the other hand, have a higher affinity for des-Arg-BK compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (F. Marceau, et al., Immunopharmacology, 30, 1-26 (1995)). Furthermore, responses mediated by B1 receptors are up-regulated from a null level following administration of bacterial lipopolysaccharide (LPS) or inflammatory cytokines in rabbits, rats, and pigs.

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues.

Certain compounds have been described as bradykinin antagonists. WO 03/07958, published 30 Jan. 2003, describes tetrahydroquinoxalines. Dihydroquinoxalinones are described in a JACS communication.

Piperazine-2,3,5-triones are described in Tet. Lett., 40, 7557-7560 (1999). European application 641779, published 8 Mar. 1995, describes 3,6-dioxopiperazines as platelet aggregation inhibitors.

Clearly, there is a need for new, safe and effective treatments for inflammation and pain. Such agents are provided in the present invention.

DETAILED DESCRIPTION OF THE INVENTION

A class of compounds useful in treating inflammation and pain is defined by Formula I

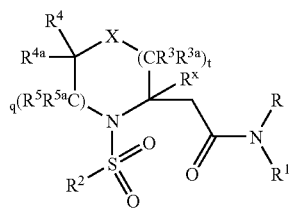

wherein q is 0-3;

wherein t is 0-2;

wherein X is selected from NH, S, O and NR$^a$; wherein R$^a$ is selected form alkyl, substituted alkyl, —C(O)R$^8$, —CO$_2$R$^8$, —C(O)NR$^8$R$^{8'}$, —SO$_2$R$^8$ and —SO$_2$NR$^8$R$^{8'}$; provided R$^3$ and R$^{3a}$ or R$^4$ and R$^{4a}$ together do not form oxo if R$^a$ is —C(O)R$^8$, —CO$_2$R$^8$, —C(O)NR$^8$R$^{8'}$, —SO$_2$R$^8$ or —SO$_2$NR$^8$R$^{8'}$;

wherein R is selected from a) 9-11 membered fused bicyclic carbocyclic or heterocyclic ring substituted with one to three basic moieties, and optionally substituted with one to three groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, b) 4-7 membered carbocyclic ring substituted with one to three basic moieties, and optionally substituted with one to three groups independently selected from halo, hydroxyl, cyano, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, c) 4-7 membered heterocyclic ring substituted with one to three basic moieties, and optionally substituted with one to three groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, d) arylalkyl substituted with one to three basic moieties, and optionally substituted with one to three groups independently selected from halo, hydroxyl, cyano, (C$_1$-C$_6$) alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$) alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, e) 5-6 membered heterocyclylalkyl substituted with one to three basic moieties, and optionally substituted with one to three groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, f) 5-7 membered cycloalkyl, g) 4-7 membered carbocyclic or heterocyclic ring optionally substituted with one to three groups independently selected from halo, hydroxyl, cyano, oxo, (C$_1$-C$_6$) alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$) alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, h) diphenylmethyl, and i) 9-11 membered fused bicyclic carbocyclic or heterocyclic ring optionally substituted with one to three groups independently selected from halo, cyano, oxo, (C$_1$-C$_6$) alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$) alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein R$^1$ is selected from H, C$_{1-4}$-alkyl, substituted C$_{1-4}$-alkyl, aryl and substituted aryl;

alternatively R and R$^1$ together with the nitrogen atom to which they are attached form a 5-8 membered heterocyclyl ring, optionally containing 1-2 additional heteroatoms, fused to a phenyl group, further substituted with a basic moiety;

wherein R$^2$ is selected from arylalkenyl, aryl, and heterocyclyl selected from thienyl, quinolinyl, isoquinolinyl, 3-pyridyl, thiazol4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein R$^2$ is optionally substituted with one to five groups independently selected from halo, —NH$_2$, hydroxyl, cyano, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$) alkylamino, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein R$^3$, R$^{3a}$, R$^4$, R$^{4a}$, R$^5$ and R$^{5a}$ are independently selected from H, C$_{1-3}$ alkyl and substituted C$_{1-3}$ alkyl;

or wherein R$^3$ and R$^{3a}$ together form oxo, or R$^4$ and R$^{4a}$ together form oxo, or R$^5$ and R$^{5a}$ together form oxo;

wherein R$^8$ and R$^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein R$^x$ is selected from H, (C$_1$-C$_3$)haloalkyl, and (C$_1$-C$_3$) alkyl; and wherein each substituted alkyl, substituted aryl, heteroaryl, substituted heteroaryl, substituted cycloalkyl and substituted saturated or partially saturated heterocyclyl is substituted with one to three groups independently selected from halo, —NH$_2$, hydroxyl, cyano, (C$_1$-C$_6$)alkylamino, (C$_1$-C$_6$)haloalkyl, oxo, (C$_1$-C$_6$)alkoxy, C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and pharmaceutically acceptable derivatives thereof;

provided R is not cycloheptyl when R$^1$ is H, R$^2$ is 4-methylphenyl, R$^3$ and R$^{3a}$ together form oxo, R$^5$ and R$^{5a}$ are both H, and when R$^4$ and R$^{4a}$ are both methyl; further provided R is not cycloheptyl when R$^1$ is H, R$^2$ is 2,4,6-trimethylphenyl, R$^3$ and R$^{3a}$ together form oxo, and R$^4$, R$^{4a}$, R$^5$ and R$^{5a}$ are H; and further provided the basic substiuent is not 2-pyridyl, 3-pyridyl or 2-oxo-piperaziny-4-ylmethyl.

The invention also relates to compounds of Formula I wherein q is 1-2; and wherein t is 1. It also relates to compounds wherein q is 1, in conjunction with any of the above or below embodiments.

The invention also relates to compounds of Formula I wherein X is selected from NH and NR$^a$; and wherein R$^a$ is (C$_{1-3}$)alkyl or Boc, in conjunction with any of the above or below embodiments.

The invention also relates to compounds of Formula I wherein X is NH, in conjunction with any of the above or below embodiments.

The invention also relates to compounds of Formula I wherein R is selected from 9-11 membered fused bicyclic carbocyclic or heterocyclic ring substituted with one to two basic moieties, and optionally substituted with one to three groups independently selected from halo, hydroxyl, cyano, oxo, (C$_1$-C$_6$)alkoxy, (C$_2$-C$_6$)alkenyl, (C$_2$-C$_6$)alkynyl, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, in conjunction with any of the above or below embodiments.

The invention also relates to compounds of Formula I wherein R is a partially unsaturated carbocyclic ring, such as 1,2,3,4-tetrahydronaphthyl or indanyl, substituted with a basic moiety, optionally substituted with chloro, in conjunction with any of the above or below embodiments.

The invention also relates to compounds of Formula I wherein R is selected from 1,2,3,4-tetrahydronaphth-1-yl, 1,2,3,4-tetrahydronaphth-2-yl, indan-1-yl and indan-2-yl, substituted with a basic moiety, optionally substituted with chloro, in conjunction with any of the above or below embodiments.

The invention also relates to compounds of Formula I wherein R is partially unsaturated heterocyclyl, such as chroman and 2,2-dioxo-3,4-dihydro-1H-2,1-benzothiazinyl, substituted with a basic moiety, optionally substituted with chloro, in conjunction with any of the above or below embodiments.

The invention also relates to compounds of Formula I wherein R is chroman-4-yl, or 2,2-dioxo-3,4-dihydro-1H-2,1-benzothiazin-4-yl, substituted with a basic moiety, optionally substituted with chloro, in conjunction with any of the above or below embodiments.

The invention also relates to compounds of Formula I wherein R is selected from phenyl and 5-6 membered heteroaryl; wherein R is substituted with one to two basic moieties, and optionally substituted with one to three groups independently selected from halo, hydroxyl, cyano, oxo, (C$_1$-C$_6$)alkoxy, —C(O)R$^8$, —COOR$^8$, —C(O)NR$^8$R$^{8'}$, —NR$^8$C(O)R$^{8'}$, (C$_1$-C$_6$)alkyl, substituted C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, in conjunction with any of the above or below embodiments.

The invention also relates to compounds of Formula I wherein R is phenyl substituted with a basic moiety selected from (C$_1$-C$_6$)alkylamino(C$_1$-C$_6$)alkyl, C$_{1-4}$-alkylamino-C$_{2-6}$-alkenyl, 5-8 membered nitrogen-containing heterocyclyl-C$_{2-6}$-alkenyl, and heterocyclyl-(C$_1$-C$_6$)alkylamino(C$_2$-C$_6$)alkyl, in conjunction with any of the above or below embodiments.

The invention also relates to compounds of Formula I wherein R is selected from 3-((piperidin-1-ylethyl) aminomethyl)phenyl and 4-imidazolin-2-ylphenyl, in conjunction with any of the above or below embodiments.

The invention also relates to compounds of Formula I wherein R is phenyl-(C$_{1-3}$)-alkyl substituted with a basic moiety, such as 4-(imidazolin-2-yl)phenylmethyl, 4-(imidazolin-2-yl)phenylethyl and 4-(imidazolin-2-yl)phenylpropyl, in conjunction with any of the above or below embodiments.

The invention also relates to compounds of Formula I wherein R$^1$ is H or methyl, in conjunction with any of the above or below embodiments.

The invention also relates to compounds of Formula I wherein R$^2$ is selected from phenyl-(C$_{2-4}$)-alkenyl, phenyl, naphthyl, 5-membered nitrogen containing heteroaryl, 5-membered sullfur containing heteroaryl, 6-membered nitrogen containing heteroaryl, 9-membered heterocyclyl, and 10-membered heterocyclyl; in conjunction with any of the above or below embodiments.

The invention also relates to compounds of Formula I wherein R$^2$ is selected from phenyl-CH═CH—, tetrahydronaphthyl, naphtho[2.3-d]dioxolyl, benzofuranyl, benzoxadiazolyl, benzothiadiazolyl, benzothiazolyl, 2-thienyl, isoxazolthienyl, benzothienyl, thieno[3,2-c]pyridinyl, naphthyl, phenyl, 3-pyridinyl, tetrahydroisoquinolinyl, quinolinyl and isoquinolinyl; wherein R$^2$ is optionally substituted with one to five groups independently selected from halo, —NH$_2$, hydroxyl, cyano, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted (C$_1$-C$_6$)alkyl, substituted aryl substituted heteroaryl and substituted saturated or partially saturated heterocyclyl is optionally substituted with one to three groups independently selected from halo, —NH$_2$, hydroxyl, cyano, (C$_1$-C$_4$)alkylamino, (C$_1$-C$_4$)haloalkyl, oxo, (C$_1$-C$_4$)alkoxy, (C$_1$-C$_4$)alkoxy(C$_1$-C$_4$)alkyl, (C$_1$-C$_4$)alkyl, (C$_2$-C$_4$)alkenyl, (C$_2$-C$_4$)alkynyl, di(C$_1$-C$_4$)alkylamino, —C(O)R$^8$, —COOR$^8$, —C(O)NR$^8$R$^{8'}$, and —NR$^8$C(O)R$^{8'}$; in conjunction with any of the above or below embodiments.

The invention also relates to compounds of Formula I wherein R$^2$ is selected from phenyl-CH═CH—, tetrahydronaphthyl, 2,1,3-benzoxadiazol-4-yl, thien-2-yl, 2-naphthyl, phenyl, 3-pyridyl, 8-quinolyl and 5-isoquinolyl; and wherein R$^2$ is optionally substituted; preferably with one or two groups independently selected from methyl, chloro, methoxy, —OCF$_3$ or —CF$_3$; such as 2,4,6-trimethylphenyl, 3,4-dichlorophenyl, 3-chloro-4-methylphenyl, 4-chloro-3-methylphenyl, 3-trifluoromethylphenyl, 4-trifluoromethylphenyl, 4-trifluoromethoxyphenyl, 4-methoxyphenyl, 4-methylphenyl, 4-chlorophenyl and 4-tert-butylphenyl; in conjunction with any of the above or below embodiments.

The invention also relates to compounds of Formula I wherein the basic moieties on R are independently selected from amino, cycloalkylamino($C_1$-$C_6$)alkyl, cycloalkyl($C_1$-$C_6$)alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$)alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-($C_1$-$C_6$)alkylamino($C_2$-$C_6$)alkyl, 5-6 membered heterocyclyloxy, 4-6 membered nitrogen-containing heterocyclyl and 5-7 membered nitrogen-containing heterocyclyl-alkyl; and wherein each of said basic substituents is optionally substituted with one to three groups independently selected from halo, —$NH_2$, hydroxyl, cyano, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^8$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, $C_1$-$C_6$)alkylamino, $C_1$-$C_6$)haloalkyl, oxo, ($C_1$-$C_6$)alkoxy, ($C_1$-$C_6$)alkoxy($C_{1-6}$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^8$, in conjunction with any of the above or below embodiments.

The invention also relates to compounds of Formula I wherein the basic moieties on R are independently selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl, in conjunction with any of the above or below embodiments.

The invention also relates to compounds of Formula I wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl, in conjunction with any of the above or below embodiments.

The invention also relates to compounds of Formula I wherein $R^3$ and $R^{3a}$ together form oxo; wherein $R^4$ and $R^{4a}$ are independently selected from H and $C_{1-3}$ alkyl; and wherein $R^5$ and $R^{5a}$ are independently H, in conjunction with any of the above or below embodiments.

Alternatively, the invention also relates to compounds wherein $R^3$ and $R^{3a}$ together form oxo; wherein $R^4$ and $R^{4a}$ are independently selected from H and methyl; and wherein $R^5$ and $R^{5a}$ are independently H, in conjunction with any of the above or below embodiments.

The invention also relates to compounds wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono-alkylamino, dialkylamino, and trifluoromethyl; in conjunction with any of the above or below embodiments.

The invention also relates to compounds of Formula I $R^x$ is H, methyl or trifluoromethyl, such as H; in conjunction with any of the above or below embodiments.

The invention also relates to compounds of Formula II

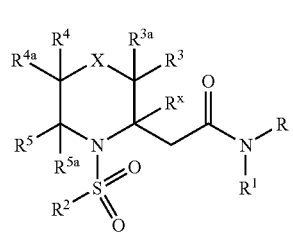

II wherein X is selected from NH, S, O and $NR^a$;
wherein $R^a$ is selected form alkyl, substituted alkyl, —C(O)$R^8$, —$CO_2R^8$, —C(O)N$R^8R^{8'}$, —$SO_2R^8$ and —$SO_2NR^8R^{8'}$; provided $R^3$ and $R^{3a}$ or $R^4$ and $R^{4a}$ together do not form oxo if $R^a$ is —C(O)$R^8$, —$CO_2R^8$, C(O)N$R^8R^{8'}$, —$SO_2R^8$ or —$SO_2NR^8R^{8'}$;
wherein R is selected from
a) 9-11 membered fused bicyclic carbocyclic or heterocyclic ring substituted with one to three basic moieties, and optionally substituted with one to three groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl,
b) phenyl substituted with one to three basic moieties, and optionally substituted with one to three groups independently selected from halo, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl,
  c) 5-6 membered heteroaryl substituted with one to three basic moieties, and optionally substituted with one to three groups independently selected from halo, hydroxyl, cyano, oxo, $(C_1\text{-}C_6)$alkoxy, $(C_2\text{-}C_6)$alkenyl, $(C_2\text{-}C_6)$alkynyl, —C(O)$R^8$, —COO$R^8$, —C(O)N$R^8R^{8'}$, N$R^8$C(O)$R^{8'}$, $(C_1\text{-}C_6)$alkyl, substituted $C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl,
  d) arylalkyl substituted with one to three basic moieties, and optionally substituted with one to three groups independently selected from halo, hydroxyl, cyano, oxo, $(C_1\text{-}C_6)$alkoxy, $(C_2\text{-}C_6)$alkenyl, $(C_2\text{-}C_6)$alkynyl, —C(O)$R^8$, —COO$R^8$, —C(O)N$R^8R^{8'}$, —N$R^8$C(O)$R^{8'}$, $(C_1\text{-}C_6)$alkyl, substituted $(C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, and
  e) 5-6 membered heteroarylalkyl substituted with one to three basic moieties, and optionally substituted with one to three groups independently selected from halo, hydroxyl, cyano, oxo, $(C_1\text{-}C_6)$alkoxy, $(C_2\text{-}C_6)$alkenyl, $(C_2\text{-}C_6)$alkynyl, —C(O)$R^8$, —COO$R^8$, —C(O)N$R^8R^{8'}$, —N$R^8$C(O)$R^{8'}$, $(C_1\text{-}C_6)$alkyl, substituted $C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
wherein $R^1$ is selected from H, $C_{1-4}$-alkyl, substituted $C_{1-4}$-alkyl, aryl and substituted aryl;
alternatively R and $R^1$ together with the nitrogen atom to which they are attached form a 5-8 membered heterocyclyl ring fused to a phenyl ring, optionally containing 1-2 additional heteroatoms, further substituted with a basic moiety;
wherein $R^2$ is selected from arylalkenyl, aryl, and heterocyclyl selected from thienyl, quinolinyl, isoquinolinyl, 3-pyridyl, thiazol4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —NH$_2$, hydroxyl, cyano, $(C_1\text{-}C_6)$alkylamino, oxo, $(C_1\text{-}C_6)$alkoxy, $(C_2\text{-}C_6)$alkenyl, $(C_2\text{-}C_6)$alkynyl, di$(C_1\text{-}C_6)$alkylamino, —C(O)$R^8$, —COO$R^8$, —C(O)N$R^8R^{8'}$, —N$R^8$C(O)$R^{8'}$, $(C_1\text{-}C_6)$alkyl, substituted $(C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
wherein $R^3$, $R^{3a}$, $R^4$, $R^{4a}$, $R^5$ and $R^{5a}$ are independently selected from H, $C_{1-3}$ alkyl, and substituted alkyl;
or wherein $R^3$ and $R^{3a}$ together form oxo, or $R^4$ and $R^{4a}$ together form oxo, or $R^5$ and $R^{5a}$ together form oxo;
wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;
wherein $R^x$ is selected from H, $(C_1\text{-}C_3)$haloalkyl, and $(C_1\text{-}C_3)$ alkyl; and
wherein each substituted alkyl, substituted aryl, heteroaryl, substituted heteroaryl, substituted cycloalkyl and substituted saturated or partially saturated heterocyclyl is substituted with one to three groups independently selected from halo, —NH$_2$, hydroxyl, cyano, $(C_1\text{-}C_6)$alkylamino, $(C_1\text{-}C_6)$haloalkyl, oxo, $(C_1\text{-}C_6)$alkoxy, $C_1\text{-}C_6)$alkoxy$(C_1\text{-}C_6)$ alkyl, $(C_1\text{-}C_6)$alkyl, $(C_2\text{-}C_6)$alkenyl, $(C_2\text{-}C_6)$alkynyl, di$(C_1\text{-}C_6)$alkylamino, —C(O)$R^8$, —COO$R^8$, —C(O)N$R^8R^{8'}$, and —N$R^8$C(O)$R^{8'}$, and pharmaceutically acceptable derivatives thereof;
provided the basic substiuent is not 2-pyridyl, 3-pyridyl or 2-oxo-piperaziny-4-ylmethyl.

The invention also relates to compounds of Formula II wherein X is selected from NH and N$R^a$; and wherein $R^a$ is $(C_{1-3})$alkyl or Boc; in conjunction with any of the above or below embodiments.

The invention also relates to compounds of Formula II wherein X is NH; in conjunction with any of the above or below embodiments.

The invention also relates to compounds of Formula II wherein R is selected from 9-11 membered fused bicyclic carbocyclic or heterocyclic ring substituted with one to two basic moieties, and optionally substituted with one to three groups independently selected from halo, hydroxyl, cyano, oxo, $(C_1\text{-}C_6)$alkoxy, $(C_2\text{-}C_6)$alkenyl, $(C_2\text{-}C_6)$alkynyl, —C(O)$R^8$, —COO$R^8$, —C(O)N$R^8R^{8'}$, —N$R^8$C(O)$R^{8'}$, $(C_1\text{-}C_6)$alkyl, substituted $(C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; in conjunction with any of the above or below embodiments.

The invention also relates to compounds of Formula II wherein R is a partially unsaturated carbocyclic ring, such as 1,2,3,4-tetrahydronaphthyl or indanyl; substituted with a basic moiety, optionally substituted with chloro; in conjunction with any of the above or below embodiments.

The invention also relates to compounds of Formula II wherein R is selected from 1,2,3,4-tetrahydronaphth-1-yl, 1,2,3,4-tetrahydronaphth-2-yl, indan-1-yl and indan-2-yl; substituted with a basic moiety, optionally substituted with chloro; in conjunction with any of the above or below embodiments.

The invention also relates to compounds of Formula II wherein R is partially unsaturated heterocyclyl, such as chroman and 2,2-dioxo-3,4-dihydro-1H-2,1-benzothiazinyl; substituted with a basic moiety, optionally substituted with chloro; in conjunction with any of the above or below embodiments.

The invention also relates to compounds of Formula II wherein R is chroman-4-yl, or 2,2-dioxo-3,4-dihydro-1H-2, 1-benzothiazin-4-yl; substituted with a basic moiety, optionally substituted with chloro; in conjunction with any of the above or below embodiments.

The invention also relates to compounds of Formula II wherein R is selected from phenyl and 5-6 membered heteroaryl; wherein R is substituted with one to two basic moieties, and optionally substituted with one to three groups independently selected from halo, hydroxyl, cyano, oxo, $(C_1\text{-}C_6)$alkoxy, —C(O)$R^8$, —COO$R^8$, —C(O)N$R^8R^{8'}$, —N$R^8$C(O)$R^{8'}$, $(C_1\text{-}C_6)$alkyl, substituted $(C_1\text{-}C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; in conjunction with any of the above or below embodiments.

The invention also relates to compounds of Formula II wherein R is phenyl substituted with a basic moiety selected from $(C_1\text{-}C_6)$alkylamino$(C_1\text{-}C_6)$alkyl, $C_{1-4}$-alkylamino-$C_{2-6}$- alkenyl, 5-8 membered nitrogen-containing heterocyclyl- $C_{2-6}$-alkenyl, and heterocyclyl-($C_1$-$C_6$)alkylamino($C_2$-$C_6$) alky; in conjunction with any of the above or below embodiments.

The invention also relates to compounds of Formula II wherein R is selected from 3-((piperidin-1-ylethyl) aminomethyl)phenyl and 4-imidazolin-2-ylphenyl; in conjunction with any of the above or below embodiments.

The invention also relates to compounds of Formula II wherein R is phenyl-($C_{1-3}$)-alkyl substituted with a basic moiety, such as 4-(imidazolin-2-yl)phenylmethyl, 4-(imidazolin-2-yl)phenylethyl and 4-(imidazolin-2-yl)phenylpropyl; in conjunction with any of the above or below embodiments.

The invention also relates to compounds of Formula II wherein $R^1$ is H or methyl; in conjunction with any of the above or below embodiments.

The invention also relates to compounds of Formula I wherein $R^2$ is selected from phenyl-($C_{2-4}$)-alkenyl, phenyl, naphthyl, 5-membered nitrogen containing heteroaryl, 5-membered sulfur containing heteroaryl, 6-membered nitrogen containing heteroaryl, 9-membered heterocyclyl, and 10-membered heterocyclyl; in conjunction with any of the above or below embodiments.

The invention also relates to compounds of Formula I wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 2-thienyl, isoxazolthienyl, benzothienyl, thieno[3,2-c]pyridinyl, naphthyl, phenyl, 3-pyridinyl, tetrahydroisoquinolinyl, quinolinyl and isoquinolinyl; wherein $R^2$ is optionally substituted with one to five groups independently selected from halo, —$NH_2$, hydroxyl, cyano, $C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, ($C_1$-$C_4$)alkylamino, ($C_1$-$C_4$)haloalkyl, oxo, ($C_1$-$C_4$)alkoxy, $C_1$-$C_4$)alkoxy($C_1$-$C_4$)alkyl, ($C_1$-$C_4$)alkyl, ($C_2$-$C_4$)alkenyl, ($C_2$-$C_4$)alkynyl, di($C_1$-$C_4$)alkylamino, —C(O)$R^8$, —COO$R^8$, —C(O)N$R^8R^{8'}$, and —N$R^8$C(O)$R^{8'}$; in conjunction with any of the above or below embodiments.

The invention also relates to compounds of Formula I wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; and wherein $R^2$ is optionally substituted; preferably with one or two groups independently selected from methyl, chloro, methoxy, —$OCF_3$ or —$CF_3$; such as 2,4,6-trimethylphenyl, 3,4-dichlorophenyl, 3-chloro-4-methylphenyl, 4-chloro-3-methylphenyl, 3-trifluoromethylphenyl, 4-trifluoromethylphenyl, 4-trifluoromethoxyphenyl, 4-methoxyphenyl, 4-methylphenyl, 4-chlorophenyl and 4-tert-butylphenyl; in conjunction with any of the above or below embodiments.

The invention also relates to compounds of Formula II wherein the basic moieties on R are independently selected from amino, cycloalkylamino($C_1$-$C_6$)alkyl, cycloalkyl($C_1$-$C_6$)alkylamino($C_1$-$C_6$)alkyl, heterocyclylamino($C_1$-$C_6$) alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$)alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-($C_1$-$C_6$)alkylamino ($C_2$-$C_6$)alkyl, 5-6 membered heterocyclyloxy, 5-6 membered nitrogen-containing heterocyclyl and 5-7 membered nitrogen-containing heterocyclyl-alkyl; and wherein each of said basic substituents is optionally substituted with one to three groups independently selected from halo, —$NH_2$, hydroxyl, cyano, —$CF_3$, ($C_1$-$C_6$) alkylamino, oxo, ($C_1$-$C_6$)alkoxy, ($C_2$-$C_6$)alkenyl, ($C_2$-$C_6$) alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, ($C_1$-$C_6$)alkylamino, $C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; in conjunction with any of the above or below embodiments.

The invention also relates to compounds of Formula II wherein the basic moieties on R are independently selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula II wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di (isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula II wherein $R^3$ and $R^{3a}$ together form oxo; wherein $R^4$ and $R^{4a}$ are independently selected from H and $C_{1-3}$ alkyl; and wherein $R^5$ and $R^{5a}$ are independently H; in conjunction with any of the above or below embodiments.

Alternatively, the invention also relates to compounds wherein $R^3$ and $R^{3a}$ together form oxo; wherein $R^4$ and $R^{4a}$ are independently selected from H and methyl; and wherein $R^5$ and $R^{5a}$ are independently H; in conjunction with any of the above or below embodiments.

The invention also relates to compounds wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono-alkylamino, dialkylamino, and trifluoromethyl; in conjunction with any of the above or below embodiments.

The invention also relates to compounds of Formula II $R^x$ is H, methyl or trifluoromethyl, such as H; in conjunction with any of the above or below embodiments.

The invention also relates to compounds of Formula III

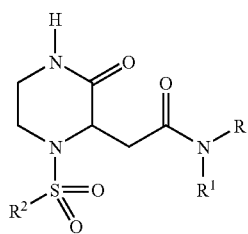

III wherein R is a 9-11 membered fused bicyclic carbocyclic or heterocyclic ring substituted with one to two basic moieties, and optionally substituted with one to three groups independently selected from halo, —$NH_2$, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, $C_1$-$C_6$alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein each substituted ($C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$) alkylamino, —C(O)$R^8$, —COO$R^8$, —C(O)N$R^8R^{8'}$, and —N$R^8$C(O)$R^{8'}$;

wherein $R^1$ is selected from H, and $C_{1-2}$-alkyl;

wherein $R^2$ is selected from arylalkenyl, aryl, and heterocyclyl selected from thienyl, quinolinyl, isoquinolinyl, 3-pyridyl, thiazol-4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, $C_1$-$C_6$alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$) alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and pharmaceutically acceptable derivatives thereof; provided the basic substiuent is not 2-pyridyl, 3-pyridyl or 2-oxo-piperaziny-4-ylmethyl.

The invention also relates to compounds of Formula III wherein R is a partially unsaturated carbocyclic ring, such as 1,2,3,4-tetrahydronaphthyl or indanyl.

The invention also relates to compounds of Formula III wherein R is selected from 1,2,3,4-tetrahydronaphth-1-yl, 1,2,3,4-tetrahydronaphth-2-yl, indan-1-yl and indan-2-yl.

The invention also relates to compounds of Formula III wherein R is partially unsaturated heterocyclyl, such as chroman and 2,2-dioxo-3,4-dihydro-1H-2,1-benzothiazinyl; substituted with a basic moiety, optionally substituted with chloro; in conjunction with any of the above or below embodiments.

The invention also relates to compounds of Formula III wherein R is chroman-4-yl, or 2,2-dioxo-3,4-dihydro-1H-2,1-benzothiazin-4-yl; substituted with a basic moiety, optionally substituted with chloro; in conjunction with any of the above or below embodiments.

The invention also relates to compounds wherein each $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein $R^2$ is optionally substituted with one to five groups independently selected from halo, —$NH_2$, hydroxyl, cyano, —$CF_3$, ($C_1$-$C_6$)alkylamino, oxo, ($C_1$-$C_6$) alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O) $R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted $C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, halo ($C_1$-$C_6$)alkyl, oxo, ($C_1$-$C_6$)alkoxy, ($C_1$-$C_6$)alkoxy($C_1$-$C_6$) alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; wherein $R^1$ is selected from H and $C_{1-2}$-alkyl; wherein the basic substituent on R is selected from amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino($C_1$-$C_6$)alkyl, ($C_1$-$C_6$) alkylamino($C_1$-$C_6$)alkyl, $C_{1-4}$-alkylamino-$C_{2-6}$-alkenyl, 5-8 membered nitrogen-containing heterocyclyl-$C_{2-6}$-alkenyl, heterocyclyl-$C_1$-$C_6$)alkylamino($C_2$-$C_6$)alkyl, 5-6 membered heterocyclyloxy, 5-6 membered nitrogen-containing heterocyclyl and 5-7 membered nitrogen-containing heterocyclylalkyl; and wherein each of said basic substituents is optionally substituted with one to three groups independently selected from halo, —$NH_2$, hydroxyl, cyano, —$CF_3$, ($C_1$-$C_6$) alkylamino, oxo, ($C_1$-$C_6$)alkoxy, ($C_2$-$C_6$)alkenyl, ($C_2$-$C_6$) alkynyl, di($C_1$-$C_6$)alkylamino, —$C(O)R^8$, —$COOR^8$, —$C(O)NR^8R^{8'}$, —$NR^8C(O)R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, $C_1$-$C_4$)alkylamino, ($C_1$-$C_4$)haloalkyl, oxo, ($C_1$-$C_4$)alkoxy, ($C_1$-$C_4$)alkoxy($C_1$-$C_4$)alkyl, $C_1$-$C_4$)alkyl, ($C_2$-$C_4$)alkenyl, ($C_2$-$C_4$)alkynyl, di($C_1$-$C_4$)alkylamino, —$C(O)R^8$, —$COOR^8$, —$C(O)NR^8R^{8'}$, and —$NR^8C(O)R^{8'}$; in conjunction with any of the above or below embodiments.

The invention also relates to compounds wherein $R^2$ is selected from phenyl-CH═CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each $R^2$ is said optionally substituted; wherein $R^a$ is H; and wherein the basic substituent on R is selected from amino, mono-$C_{1-4}$-alkylamino-$C_{1-4}$-alkyl, di-$C_{1-4}$-alkylamino-$C_{1-4}$-alkyl, mono-$C_{1-4}$- alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula III wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV

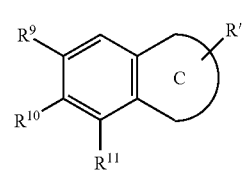

wherein the C ring is a 4- to 7- membered saturated carbocyclic or heterocyclic moiety; optionally substituted with halo, —$NH_2$, hydroxyl, cyano, oxo, ($C_1$-$C_6$)alkoxy, ($C_2$-$C_6$)alkenyl, ($C_2$-$C_6$)alkynyl, —$C(O)R^8$, —$COOR^8$, —$C(O)NR^8R^{8'}$, —$NR^8C(O)R^{8'}$, $C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein R' is

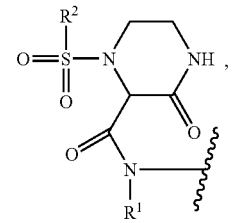

wherein $R^1$ is independently selected from H and $C_{1-2}$-alkyl;
wherein $R^2$ is selected from arylalkenyl, aryl, and heterocyclyl selected from thienyl, quinolinyl, isoquinolinyl, 3-pyridyl, thiazol4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$,—$NR^8C(O)R^{8'}$, ($C_1$-$C_6$)alkyl, substituted ($C_1$-$C_6$) alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
wherein each substituted ($C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$) alkylamino, —$C(O)R^8$, —$COOR^8$, —$C(O)NR^8R^{8'}$, and —$NR^8C(O)R^{8'}$;
wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and
wherein $R^9$, $R^{10}$ and $R^{11}$ are the same or different and represent H, halo, —$NH_2$, hydroxyl, cyano, —$CF_3$, ($C_1$-$C_6$) alkylamino, oxo, ($C_1$-$C_6$)alkoxy, ($C_2$-$C_6$)alkenyl, ($C_2$-$C_6$) alkynyl, di($C_1$-$C_6$)alkylamino, —$C(O)R^8$, —$COOR^8$, —C(O)NR$^8$R$^{8'}$, —NR$^8$C(O)R$^{8'}$, a basic moiety, (C$_1$-C$_6$) alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein each substituted (C$_1$-C$_6$)alkyl, substituted aryl, substituted heteroaryl, substituted cycloalkyl and substituted saturated or partially saturated heterocyclyl is substituted with one to three groups independently selected from halo, —NH$_2$, hydroxyl, cyano, (C$_1$-C$_6$)alkylamino, (C$_1$-C$_6$)haloalkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$) alkylamino, —C(O)R$^8$, —COOR$^8$, —C(O)NR$^8$R$^{8'}$, and —NR$^8$C(O)R$^{8'}$;

provided at least one of R$^9$, R$^{10}$ and R$^{11}$ is a basic moiety; further provided the basic substiuent is not 2-pyridyl, 3-pyridyl or 2-oxo-piperaziny-4-ylmethyl; and pharmaceutically acceptable derivatives thereof.

The invention also relates to compounds of Formula IV wherein R$^9$ and R$^{11}$ are H; and wherein R$^{10}$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl.

The invention also relates to compounds of Formula IV wherein R$^{10}$ and R$^{11}$ are H; and wherein R$^9$ is selected from amino, aminomethyl, isopropylaminomethyl, t-butylaminomethyl, 2-t-butylaminoethyl, 2-tert-butylamino-1-methylethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV wherein R$^9$ and R$^{10}$ are H; and wherein R$^{11}$ is selected from amino, aminomethyl, isopropylaminomethyl, t-butylaminomethyl, 2-t-butylaminoethyl, 2-tert-butylamino-1-methylethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl) propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula IV wherein the C ring is selected from

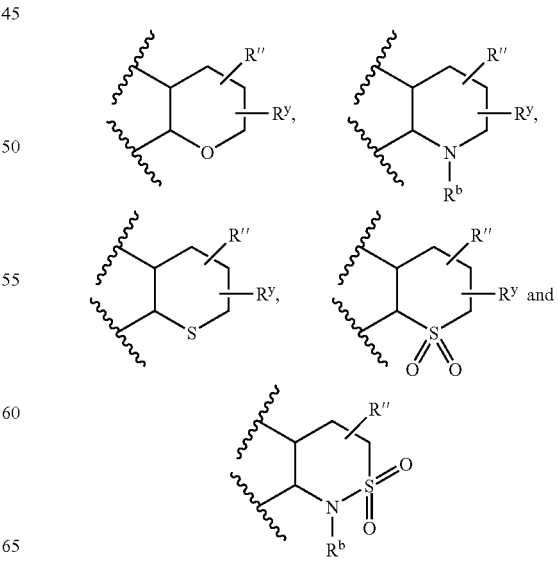

wherein $R^b$ is independently selected from R', H and $C_{1-2}$-alkyl; wherein $R^y$ is selected from halo, hydroxyl, cyano, oxo, $(C_1-C_4)$alkoxy, $(C_2-C_4)$alkenyl, $(C_2-C_4)$alkynyl, —C(O)R$^8$, —COOR$^8$, —C(O)NR$^8$R$^{8'}$, —NR$^8$C(O)R$^{8'}$, $(C_1-C_4)$alkyl, substituted $(C_1-C_4)$alkyl, phenyl, substituted phenyl, 5-6 membered heteroaryl, substituted 5-6 membered heteroaryl, $C_{3-6}$-cycloalkyl, substituted $C_{3-6}$-cycloalkyl, substituted saturated or partially saturated 5-6 membered heterocyclyl and unsubstituted saturated or partially saturated 5-6 membered heterocyclyl; and wherein R" is R' when $R^b$ is hydrogen or $C_{1-2}$alkyl, or R" is hydrogen when $R^b$ is R'; in conjunction with any of the above or below embodiments.

The invention also relates to compounds of Formula IV wherein $R^2$ is selected from phenyl-CH=CH—, tetrahydronaphthyl, naphtho[2,3-d]dioxol-6-yl, 1-benzofur-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, 2-naphthyl, phenyl, 3-pyridyl, tetrahydroisoquinolyl, 8-quinolyl and 5-isoquinolyl; wherein $R^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each $R^2$ is optionally substituted with one to five groups independently selected from halo, —NH$_2$, hydroxyl, cyano, —CF$_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)R$^8$, —COOR$^8$, —C(O)NR$^8$R$^{8'}$, —NR$^8$C(O)R$^8$, $C_1-C_6$)alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted $(C_1-C_6)$alkyl, substituted aryl, substituted heteroaryl, substituted cycloalkyl and substituted saturated or partially saturated heterocyclyl is substituted with one to three groups independently selected from halo, —NH$_2$, hydroxyl, cyano, $(C_1-C_6)$alkylamino, $C_1-C_6$)haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)R$^8$, —COOR$^8$, —C(O)NR$^8$R$^{8'}$, and —NR$^8$C(O)R$^{8'}$; in conjunction with any of the above or below embodiments.

The invention also relates to compounds of Formula IV wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 3-chloro-4-methylphenyl, 4-chloro-3-methylphenyl, 3-trifluoromethylphenyl, 4-trifluoromethylphenyl, 4-trifluoromethoxyphenyl, 3-methylphenyl, 2,1,3-benzoxadiazol-4-yl, thien-2-yl, 3-pyridyl, 8-quinolyl and 5-isoquinolyl; in conjunction with any of the above or below embodiments.

The invention also relates to compounds of Formula IV wherein R$^1$ is H; in conjunction with any of the above or below embodiments.

The invention also relates to compounds of Formula IV wherein R$^2$ is 2-naphthyl; in conjunction with any of the above or below embodiments.

The invention also relates to compounds of Formula IV wherein R$^2$ is 3,4-dichlorophenyl; in conjunction with any of the above or below embodiments.

The invention also relates to compounds of Formula IV wherein R$^2$ is 3-trifluoromethylphenyl; in conjunction with any of the above or below embodiments.

The invention also relates to compounds of Formula V

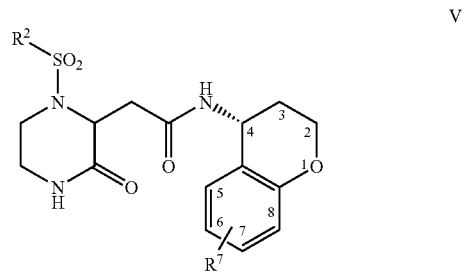

wherein $R^2$ is selected from naphthyl, phenyl, thienyl, heterocyclyl selected from thienyl, benzoxadiazolyl, quinolinyl and isoquinolinyl, and wherein each is optionally substituted with one to three substituents selected from chloro, fluoro, methoxy, methyl, trifluoromethyl and phenyl;

wherein $R^7$ is selected from amino-(CH$_2$)$_p$—, mono(C$_{1-4}$)alkylamino-(CH$_2$)$_p$—, di(C$_{1-4}$)alkylamino-(CH$_2$)$_p$—, amino-(C$_{2-4}$)-alkenyl, (C$_{1-4}$)alkylamino-(C$_{2-4}$)-alkenyl, di(C$_{1-4}$)alkylamino-(C$_{2-4}$)-alkenyl, 5-7 membered nitrogen-containing heterocyclyl-(C$_{2-4}$)-alkenyl, 5-7 membered nitrogen-containing heterocyclyl and 5-7 membered nitrogen-containing heterocyclyl-(CH$_2$)$_p$-optionally substituted with one to three groups independently selected from halo, —NH$_2$, hydroxyl, cyano, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, =NCN, (C$_1$-C$_6$)alkyl, substituted (C$_1$-C$_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted (C$_1$-C$_6$)alkyl, substituted aryl, substituted heteroaryl, substituted cycloalkyl and substituted saturated or partially saturated heterocyclyl is substituted with one to three groups independently selected from halo, —NH$_2$, hydroxyl, cyano, (C$_1$-C$_6$)alkylamino, C$_1$-C$_6$) haloalkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein p is 0-2;

wherein R$^7$ is at position 6, 7 or 8; and wherein R$^8$ and R$^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and pharmaceutically acceptable derivatives thereof;

provided R$^7$ is not 2-pyridyl, 3-pyridyl or 2-oxo-piperaziny-4-ylmethyl.

The invention also relates to compounds of Formula V wherein R$^7$ is selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

The invention also relates to compounds of Formula V wherein $R^7$ is at position 7; in conjunction with any of the above or below embodiments.

The invention also relates to compounds of Formula V wherein $R^2$ is 2-naphthyl, 3,4-dichlorophenyl or 3-trifluoromethylphenyl; in conjunction with any of the above or below embodiments.

The invention also relates to compounds of Formula VI

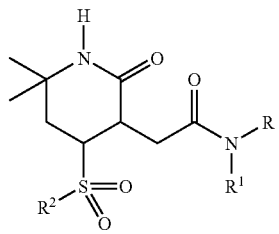

VI wherein R is a 9-11 membered fused bicyclic carbocyclic or heterocyclic ring substituted with one to three basic moieties, and optionally substituted with one to two groups independently selected from halo, —$NH_2$, hydroxyl, cyano, oxo, ($C_1$-$C_6$)alkoxy, ($C_2$-$C_6$)alkenyl, ($C_2$-$C_6$)alkynyl, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;

wherein each substituted ($C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^1$ is selected from H, and $C_{1-2}$-alkyl;

wherein $R^2$ is selected from arylalkenyl, aryl, and heterocyclyl selected from thienyl, quinolinyl, isoquinolinyl, 3-pyridyl, thiazol4-yl, 4-imidazolyl, benzofuryl, benzoxadiazolyl, benzothiadiazolyl, benzothiazolyl, 1H-pyrazolyl, isoxazolthienyl, benzothienyl, thieno[3,2-c]pyridinyl, and tetrahydroisoquinolinyl, wherein $R^2$ is optionally substituted with one to five groups independently selected from halo, —$NH_2$, hydroxyl, cyano, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, $C_1$-$C_6$alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$) alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and pharmaceutically acceptable derivatives thereof;

provided the basic substiuent is not 2-pyridyl, 3-pyridyl or 2-oxo-piperaziny-4-ylmethyl.

The invention also relates to compounds of Formula VI wherein R is a partially unsaturated carbocyclic ring, such as 1,2,3,4-tetrahydronaphthyl or indanyl; substituted with a basic moiety, optionally substituted with chloro; in conjunction with any of the above or below embodiments.

The invention also relates to compounds of Formula VI wherein R is selected from 1,2,3,4-tetrahydronaphth-1-yl, 1,2,3,4-tetrahydronaphth-2-yl, indan-1-yl and indan-2-yl; substituted with a basic moiety, optionally substituted with chloro; in conjunction with any of the above or below embodiments.

The invention also relates to compounds of Formula VI wherein R is partially unsaturated heterocyclyl, such as chroman and 2,2-dioxo-3,4-dihydro-1H-2,1-benzothiaziny; substituted with a basic moiety, optionally substituted with chloro; in conjunction with any of the above or below embodiments.

The invention also relates to compounds of Formula VI wherein R is chroman-4-yl, or 2,2-dioxo-3,4-dihydro-1H-2,1-benzothiazin-4-yl; substituted with a basic moiety, optionally substituted with chloro; in conjunction with any of the above or below embodiments.

The invention also relates to compounds wherein each $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein $R^2$ is optionally substituted with one to five groups independently selected from halo, —$NH_2$, hydroxyl, cyano, —$CF_3$, ($C_1$-$C_6$)alkylamino, oxo, ($C_1$-$C_6$) alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted $C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)

alkyl, $(C_1-C_6)$alkyl, $(C_2-C_6)$alkenyl, $(C_2-C_6)$alkynyl, di$(C_1-C_6)$alkylamino, —C(O)R$^8$, —COOR$^8$, —C(O)NR$^8$, and —NR$^8$C(O)R$^8$; wherein R$^1$ is selected from H and $C_{1-2}$-alkyl; wherein the basic substituent on R is selected from amino, cycloalkylamino$(C_1-C_6)$alkyl, cycloalkyl$(C_1-C_6)$alkylamino$(C_1-C_6)$alkyl, heterocyclylamino$(C_1-C_6)$alkyl, heterocyclyl$(C_1-C_6)$alkylamino$(C_1-C_6)$alkyl, arylamino$(C_1-C_6)$alkyl, aryl$(C_1-C_6)$alkylamino$(C_1-C_6)$alkyl, $C_{1-6}$-alkylamino-$C_{1-6}$-alkoxy, $C_{1-6}$-alkylamino-$C_{1-6}$-alkoxy-$C_{1-6}$-alkoxy, amino$(C_1-C_6)$alkoxy, amino$(C_1-C_6)$alkyl, $(C_1-C_6)$alkylamino$(C_1-C_6)$alkyl, $C_{1-4}$-alkylamino-$C_{2-6}$-alkenyl, 5-8 membered nitrogen-containing heterocyclyl-$C_{2-6}$-alkenyl, heterocyclyl-$C_1-C_6$)alkylamino$(C_2-C_6)$alkyl, 5-6 membered heterocyclyloxy, 5-6 membered nitrogen-containing heterocyclyl and 5-7 membered nitrogen-containing heterocyclylalkyl; and wherein each of said basic substituents is optionally substituted with one to three groups independently selected from halo, —NH$_2$, hydroxyl, cyano, —CF$_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)R$^8$, —COOR$^8$, —C(O)NR$^8$R$^8$, —NR$^8$C(O)R$^8$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $(C_1-C_6)$alkyl, substituted aryl substituted heteroaryl and substituted saturated or partially saturated heterocyclyl is optionally substituted with one to three groups independently selected from halo, —NH$_2$, hydroxyl, cyano, $C_1-C_4$)alkylamino, $(C_1-C_4)$haloalkyl, oxo, $(C_1-C_4)$alkoxy, $(C_1-C_4)$alkoxy$(C_1-C_4)$alkyl, $C_1-C_4$)alkyl, $(C_2-C_4)$alkenyl, $(C_2-C_4)$alkynyl, di$(C_1-C_4)$alkylamino, —C(O)R$^8$, —COOR$^8$, —C(O)NR$^8$R$^8$, and —NR$^8$C(O)R$^8$; in conjunction with any of the above or below embodiments.

The invention also relates to compounds wherein R$^2$ is selected from phenyl-CH=CH—, tetrahydronaphthyl, 2,1,3-benzoxadiazol-4-yl, thien-2-yl, 2-naphthyl, phenyl, 3-pyridyl, 8-quinolyl and 5-isoquinolyl; wherein each R$^2$ is said optionally substituted; wherein R$^1$ is H; and wherein the basic substituent on R is selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl; in conjunction with any of the above or below embodiments.

The invention also relates to compounds of Formula VI wherein the basic moieties on R are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutylaminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminomethyl, cyclobutylaminomethyl, cyclobutylaminoethyl, cyclobutylmethylaminomethyl, cyclobutylmethylaminomethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl; in conjunction with any of the above or below embodiments.

A family of specific compounds of particular interest within Formula I consists of compounds and pharmaceutically-acceptable salts thereof as follows:

2-[3-Oxo-1-(2,4,6-trimethylbenzenesulfonyl)-piperizin-2(R,S)-yl]-N-(1,2,3,4-tetrahydronaphthalen-1-yl)-acetamide;

N-((1R)-6-(((1,1-Dimethylethyl)amino)methyl)-1,2,3,4-tetrahydro-1-naphthalenyl)-2-((2R,S)-1-((4-methylphenyl)sulfonyl)-3-oxo-2-piperazinyl)acetamide;

2-[3-Oxo-1-(toluene4-sulfonyl)piperizin-2-yl]-N-(6-piperidin-1-ylmethyl-1,2,3,4-tetrahydronaphthalen-1-yl)-acetamide;

N-[7-(tert-Butylamino-methyl)-6-chloro-chroman-4-yl]-2-[3-oxo-1-(toluene4-sulfonyl)-piperazin-2-yl]-acetamide;

N-[7-(tert-Butylamino-methyl)-6-chloro-chroman-4-yl]-2-[3-oxo-1-(4-methoxy-benzenesulfonyl)-piperazin-2-yl]-acetamide;

N-[7-(tert-Butylamino-methyl)-6-chloro-chroman-4-yl]-2-[3-oxo-1-(4-chloro-benzenesulfonyl)-piperazin-2-yl]-acetamide;

N-[7-(tert-Butylamino-methyl)-6-chloro-chroman-4-yl]-2-[3-oxo-1-(3-trifluoromethyl-benzenesulfonyl)-piperazin-2-yl]-acetamide;

N-((4R)-2,2-dimethyl-7-(2-piperidinyl)-3,4-dihydro-2H-chromen-4-yl)-2-((2R)-1-((4-methylphenyl)sulfonyl)-3-oxo-2-piperazinyl)acetamide;

2-((2R,S)-5,5-dimethyl-3-oxo-1-((2,4,6-trimethylphenyl)sulfonyl)-2-piperazinyl)-N-(1,2,3,4-tetrahydro-1-naphthalenyl)acetamide;

N-[6-(tert-Butylamino-methyl)-1,2,3,4-tetrahydro-naphthalen-1-yl]-2-[5,5-dimethyl-3-oxo-1-(2,4,6-trimethyl-benzenesulfonyl)-piperazin-2(R,S)-yl]-acetamide N-((1R,S)-6-(((1,1-dimethylethyl)amino)methyl)-1,2,3,4-tetrahydro-1-naphthalenyl)-2-((2R,S)-5,5-dimethyl-1-((4-methylphenyl)sulfonyl)-3-oxo-2-piperazinyl)acetamide;

2-[5,5-Dimethyl-3-oxo-1-(toluene-4-sulfonyl)-piperizin-2(R,S)-yl]-N-(6-piperidin-1-ylmethyl-1,2,3,4-tetrahydronaphthalen-1(R)-yl)-acetamide; and N-((4R)-6-Chloro-7-(((1,1-dimethylethyl)amino)methyl)-3,4-dihydro-2H-chromen-4-yl)-2-((2R,S)-5,5-dimethyl-3-oxo-1-((2,4,6-trimethylphenyl)sulfonyl)-2-piperazinyl)acetamide.

Indications

The present invention also provides methods of using the compounds in for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The invention also provides for the use of the compounds of the present invention for the prevention or for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

Accordingly, the present invention also relates to the use of one or more of the compounds of the present invention in the manufacture of a medicament for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The compounds of this invention may also act as inhibitors of other receptors or kinases, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Definitions

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective pain therapeutic agents relieve the pain sensation of the patient. Alternatively, effective therapeutic agents for the treatment of inflammation minimize the damage from the inflammation, and the like.

The term "treatment" includes therapeutic treatment as well as prophylactic treatment (either preventing the onset of disorders altogether or delaying the onset of a pre-clinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms, or as otherwise indicated. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkyl" also includes divalent radicals such as methylenyl and ethyleneyl.

The term "alkenyl" embraces linear or branched radicals having at least one carbon-carbon double bond of two to about twenty carbon atoms or, preferably, two to about twelve carbon atoms, or as otherwise indicated. More preferred alkenyl radicals are "lower alkenyl" radicals having two to about four carbon atoms. Examples of alkenyl radicals include ethenyl, 2-propenyl, allyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms, or as otherwise indicated. More preferred alkynyl radicals are "lower alkynyl" radicals having two to about four carbon atoms. Examples of alkynyl radicals include ethynyl, 2-propynyl, and 4-methylbutynyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "alkoxyalkyl" embraces linear or branched alkyl radicals having one to about ten carbon atoms any one of which may be substituted with one or more alkoxyl radicals. More preferred alkoxyalkyl radicals are "lower alkoxyalkyl" radicals respectively having one to six carbon atoms. Examples of such radicals include methoxymethyl, methoxyethyl, and the like. Even more preferred are lower alkoxyalkyl radicals respectively having one to three carbon atoms alkyl radicals.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 8-membered heteromonocyclic group containing 1 to 4 nitrogen atoms [e.g. pyrrolidinyl, imidazolidinyl, piperidino, piperazinyl]; saturated 3 to 8-membered heteromonocyclic group containing 1 to 2 oxygen atoms and 1 to 3 nitrogen atoms [e.g. morpholinyl]; saturated 3 to 8-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridinyl, 3-pyridinyl, 4-pyridinyl, pyrimidinyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyanl, 3-furyanl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals:unsaturated condensed heterocyclic group containing 1 to 5 nitrogen atoms, for example, indolinyl, isoindolinyl, indolizinyl, benzimidazolyl, quinolinyl, isoquinolinyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolinyl, isoquinolinyl, imidazolyl, pyridinyl, thienyl, thiazolyl, oxazolyl, furanyl, and pyrazinyl. Even more preferred heteroaryl radicals are 5- or 6-membered heteroaryl, containing one or two heteroatoms selected from sulfur, nitrogen and oxygen, selected from thienyl, furanyl, pyrrolyl, thiazolyl, oxazolyl, imidazolyl, pyrazolyl, isoxazolyl, isothiazolyl, pyridinyl, piperidinyl and pyrazinyl.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$).

The term "cycloalkylaminoalkyl" includes "N-cycloalkylaminoalkyl" and "N,N-dicycloalkylaminoalkyl" where alkyl radicals are independently substituted, respectively, with one cycloalkyl radical, or two cycloalkyl radicals. More preferred cycloalkylaminoalkyl radicals are "lower cycloalkylaminoalkyl" radicals having alkyl radicals with one to six carbon atoms. Even more preferred are lower cycloalkylaminoalkyl radicals having alkyl radicals with one to three carbon atoms. Examples of such lower alkylaminosulfonyl radicals include N-cyclohexylaminomethyl, and N-cyclopentylaminoethyl.

The term "cycloalkyl-alkylaminoalkyl" embraces cycloalkyl radicals as described above, attached to an alkylaminoalkyl radical. More preferred are lower cycloalkyl-alkylaminoalkyl radicals independently having alkyl radicals of one to three carbon atoms.

The term "N-arylaminoalkyl" denotes alkyl radicals substituted with an aryl radical. More preferred arylaminoalkyl radicals are "lower N-arylaminoalkyl" radicals having alkyl radicals of one to six carbon atoms. Even more preferred are phenylaminoalkyl radicals having one to three carbon atoms. Examples of such radicals include N-phenylaminomethyl and N-phenylaminoethyl.

The term "aralkylaminoalkyl" embraces aralkyl radicals as described above, attached to an aminoalkyl radical. More preferred are lower arylalkylaminoalkyl radicals independently having alkyl radicals of one to three carbon atoms.

The term "heterocyclylaminoalkyl" embraces heterocyclyl radicals as described above, attached to an aminoalkyl radical.

The term "heteroarylalkylaminoalkyl" embraces heteroarylalkyl radicals as described above, attached to an aminoalkyl radical. More preferred are lower heteroarylalkylaminoalkyl radicals having, independently, alkyl radicals of one to three carbon atoms.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing $C_{3-6}$ cycloalkyl.

The terms "heterocyclylcarbonyl" denotes carbonyl radicals substituted with an heterocyclyl radical. More preferred are "optionally substituted 5-6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula H$_2$NC(=O)—.

The terms "N-alkylaminocarbonyl" and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals.

More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridinylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$-$C_3$-alkylamino-$C_1$-$C_3$-alkylamino radicals.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals independently having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxymethoxy, N,N-dimethylaminoethoxymethoxy, N,N-diethylaminomethoxymethoxy, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "aminoalkoxy" embraces alkoxy radicals substituted with an amino radical. More preferred aminoalkoxy radicals are "lower aminoalkoxy" radicals having alkoxy radicals of one to six carbon atoms. Suitable aminoalkoxy radicals may be aminoethoxy, aminomethoxy, aminopropoxy and the like.

The terms "N-aralkyl-N-alkylamino" and "N-alkyl-N-arylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclyloxy" embraces optionally substituted heterocyclyl radicals, as defined above, attached to an oxygen atom. Examples of such radicals include piperidyloxy.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl" embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl" includes saturated carbocyclic groups. Preferred cycloalkyl groups include $C_3$-$C_6$ rings. More preferred compounds include cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$-$C_6$ rings. More preferred compounds include, for example, cyclopentenyl, cyclopentadienyl, cyclohexenyl and cycloheptadienyl.

The term "basic moiety" or "basic moieties" means a chemical moiety that has a measured or calculated pKa of from about 7 to about 13. The term also can include a chemical moiety that is protonable, to some extent, between a pH range of from about 7 to about 10. Examples of basic moieties include, but are not limited to, amino, cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl-alkyl; more specifically amino, cycloalkylamino($C_1$-$C_6$)alkyl, cycloalkyl ($C_1$-$C_6$) alkylamino($C_1$-$C_6$)alkyl, heterocyclylamino($C_1$-$C_6$) alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, $C_1$-$C_4$)alkylamino-($C_2$-$C_6$)alkenyl, 5-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl($C_1$-$C_6$)alkyl; and more specifically, amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylaminomethyl)-vinyl, 1-(piperidin-1-ylmethyl)-vinyl, N-isobutyl-aminomethyl, N-isobutyl-aminoethyl, (2,2-dimethyl)

propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di (isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutyl-methylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl. Each basic moiety can be optionally substituted with one to three groups independently selected from halo, —$NH_2$, —OH, —CN, —$CF_3$, ($C_1$-$C_6$) alkylamino, haloalkyl, oxo, ($C_1$-$C_6$)alkoxy, ($C_1$-$C_6$)alkoxyalkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, =NCN; and ($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, haloalkyl, oxo, ($C_1$-$C_6$)alkoxy, $C_1$-$C_6$)alkoxyalkyl, ($C_1$-$C_6$)alkyl, ($C_2$-$C_6$) alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$. In one emodiment, the basic moiety is selected from cycloalkylamino($C_1$-$C_6$)alkyl, cycloalkyl($C_1$-$C_6$) alkylamino($C_1$-$C_6$) alkyl, heterocyclylamino($C_1$-$C_6$)alkyl, heterocyclyl($C_1$-$C_6$) alkylamino($C_1$-$C_6$)alkyl, arylamino($C_1$-$C_6$)alkyl, aryl($C_1$-$C_6$)alkylamino($C_1$-$C_6$)alkyl, ($C_1$-$C_6$)alkyl amino($C_1$-$C_6$) alkoxy, ($C_1$-$C_6$)alkylamino($C_1$-$C_6$)alkoxy($C_1$-$C_6$)alkoxy, amino($C_1$-$C_6$)alkoxy, amino($C_1$-$C_6$)alkyl, ($C_1$-$C_6$)alkylamino($C_1$-$C_6$)alkyl, ($C_1$-$C_4$)alkylamino-($C_2$-$C_6$)alkenyl, 4-8-membered nitrogen-containing heterocyclyl($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl-alkyl. In another emodiment, the basic moiety is selected from cycloalkylamino($C_1$-$C_6$)alkyl, cycloalkyl($C_1$-$C_6$) alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$) alkyl, aryl($C_1$-$C_6$)alkylamino($C_1$-$C_6$)alkyl, ($C_1$-$C_6$)alkyl amino($C_1$-$C_6$)alkoxy, ($C_1$-$C_6$)alkylamino-($C_1$-$C_6$)alkoxy ($C_1$-$C_6$)alkoxy, amino($C_1$-$C_6$)alkoxy, amino($C_1$-$C_6$)alkyl, $C_1$-$C_6$)alkylamino($C_1$-$C_6$)alkyl, ($C_1$-$C_4$)alkylamino-($C_2$-$C_6$) alkenyl, 4-8-membered nitrogen-containing heterocyclyl ($C_2$-$C_6$)alkenyl, heterocyclyl($C_1$-$C_6$)amino($C_2$-$C_6$)alkyl, 5-6 membered heterocyclyloxy, 5-6 membered nitrogen-containing heterocyclyl and 5-7 membered nitrogen-containing heterocyclyl-alkyl any of which are substituted by COO$R_8$, halo, $C_{1-6}$alkyl or cycloalkyl.

The term "comprising" is meant to be open ended, including the indicated component but not excluding other elements.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

The present invention preferably includes compounds that antagonize bradykinin 1.

The present invention also comprises the use of a compound of the invention, or pharmaceutically acceptable salt thereof, in the manufacture of a medicament for the treatment either acutely or chronically of pain or an inflammation mediated disease state, including those described previously. The compounds of the present invention are also useful in the manufacture of an anti-inflmmatory medicament. The compounds of the present invention are also useful in the manufacture of a medicament to attenuate or prevent disorders through inhibition of bradykinin 1. The compounds of the present invention are also useful in the manufacture of a medicament to treat pain.

The present invention comprises a pharmaceutical composition comprising a therapeutically-effective amount of a compound of Formulas I-VI in association with at least one pharmaceutically-acceptable carrier, adjuvant or diluent.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The present compounds may also be used in combination therapies with opioids and other anti-pain analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists, COX-2 inhibitors such as celecoxib, rofecoxib, valdecoxib, parecoxib, and darecoxib, NSAID's, and sodium channel blockers, among others. More preferred would be combinations with compounds selected from morphine, meperidine, codeine, pentazocine, buprenorphine, butorphanol, dezocine, meptazinol, hydrocodone, oxycodone, methadone, tetrahydrocannibinol, pregabalin, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−)

enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

Alternatively, the present compounds may also be used in co-therapies with other treatments for inflammation, e.g. steroids, NSAIDs, iNOS inhibitors, p38 inhibitors, TNF inhibitors, 5-lipoxygenase inhibitors, $LTB_4$ receptor antagonists and $LTA_4$ hydrolase inhibitors.

The present invention comprises a process for the preparation of a compound of Formula I-VI.

Compounds of the present invention can possess, in general, one or more asymmetric carbon atoms and are thus capable of existing in the form of optical isomers as well as in the form of racemic or non-racemic mixtures thereof. Unless otherwise indicated, the compounds of the present invention, as depicted or named, may exist as the racemate, a single enantiomer, or any uneven (i.e. non 50/50) mixture of enantiomers, and are all included in the family of compounds in Formula I-VI. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column, such as, for example, a CHIRAL-AGP column, optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. Preferred compounds of the invention have an R configuration at the amide bond for example

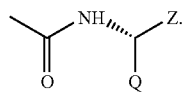

Compounds of the present invention can possess, in general, tautomeric forms, including any enolate anions, which are included in the family of compounds in Formula I-VI.

Also included in the family of compounds of Formula I-VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-VI may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, P-hydroxybutyric, salicylic, galactaric and galacturonic acid. Suitable pharmaceutically-acceptable base addition salts of compounds of Formula I-VI include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of Formula I-VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

General Synthetic Procedures

The compounds of the invention can be synthesized according to the following procedures of Schemes 1-20, wherein the substituents are as defined for Formulas I-VI, above, except where further noted.

Scheme 1

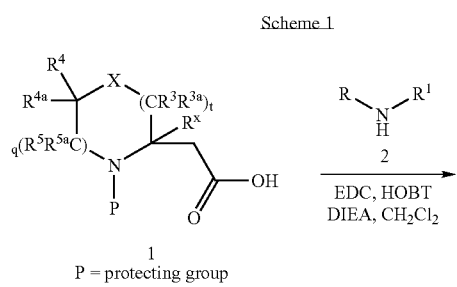

1
P = protecting group

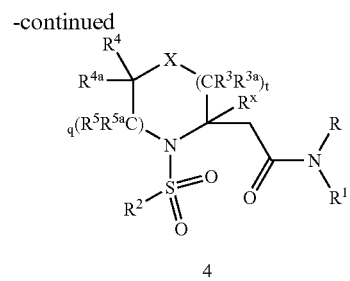

4

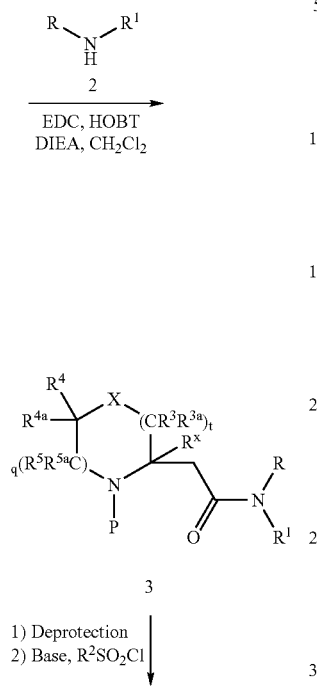

3

1) Deprotection
2) Base, R²SO₂Cl

Compounds of Formula I may be prepared in a convergent manner as described in Scheme 1. Acids 1 are coupled with the substituted amine 2 using standard peptide coupling conditions, such as with HOBT, EDC, and DIEA in a solvent, such as $CH_2Cl_2$, and reacted at RT, to afford the substituted amide 3. The acids 1 are commercially available or may be prepared by literature methods (for example by the method described by Dieter et. al. *Liebigs Annalen/Recueil* 4, 699-706; 1997). Similarly, substituted amine 2 are either commercially available, can be prepared via literature methods, or may be prepared following literature methods described for analogous compounds. Some of these methods are illustrated in the subsequent schemes. Alternatively, substituted amide 3 is an intermediate to the compounds of Formula I. Protected acetamide 3 is deprotected and reacted with an active sulfonyl compound, such as a substituted sulfonyl chloride, in the presence of base, preferably an organic base such as DIEA, in a solvent such as $CH_2Cl_2$ to form the substituted sulfonyl compounds 4.

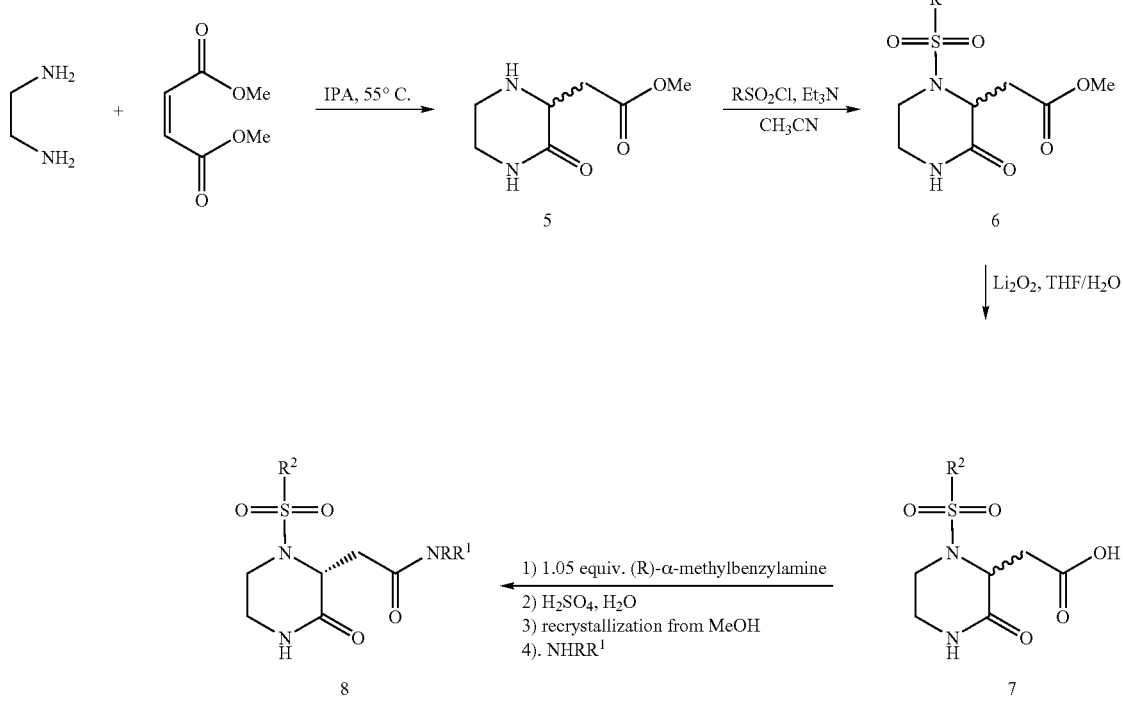

Compounds of Formula III may be prepared as described in Scheme 2.

Piperazinyl esters 5 may be prepared by reacting ethylenediamines with maleate diesters suche as dimethyl maleate, the resulting esters are coupled with an active sulfonyl compound, such as a substituted sulfonyl chloride, in the presence of base, preferably an organic base such as DIEA, in a solvent such as $CH_3CN$ or $CH_2Cl_2$ to form the substituted sulfonyl piperazinyl ester 6. After hydrolysis, substituted sulfonyl piperazinyl racemic ester 7, ,may be resolved in to its R or S enantimer using a chiral amine such (R)-α-methylbenzylamine as a resolving agent. Following an acid mediated salt break, the resulting enantiomerically pure acid is reacted with the $HNRR^1$ using standard peptide coupling conditions, such as with HOBT, EDC, and DIEA in a solvent, such as $CH_2Cl_2$, and reacted at RT, to afford the substituted amide 8. The reaction is kept at a temperature above about 0° C., preferably at about RT, to yield the compound of Formula III. In this manner, either racemic, or R or S antipodes of the compounds of Formula III may be prepared from racemic or R or S compound 8.

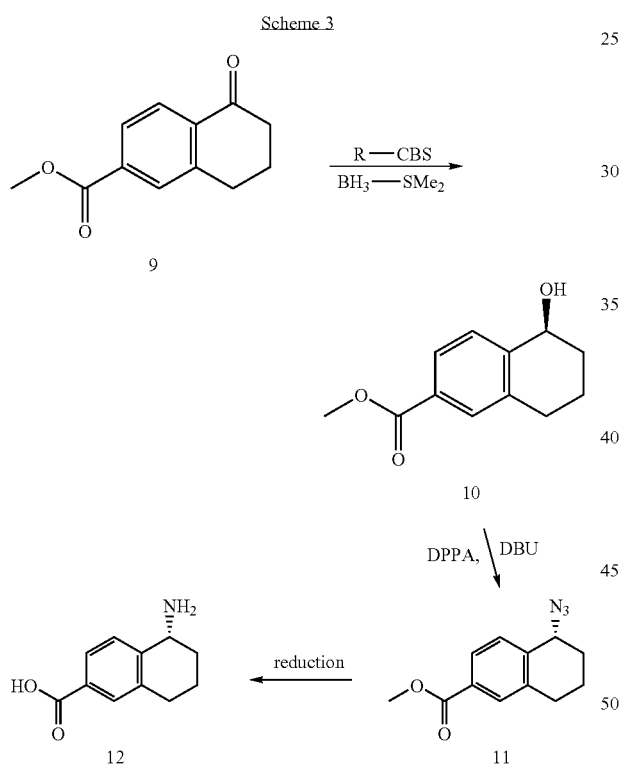

(5(R)-Amino-5,6,7,8-tetrahydro-naphthalen-2-yl)-methanol is prepared by the method described in Scheme 3. (R)-methyl CBS oxazaborolidine (in dry solvent such as toluene or dichloromethane) is treated with borane methyl sulfide complex and 5-oxo-5,6,7,8-tetrahydro-naphthalene-2-carboxylic acid methyl ester(9). The reaction is kept at a temperature below RT, preferably below about 0° C., more preferably at about −10° C., to provide the alcohol 10. The azide 10 is formed from the alcohol 11, such as by treatment with DPPA and DBU, at a temperature above about 0° C., preferably at about RT.

Reduction of the azide 11, such as with LAH, at a temperature above about 0° C., preferably at about RT provides the methanol 12. Similarly (4-(R)-amino-chroman-7-yl)-methanol and (1-(R)-amino-indan-5-yl)-methanol can be prepared.

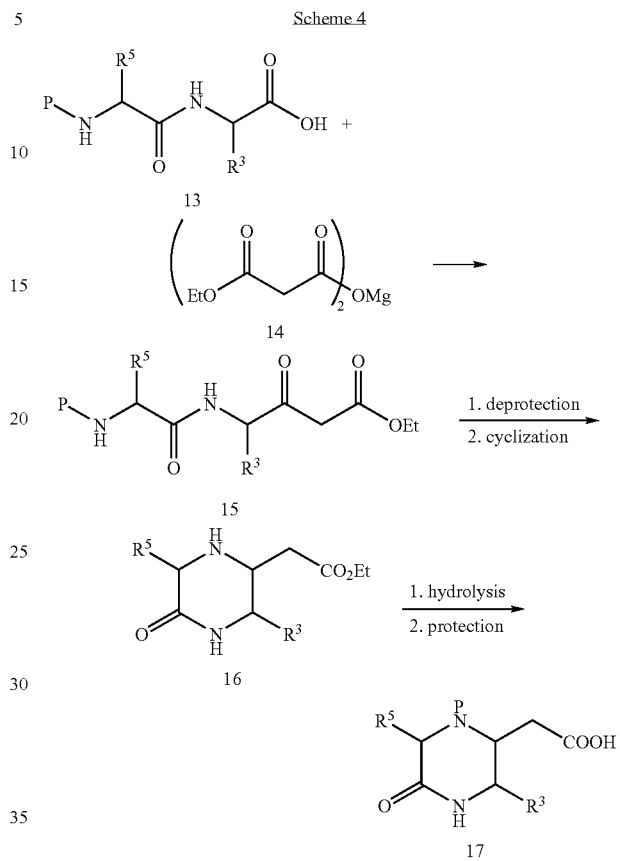

(5-Oxo-piperazin-2-yl)-acetic acids (where $R^4$ and $R^4A$ together form oxo) may be prepared in a convergent manner as described in Scheme 4. Acids 13, protected for example with a CBZ group, are homologated with magnesium monomethylmalonate to afford the protected ester 15. The acids 12 are commercially available or may be prepared by literature methods (for example by the method described by Patino-Molina, R. Tetrahedron (1999) 55, 15001. Similarly, magnesium monomethylmalonate 14 may be prepared following literature methods described in Reetz, M. T., J. Angew. Chem. Int. Ed. Eng. (1979) 18, 72. The protected ester 15 is deprotected, such as via hydrogenation for a CBZ group, which in turn can be reacted with $ZnCl_2$ to form the imine that can be reduced, such as with $NaBH_3CN$, to yield the 5-oxopiperazin-2-yl ester 16. Hydrolysis of the ester following common literature conditions followed by protection of the amine forms the acid 17.

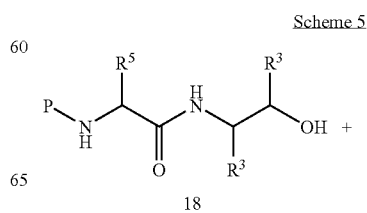

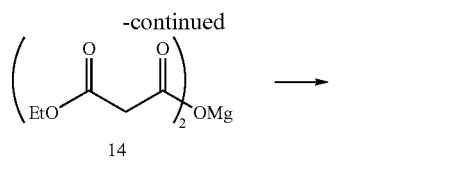

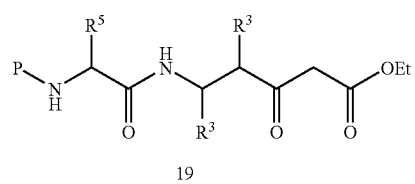

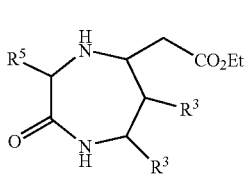

(2-Oxo-[1,4]diazepan-5-yl)-acetic acid esters (where $R^4$ and $R^{4A}$ together form oxo and t is 2) may be prepared in a manner similar to that described in Scheme 4 to give the 7 membered version 20.

Scheme 6

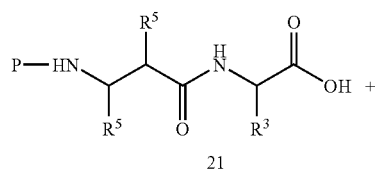

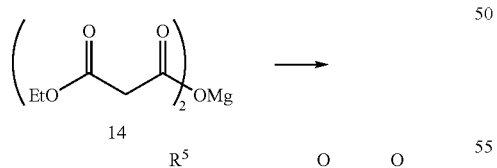

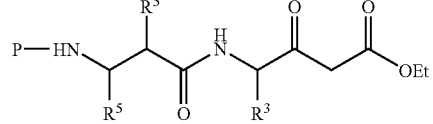

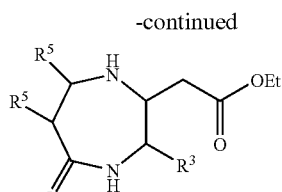

5-Oxo-[1,4]diazepan-2-yl)-acetic acid esters (where $R^4$ and $R^{4A}$ together form oxo and q is 2) may be prepared in a manner similar to that described in Scheme 4 to give a 7 membered version 23.

Scheme 7

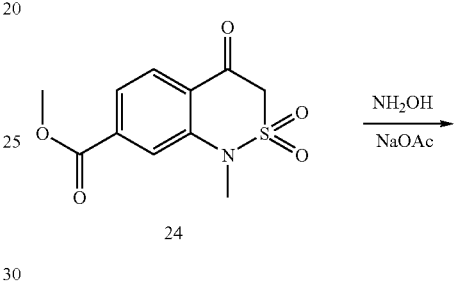

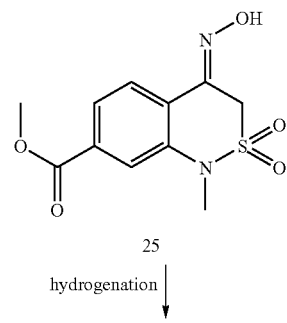

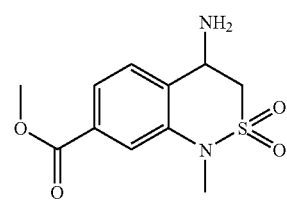

Amino compounds 26 are prepared from the corresponding ketones 24 by the method described in Scheme 7. Treatment of the ketones 24 with hydroxylamine in a solvent such as NaOAc, at a temperature above RT, preferably above about 75° C., even more preferably at reflux, provides the oxime 25. Hydrogenation of the oxime 25, such as in the presence of a catalyst such as Pd/C, provides the amine 26.

Scheme 8
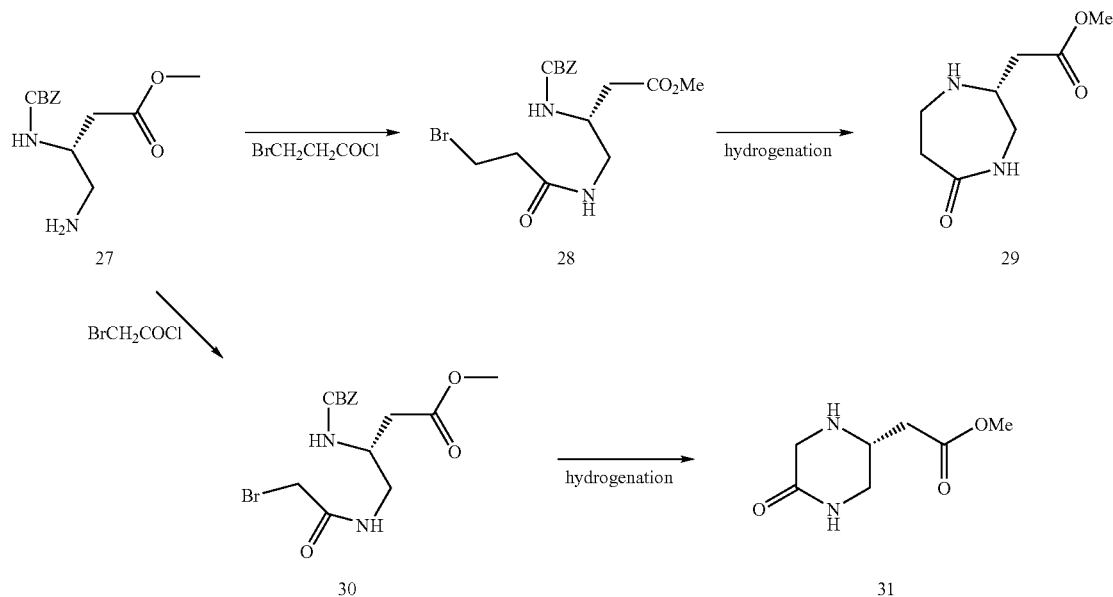
Alternatively, (5-oxo-[1,4]diazepan-2-yl)-acetic acid esters (where $R^4$ and $R^{4,4}$ together form oxo and q is 2) 29 and (5-oxo-piperazin-2-yl)-acetic acid esters (where $R^4$ and $R^{4,4}$ together form oxo and q is 1) 31 can be synthesized enatioselectively from chiral 3,4-diaminobuytric acid in a manner similar to that described in Scheme 8.
Scheme 9
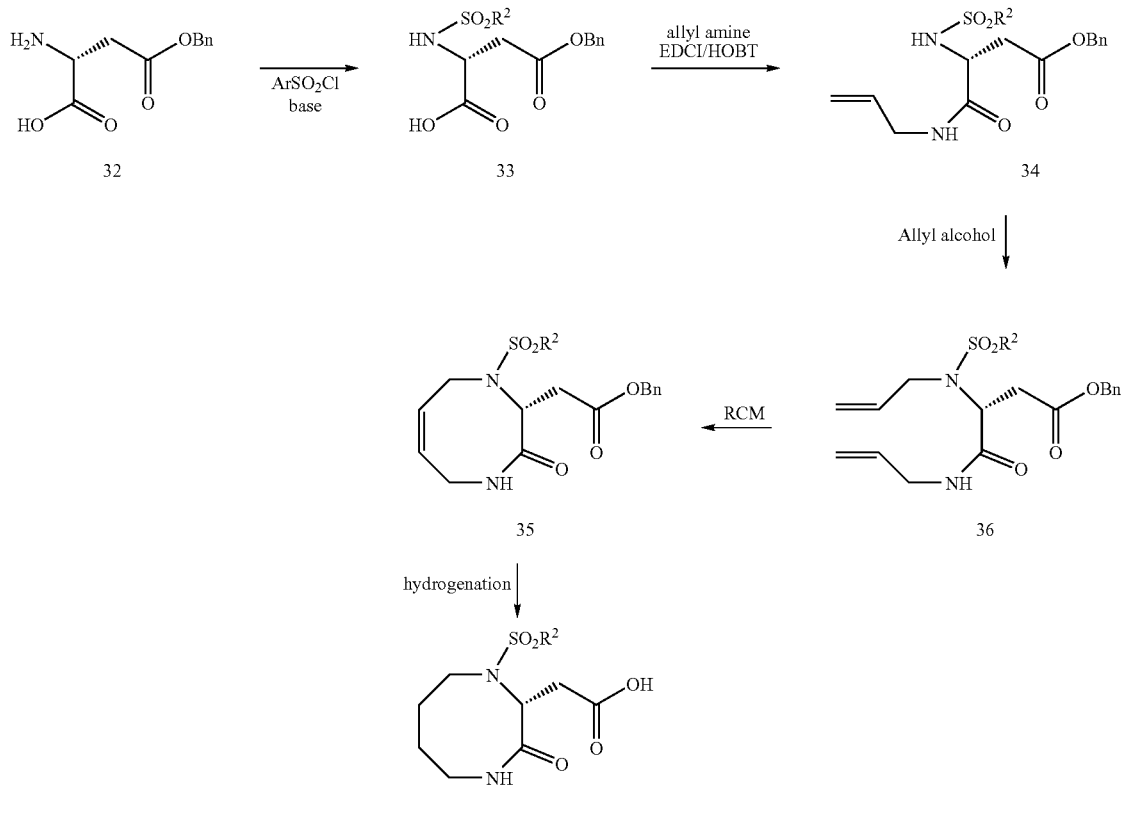

(3-Oxo-[1,4]diazocan-2-yl)-acetic acid 36 (where $R^3$ and $R^{3,4}$ together form oxo, where $R^4$ and $R^{4,4}$ are H, and q is 3) can be synthesized enatio-selectively from chiral 2-amino-succinic acid 4-benzyl ester 32 in a manner similar to that described in Scheme 9 utilizing ring closing metathesis (RCM) to give 8-membered versions 37. The RCM step is as described by J. Reichwein, et al. J. Angew. Chem. Int. Ed. 1999, 38, 3684-3687.

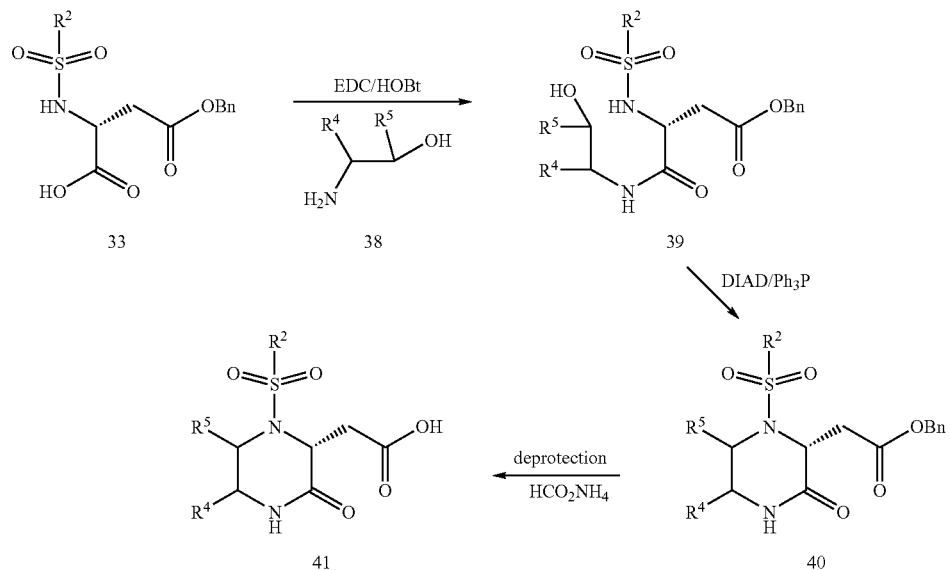

Scheme 10

Similarly, (3-oxo-piperazin-2-yl)-acetic acid 41 (where $R^3$ and $R^{3,4}$ together form oxo, and q is 1) can be synthesized enatioselectively from chiral substituted sulfonylamino-succinic acid 4-benzyl ester in a manner similar to that described in Scheme 10 utilizing Mitsunobu alkylation ring closure to give 6-membered versions 41. The Mitsunobu alkylation step is as described by S. Pikul, et al. Bioorg. Med. Chem. Lett. (2001), 11:1009-1013.

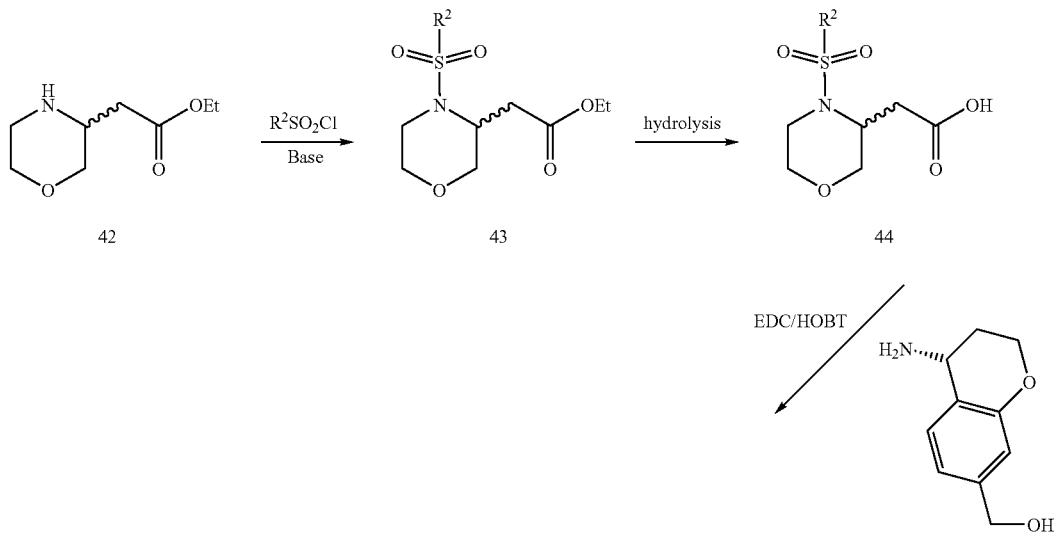

Scheme 11

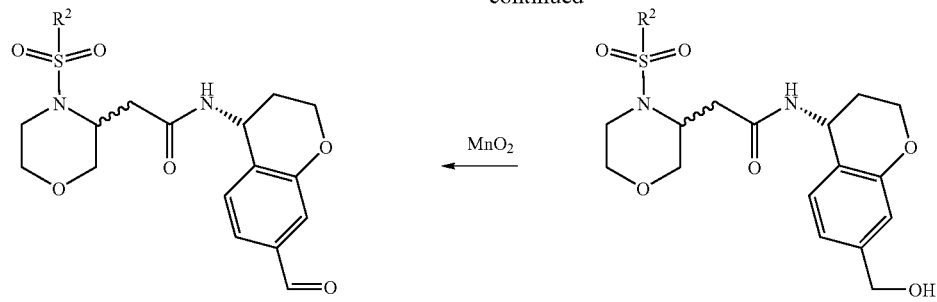
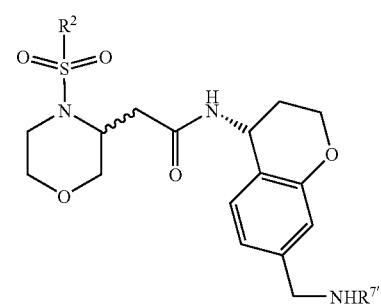
Compounds of Formula 147 (where X is O) may be prepared in a convergent manner as described in Scheme 1. See H. Fukawa et al., Chem. Pharm. Bull. (1983) 31:94-99 for preparation of ester 42.
Scheme 12
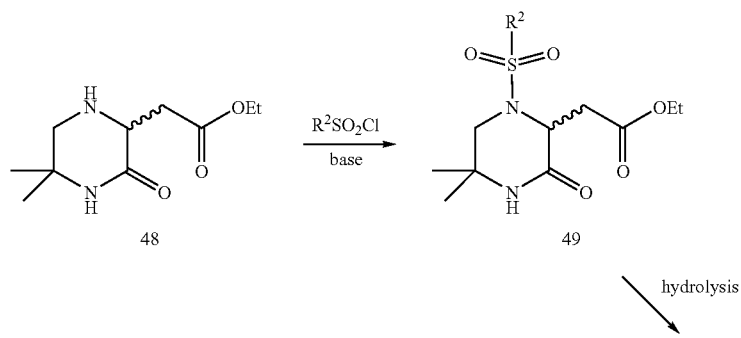

-continued

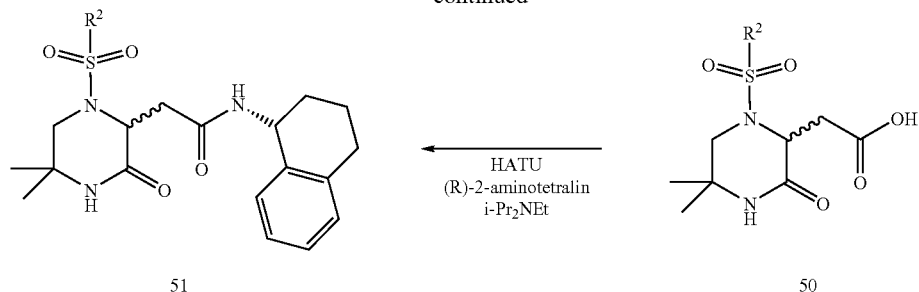

Compounds 51 (where $R^3$ and $R^{3A}$ together form oxo, where $R^4$ and $R^{4A}$ are both methyl and q is 1) may be prepared as described in Scheme 12, similar to that described in Scheme 2. (5,5-Dimethyl-3-oxo-piperazin-2-yl)-acetic acid ethyl ester 48 is prepared according to the procedure of Dutta and Foye (J. Pharmaceutical Science (1990) 79:447-452). Treatment of 48 with sulfonyl chlorides in the presence of base such as $Na_2CO_3$ or TEA, in organic solvents such as $CH_3CN$ or $CH_2Cl_2$, at a temperature of about RT to about 80° C. yielded sulfonamides 49. Hydrolysis to the acid in the presence of bases such as LiOH or NaOH, in the aqueous solvent such as MeOH and THF at a temperature of about 0° C. to about RT forms the acids 50. The acid 50 is coupled with appropriate amines using coupling agents HOBt/EDCI or HATU with or without organic bases such as TEA or DIEA at a temperature of about 0° C. to about RT provides compounds 51.

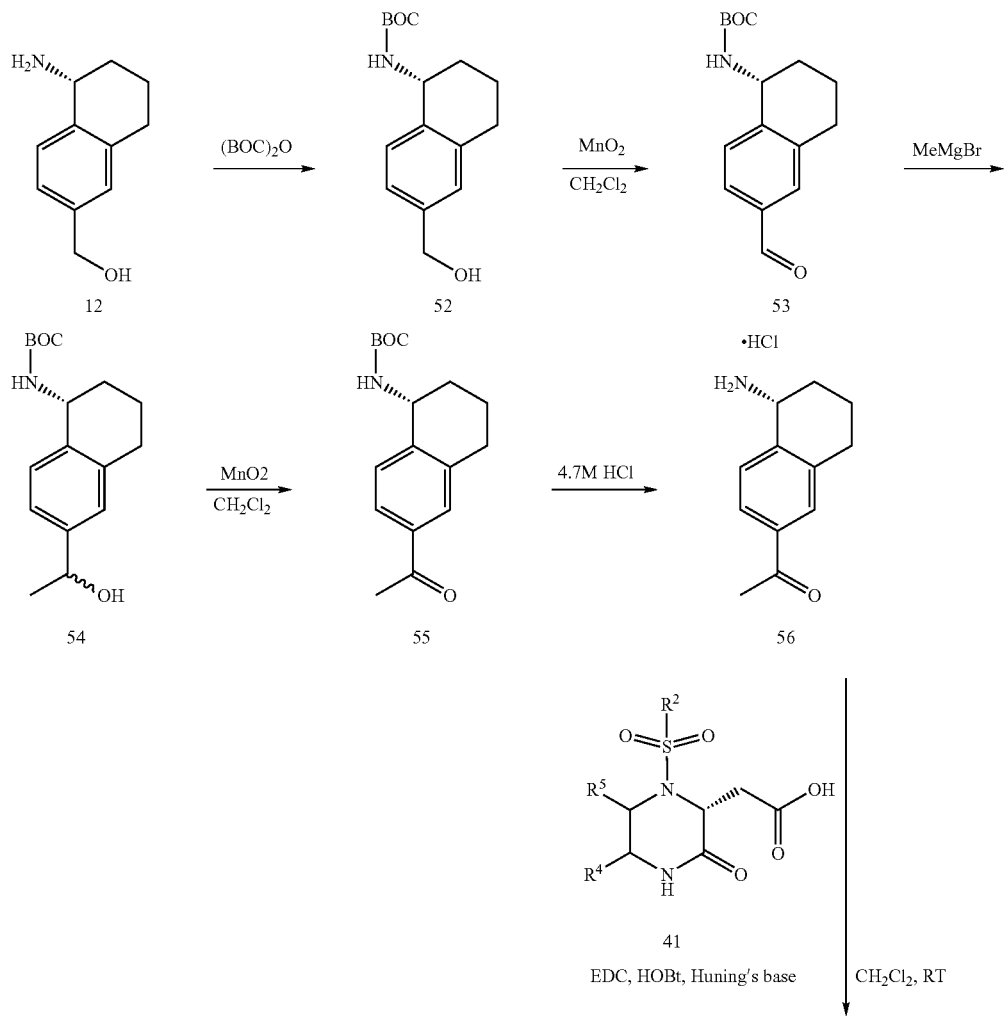

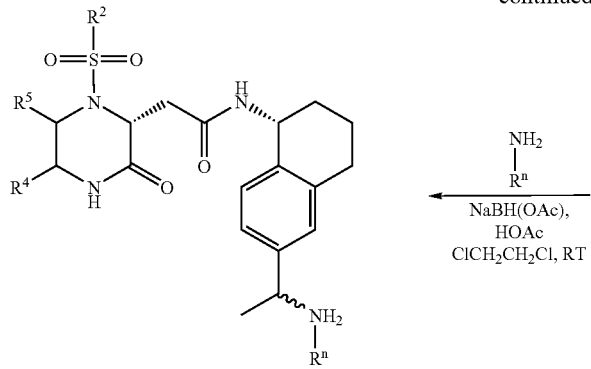

58

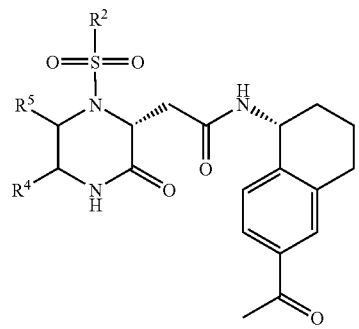

57

Additional analogs of compounds of Formula II may be prepared as illustrated in Schemes 13-15. Following Boc protection, amino alcohol 12 is converted to its methyl ketone 55 by the three step procedure depicted in Scheme 13. Protected 1-amino-6-hydroxymethyl-1,2,3,4-tetrahydro-naphthalene 52 is oxidized, such as with $MnO_2$ in an organic solvent, such as $CH_2Cl_2$, preferably at a temperature of about RT, to form the aldehyde 53. The aldehyde is alkylated, such as with a Grignard reagent in a solvent such as THF, at a temperature initially below RT, preferably about $-30°$ C. and more preferably at about $-78°$ C., then at about RT, to form the alcohol 54. The alcohol 54 is oxidized, such as with $MnO_2$ as previously described, to form the protected ketone 55. The resulting ketone 56 is deprotected such as with HCl, and converted to compound 57 similar to the method described in Scheme 11.

-continued

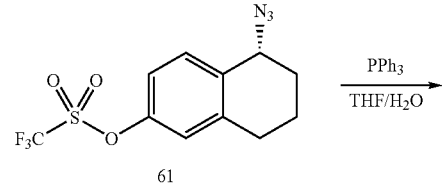

61

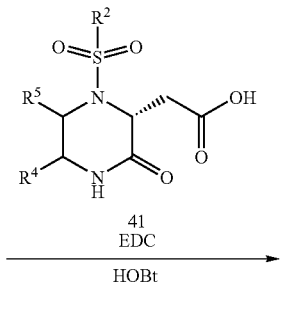

62

Scheme 14

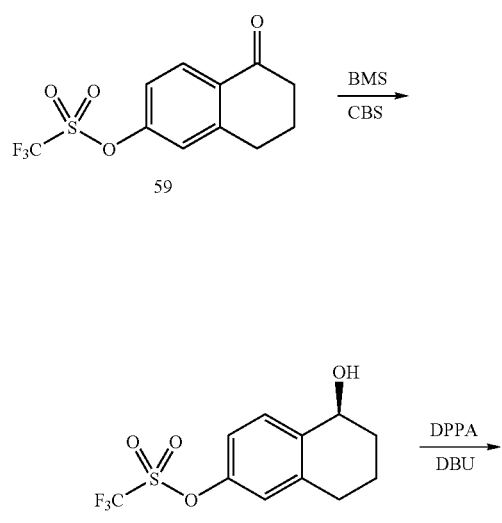

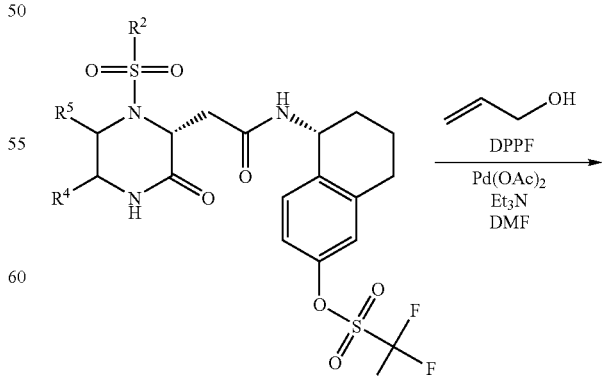

63

-continued

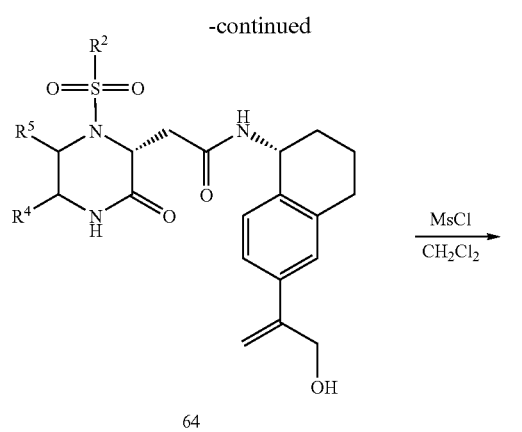

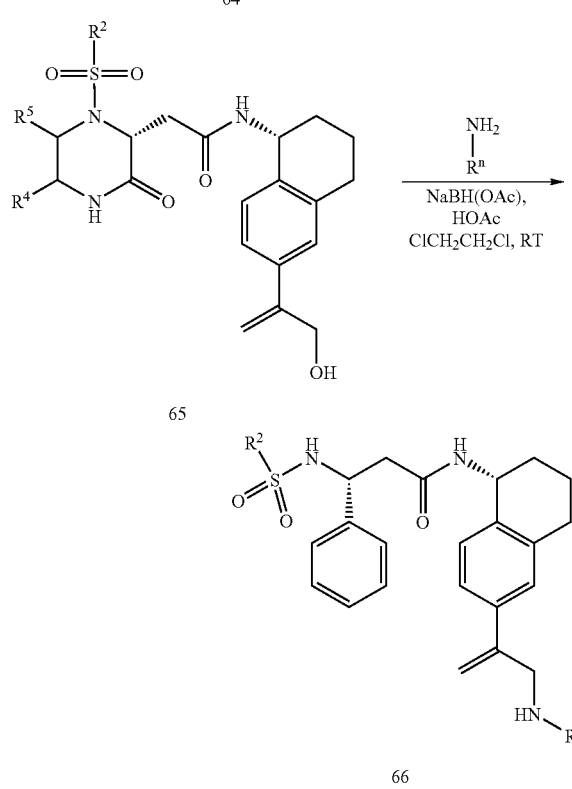

Vinyl amine derivatives of compounds of Formula II may be prepared by the methods illustrated in Scheme 14. The 6-hydroxy-1-tetralone was reacted with triflic anhydride and the temperature was preferably maintained between 0 C and RT, to form triflate 59. Treatment of the triflate 59 with (R)-2-methyl-CBS-oxazaborolidine and BMS and trifluoromethanesulfonic acid at a temperature between 0 C and RT, provides the alcohol 60. Alcohol 60 was converted to the azide by addition of DBU and dppa, at a temperature between 0° C. and RT. Addition of PPh$_3$ to the azide 61 provides the amine 62, which can be coupled, as described above, with the appropriate acid to form amide 63. Reaction with the amide 62 palladium(II)acetate, dppf, base (e.g. Et$_3$N) and allyl alcohol, heated to a temperature above RT, preferably between about 50° C. and about 100° C., more preferably at about 80° C. provides the vinyl alcohol 64. Treatment of the 1-hydroxymethyl-vinyl compound 64 with methanesulfonyl chloride provides mesyl derivative 65, which upon treatment with an amine, such as pyrrolidine, provides the vinyl amine 66.

Following the protocols illustrated in Schemes 15 and 16, the tether length for all of the amino compounds of Formulas I and II may be varied from 1-4 carbons. The protected alcohol 52 can be activated such as by reaction with methane sulfonyl chloride. The resulting mesylate 67 may be reacted with the lithiated dithiane reagent 68 to afford the protected aldehyde 69. Following removal of the Boc protecting group, such as with an ethereal HCl solution or trifluroacetic acid at a temperature between 0° C. and 25° C., the resulting amine is coupled to an acid 41 to afford 70. The latent aldehyde functionality is unmasked by reaction with Hg(ClO$_4$)$_2$ in a solvent such as ethanol, and the resulting aldehyde 71 is converted to compounds of Formula I by reacting with primary or secondary amines using the reductive amination conditions described previously. Compounds with 3 carbon tethers are prepared by the method described in Scheme 17. The cyano-vinyl compound 73 is prepared via treatment of the aldehyde 53 with diethyl cyanophosphate and sodium bis(trimethylsilyl)amide at a temperature between about –78° C. and RT. Deprotection yields the free amine 74 which can be coupled as described above, to provide the intermediate 75. Reduction, such as with Pt catalyzed treatment with H$_2$ yields the aminopropyl compound 76 of the present invention, which may be further elaborated by alkylation of the resulting primary amines using well-known methods.

Scheme 15

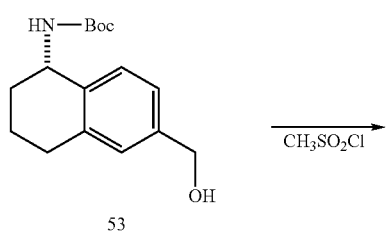

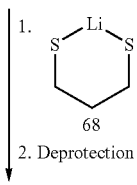

-continued
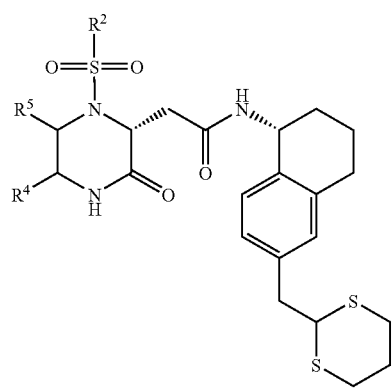
70
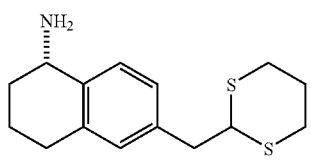
69
Hg(ClO$_4$)$_2$, CaCO$_3$
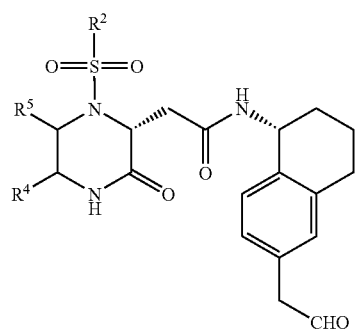
71
NHR$^n$ →
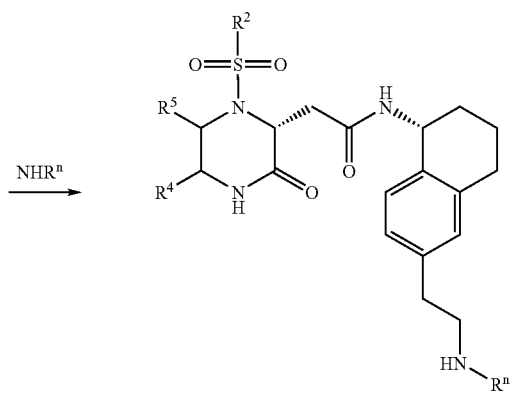
72
Scheme 16
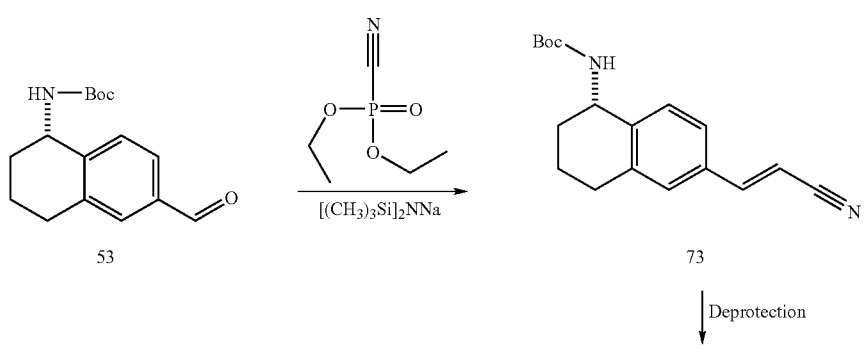
Deprotection

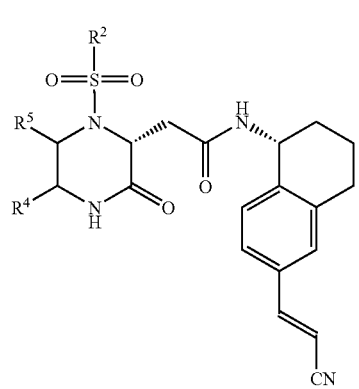

75

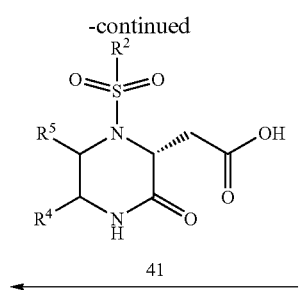

41

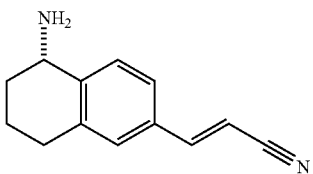

74

Reduction ↓

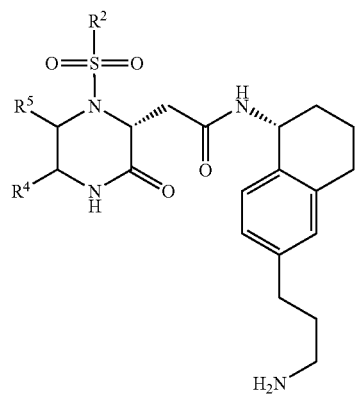

76

Alkylation →

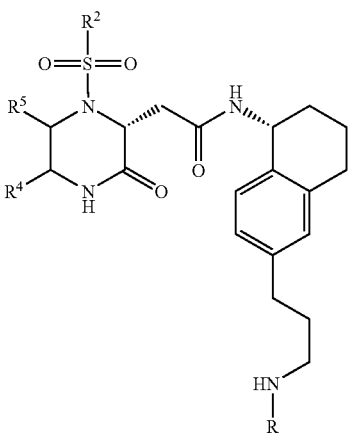

77

The aldehyde 53 can be converted to the carbonitrile 73 such as with treatment with P(Ph)$_3$, DEAD and acetone cyanohydrin. The nitrile 74 can be coupled with the acid, such as with HATU, EDC and DIEA. The (7-cyanomethyl-4-tetralin 75 is hydrogenated, such as with palladium catalyst in an alcohol, e.g. MeOH, to form the alkyl amine 76 of the present invention. The alkyl amine can be substituted using standard methods to make the substituted amines 77 (where R″ is alkyl, substituted alkyl, and the like).

Scheme 17

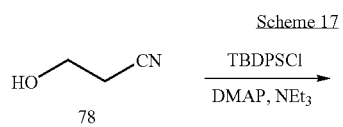

78

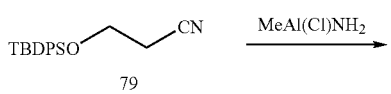

79

-continued

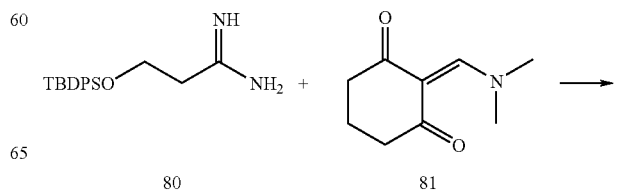

80            81

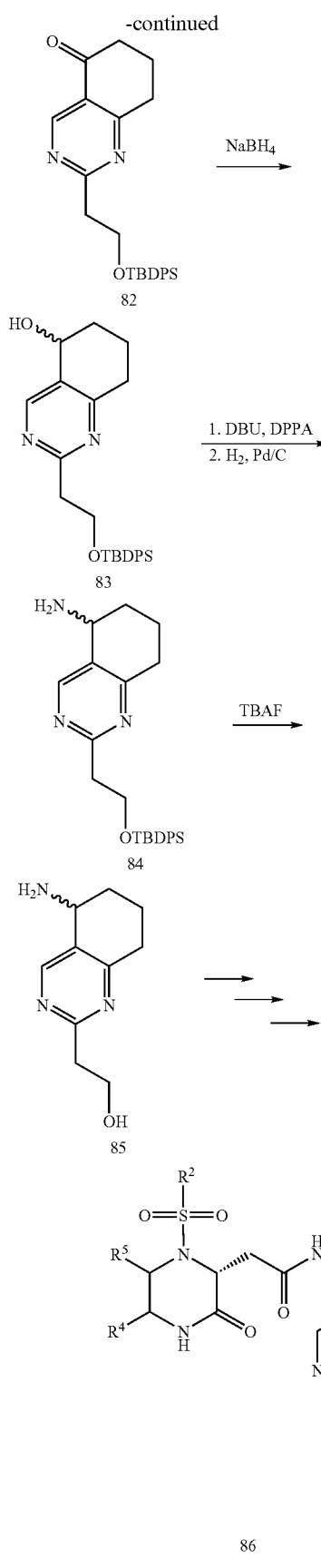

Methods for preparing additional compounds of Formulas I and II are illustrated in Schemes 18-20. The cyano alcohol 78 can be treated with DMAP, base (e.g. NEt$_3$), and PBDPSCl to form the protected alcohol 79. The protected alcohol 79 is aminated, such as with Me$_3$Al, at a temperature below RT and preferably at about 0 C, to yield the amidine 80. Formation of the 5,6,7,8-tetrahydro-quinazolone 82 is achieved such as by reaction of amidine 80 and 2-dimethylaminomethylene-cyclohexane-1,3-dione 81 at a temperature above RT, preferably above about 50 C and more preferably at about 80 C. 5,6,7,8-tetrahydro-quinazolone 82 is reduced such as with NaBH$_4$ to give the alcohol 83. The alcohol 83 is treated with DPPA and DBU to form the azide derivative which is reduced to form the amine 84. The amine 84 is deprotected, such as with TBAF to form the desired intermediate 85, which is converted to compounds 86 of Formula I using methods similar to those described above.

Tetrahydroindazole analogs of Formula I may be prepared as depicted in Scheme 18. Hydroxyethyl hydrazine 87 is reacted with 2-dimethylamino-methylene-cyclohexane-1,3-dione 81 at a temperature between 0 and 25° C. to afford the hydroxyl ketone 87 in high yield. Following protection of the hydroxyl moiety with a silyl protecting group such as TBS, the ketone is reduced and the resulting alcohol carried on to compounds of Formula I using methods previously described in this invention.

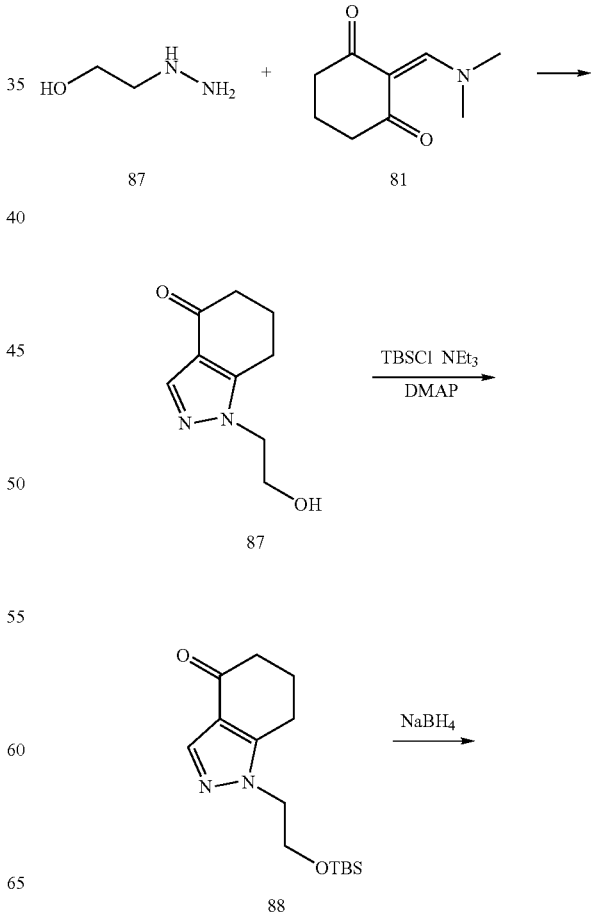

Scheme 18

-continued

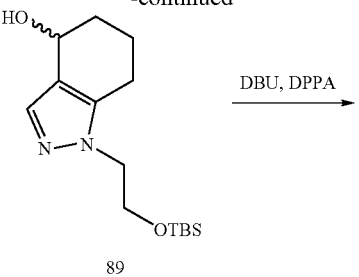
89

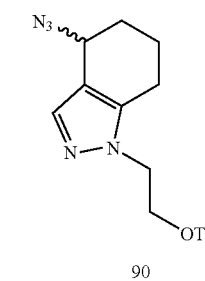
90

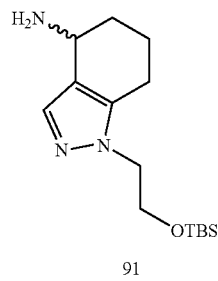
91

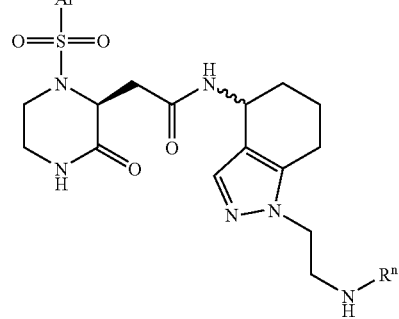
92

Additional compounds of the present invention are depicted in Schemes 19 and 20 and may be prepared by Palladium mediated cross coupling reactions on the aryl triflate or similar aryl halides. For example, aryl trifilate 63 is reacted with the boronic acid 93 to afford the protected amine 94. Following deprotection, the resulting amine is converted to compounds 96 by reductive alkylation with aldehydes or ketones. In addition to the vinal boronic acid 93 illustrated in the above example, a variety of commercially available or readily synthesized boronic acids or boronate esters may be used to to make similar alkyl, or biaryl analogs. In addition, terminal alkynes or alkenes may be used is similar palladium mediated cross coupling reactions as illustrated in Scheme 20.

Scheme 19

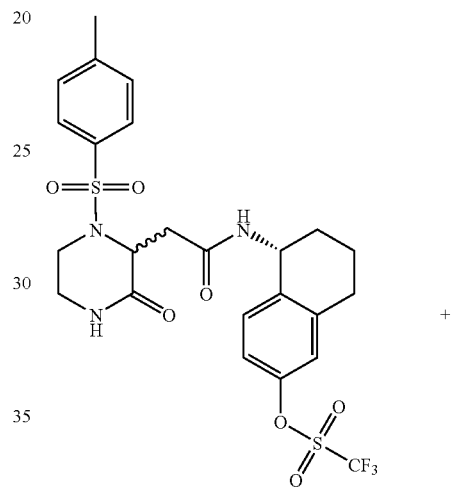

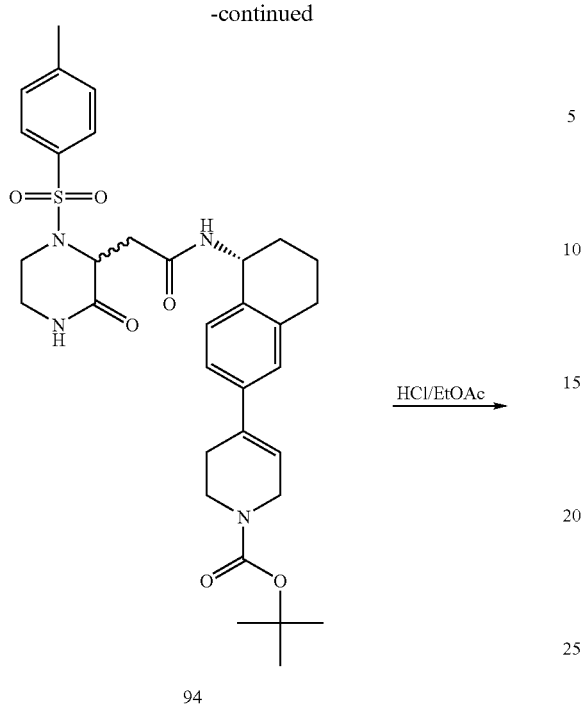

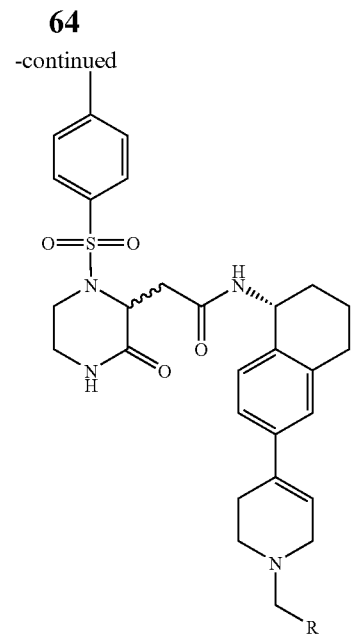

Compounds of the invention can be prepared as described in Scheme 20. The protected amino bicyclic compound 97 was treated with is alkylated, such as with vinyltributyltin in the presence of PPh$_3$, a base such as Et$_3$N and a palladium catalyst, e.g. Pd$_2$(dba)$_3$. The reaction is maintained at a temperature above RT, preferably in a range between about 50 C and about 100 C, more preferably at about 80 C, more preferably in a microwave. After deprotection, such as with TFA in the case the amine is BOC protected, the free amine 99b can be coupled as described above. Oxidation of the vinyl compound 101, such as with OsO4 produces aldehyde 102. Reductive amination, such as with NaHB(OAc)$_3$ in the presence of an amine provides compounds 103.

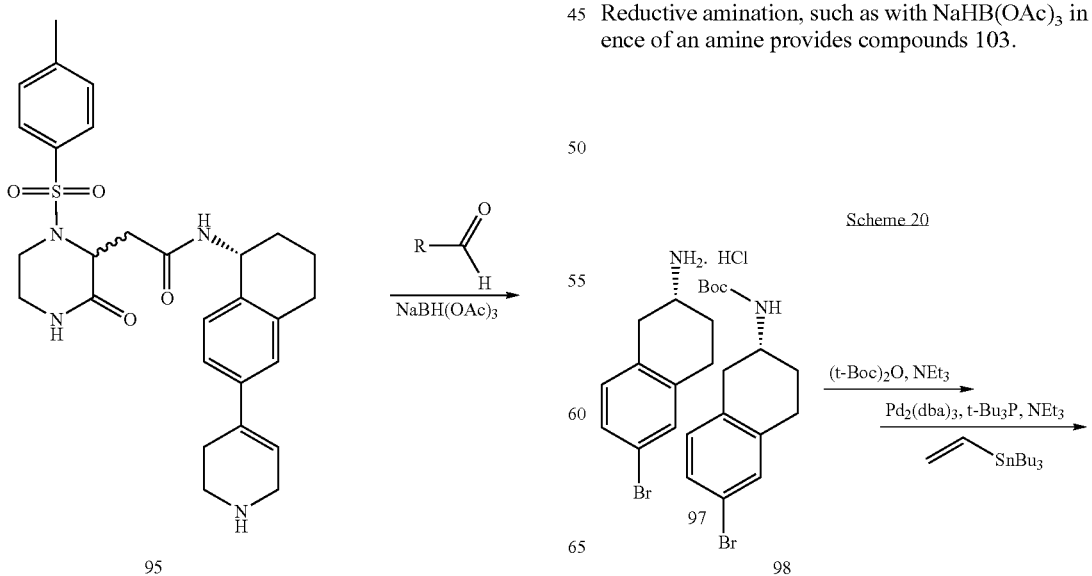

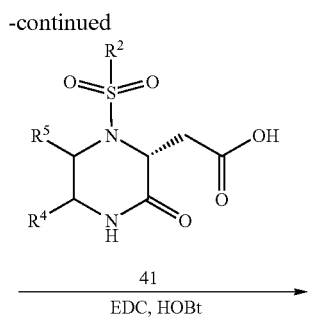

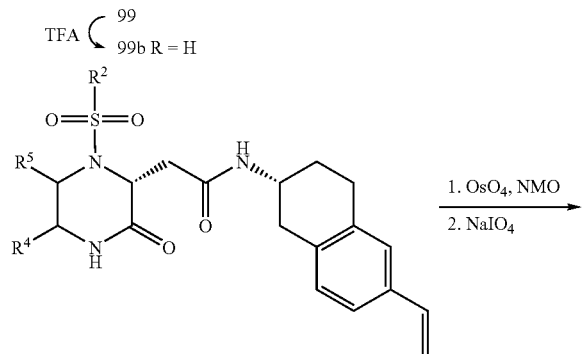

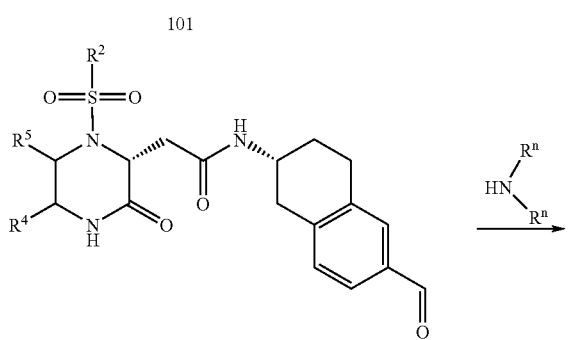

Additional analogs of any of the templates in described in Schemes 1-20 may be prepared using the procedures analogous to those described for above and illustrated in the examples below. In addition elaboration of all intermediates in the above schemes to compounds of Formula I may be accomplished using known by those skilled in the arts of organic and medicinal chemistry.

If one or more other functional groups, for example carboxy, hydroxy, amino, or mercapto, are or need to be protected in a compound of Formulas I-VI, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. McOmie, "Protective Groups in Organic Chemistry", Plenum Press, London and New York (1973); in T. Greene, "Protective Groups in Organic Synthesis", Wiley, New York (1981); in "The Peptides", Volume 3 (eds: E. Gross and J. Meienhofer), Academic Press, London and New York (1981); in "Methoden der organischen Chemie" (Methods of organic chemistry), Houben Weyl, 4th edition, Volume 15/1, Georg Thieme Verlag, Stuttgart (1974); in H. Jakubke and H. Jescheit, "Aminosäiuren, Peptide, Proteine" (Amino acids, peptides, proteins), Verlag Chemie, Weinheim, Deerfield Beach, and Basel (1982); and in Jochen Lehmann, "Chemie der Kohlenhydrate: Monosaccharide und Derivate" (Chemistry of carbohydrates: monosaccharides and derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130-170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150°

C., for example at about −80° C. to about 60° C., at RT, at about −20° C. to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, H₂O, esters, typically lower alkyl-lower alkanoates, e.g. EtOAc, ethers, typically aliphatic ethers, e.g. Et₂O, or cyclic ethers, e.g. THF, liquid aromatic hydrocarbons, typically benzene or toluene, alcohols, typically MeOH, EtOH or 1-propanol, IPA, nitriles, typically CH₃CN, halogenated hydrocarbons, typically CH₂Cl₂, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I-VI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I-VI. These detailed descriptions fall within the scope, and serve to exemplify, the above-described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

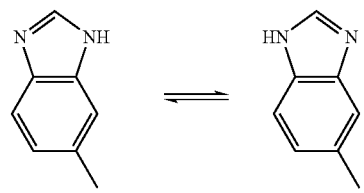

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, K₂CO₃, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. Greene and P. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

The following examples contain detailed descriptions of the methods of preparation of compounds of Formulas I-VI. These detailed descriptions fall within the scope, and serve to exemplify, the above-described General Synthetic Procedures which form part of the invention. These detailed descriptions are presented for illustrative purposes only and are not intended as a restriction on the scope of the invention.

The following abbreviations are used:
AcOH, HOAc—acetic acid
$CH_3CN$—acetonitrile
$NH_3$—ammonia
$NH_4Cl$—ammonium chloride
$NH_4OH$—ammonium hydroxide
HATU—O-(7-Azabenzotriazol-1-yl)-N,N,N',N'-tetramethyluronium hexafluorophosphate
AIBN—2,2'-azobisisobutyronitrile
$(PPh_3)_2NiBr_2$ bis(triphenylphosphine)nickel(II) bromide
$BH_3$—borane
$BH_3SMe_2$—borane-methyl sulfide complex
$Br_2$—bromine
NBS—N-bromosuccinimide
$CCl_4$—carbon tetrachloride
$CHCl_3$—chloroform
CBS—4-cyanobenzoic acid
DBU—1,8-diazabicyclo[5.4.0]undec-7-ene
$CH_2Cl_2$—dichloromethane
$Et_2O$—diethyl ether
Ip2NEt, DIEA diisopropylethylamine
$Me_2NH$—dimethylamine
EDC—(3-dimethylamino-propyl)-ethyl-carbodiimide-HCl salt
DMAP—4-(dimethylamino)pyridine
DMF—dimethylformamide
DMSO—dimethyl sulfoxide (also known as methyl sulfoxide)
DPPA—diphenylphosphoryl azide
EtOH—ethanol
EtOAc—ethyl acetate
$HCO_2H$—formic acid
g—gram
h—hour
HCl—hydrochloric acid
$H_2$—hydrogen
HOAt—1-hydroxy-7-azabenzotriazole
HOBt—1-hydroxybenzotriazole
IPA—isopropanol
iPrOH—isopropanol
LAH—lithium aluminum hydride
LDA—lithium diisopropylamide
LiOH—lithium hydroxide
$MgSO_4$—magnesium sulfate
MeOH—methanol
NMM—N-methylmorpholine
NMP—1-methyl-2-pyrrolidone
mL—milliliter
min—minutes
$N_2$—nitrogen
Pd/C—palladium on carbon
$Pd(OH)_2$—palladium hydroxide
$H_3PO_4$—phosphoric acid
$K_2CO_3$—potassium carbonate
KCN—potassium cyanide
KOH—potassium hydroxide
RT—room temperature
$SiO_2$—silica
NaOAc—sodium acetate
$NaN_3$—sodium azide
$NaHCO_3$—sodium bicarbonate
$NaBH_4$—sodium borohydride
NaOH—sodium hydroxide
$NaBH(OAc)_3$—sodium triacetoxyborohydride
$H_2SO_4$—sulfuric acid
$SOCl_2$—thionyl chloride
THF—tetrahydrofuran
TsCl—tosyl chloride
TsOH—toluene sulfonic acid
TEA, $Et_3N$—triethylamine
TFA—trifluoroacetic acid
$PPh_3$—triphenylphosphine
$H_2O$—water Unless otherwise noted, all materials were obtained from commercial suppliers and used without further purification. All parts are by weight unless otherwise indicated. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at RT.

Preparation I—chroman-4-one oxime To a mixture of 4-chromanone (10.00 g, 67.50 mmol) and hydroxylamine hydrochloride (7.04 g, 101 mmol) in EtOH (100 mL) was added a solution of NaOAc (16.61 g, 202.5 mmol) in $H_2O$ (30 mL). The reaction was heated to reflux for 2 h. The mixture was cooled to RT and concentrated in vacuo. The residue was diluted with $H_2O$ and acidified with 1N HCl. The aqueous mixture was extracted with EtOAc until TLC analysis showed no evidence of title compound in the aqueous layer. The combined organics were dried with $MgSO_4$ and concentrated in vacuo to furnish the crude title compound which was used without further purification. MS (APCI pos) 164 (M+H).

Preparation II—chroman-4-ylamine
LAH (6.35 g, 167 mmol) was suspended in THF (100 mL) at 0° C. A solution of chroman-4-one oxime (10.92 g, 66.92 mmol) in THF (100 mL) was added drop-wise. The mixture was heated slowly to reflux for 4 h. The reaction was cooled to RT and added drop-wise to a stirred saturated solution of Rochelle's salt in $H_2O$. The bi-phasic mixture was stirred rapidly at RT for 1 h. The layers were separated and the aqueous layer was extracted with EtOAc until TLC analysis of the aqueous layer showed no evidence of the title compound. The combined organics were dried over MgSO$_4$ and concentrated in vacuo to furnish the crude material, which was purified by flash column chromatography to afford the title compound. MS (APCI pos) 150 (M+H).

Preparation III—6-bromo-chroman-4-ylamine

A solution of chroman-4-ylamine (2.550 g, 17.09 mmol) in AcOH (50 mL) at RT was treated with Br$_2$ (3.01 g, 0.96 mL, 18.8 mmol) drop-wise. The reaction was stirred at RT until HPLC analysis showed complete consumption of starting material. The mixture was diluted with H$_2$O (100 mL) and NaOH was added until the solution became basic. The aqueous layer was extracted with EtOAc until TLC analysis of the aqueous layer showed no evidence of the title compound. The combined organics were dried over MgSO$_4$ and concentrated in vacuo to yield the crude compound, which was purified by flash column chromatography to afford the pure title compound. MS (APCI pos) 229 (M+H).

Preparation IV—(6-bromo-chroman-4-yl)-carbamic acid tert-butyl ester

To a RT solution of 6-bromo-chroman-4-ylamine (2.270 g, 9.952 mmol) and di-tert-butyl dicarbonate (2.606 g, 11.94 mmol) in CH$_2$Cl$_2$ (50 mL) was added a solution of NaHCO$_3$ (1.672 g, 19.90 mmol) in H$_2$O (50 mL). The bi-phasic mixture was rapidly stirred until complete consumption of starting material was observed by HPLC analysis (overnight). The reaction was diluted with EtOAc and H$_2$O and the layers were separated. The organics were dried with MgSO$_4$ and concentrated in vacuo to afford the crude title compound, which was used without further purification.

Preparation V—(6-formyl-chroman-4-yl)-carbamic acid tert-butyl ester (6-Bromo-chroman-4-yl)-carbamic acid tert-butyl ester (3.859 g, 11.76 mmol) was dissolved in THF (50 mL) and cooled to −78° C. n-Butyllithium (2.5 M) (11.76 mL, 29.40 mmol) was added drop-wise to the stirred solution. The reaction was stirred at −78° C. for 30 min and DMF (4.55 mL, 58.8 mmol) was added drop-wise and the system was slowly warmed to RT overnight. The reaction was quenched with saturated aqueous NH$_4$Cl solution and extracted with EtOAc. The combined organics were dried with MgSO$_4$ and concentrated in vacuo to afford the crude, which was purified by flash column chromatography to furnish the pure title compound.

Preparation VI—6-bromo-3,4-dihydro-1H-naphthalen-2-one oxime

To a mixture of 6-bromo-3,4-dihydro-1H-naphthalen-2-one (5.370 g, 23.86 mmol) and hydroxylamine hydrochloride (2.487 g, 35.79 mmol) in EtOH (80 mL) was added a solution of NaOAc (5.871 g, 71.57 mmol) in H$_2$O (20 mL). The mixture was heated to reflux for 2 h. The reaction was cooled to RT and concentrated in vacuo. The residue was suspended in H$_2$O and filtered. The pad was washed with H$_2$O (2×50 mL) and Et$_2$O (2×50 mL) and the solids were dried in vacuo to furnish the title compound, which was used without further purification.

MS (APCI pos) 242 (M+H).

Preparation VII—6-bromo-1,2,3,4-tetrahydro-naphthalen-2-ylamine

A solution of BH$_3$-THF complex (1 M) (35.9 mL, 35.9 mmol) was added drop-wise to a stirred solution of 6-bromo-3,4-dihydro-1H-naphthalen-2-one oxime (3.450 g, 14.37 mmol) in THF (125 mL) at 0° C. The mixture was warmed to RT and to reflux for 24 h. The reaction was cooled to RT and 1 N aqueous HCl was added carefully until the mixture was acidic and the system was stirred until no further gas was evolved. The solution was made basic by the addition of NaOH and the aqueous layer was extracted with EtOAc. The combined organics were dried over MgSO$_4$ and concentrated in vacuo to afford the crude title compound, which was purified by flash column chromatography to yield the title compound.

MS (APCI pos) 228 (M+H).

Preparation VIII—(6-bromo-1,2,3,4-tetrahydro-naphthalen-2-yl)-carbamic acid tert-butyl ester Di-tert-butyl dicarbonate (1.030 g, 4.719 mmol) was added to a stirred RT solution of 6-bromo-1,2,3,4-tetrahydro-naphthalen-2-ylamine (0.970 g, 4.290 mmol) in CH$_2$Cl$_2$ (100 mL). TEA (0.897 mL, 6.435 mmol) was added to the reaction and the mixture was stirred at RT until HPLC analysis showed complete consumption of starting material. The reaction was diluted with CH$_2$Cl$_2$, washed with saturated aqueous NaHCO$_3$, dried over MgSO$_4$ and concentrated in vacuo to afford the crude material. The crude was purified by flash column chromatography to yield the title compound. MS (APCI pos) 269 (M-t-Bu).

Preparation IX—(6-formyl-1,2,3,4-tetrahydro-naphthalen-2-yl)-carbamic acid tert-butyl ester (6-Bromo-1,2,3,4-tetrahydro-naphthalen-2-yl)-carbamic acid tert-butyl ester (1.080 g, 3.311 mmol) was dissolved in THF (30 mL) and cooled to −78° C. n-Butyllithium (2.5 M) (3.311 mL, 8.276 mmol) was added drop-wise to the stirred solution. The reaction was stirred at −78° C. for 30 min and DMF (1.282 mL, 16.55 mmol) was added drop-wise and the mixture was slowly warmed to RT overnight. The reaction was quenched with saturated aqueous NH$_4$Cl solution and extracted with EtOAc. The combined organics were dried over MgSO$_4$ and concentrated in vacuo to afford the crude material, which was purified by flash column chromatography to furnish the pure title compound. MS (APCI pos) 217 (M-t-Bu).

Preparation X—(6-piperidin-1-ylmethyl-1,2,3,4-tetrahydro-naphthalen-2-yl)-carbamic acid tert-butyl ester (6-Formyl-1,2,3,4-tetrahydro-naphthalen-2-yl)-carbamic acid tert-butyl ester (0.090 g, 0.33 mmol) was dissolved in N,N-dimethylacetamide (10 mL). Piperidine (0.162 mL, 1.63 mmol) was added and the mixture was stirred at RT for 30 min. NaBH(OAc)$_3$ (0.173 g, 0.817 mmol) was added in one portion and the reaction was stirred at RT until complete consumption of starting material was observed by HPLC analysis. The reaction was in concentrated in vacuo and the residue was diluted with CH$_2$Cl$_2$ and H$_2$O and the aqueous layer was made basic with NaOH. The layers were separated and the organics were dried over MgSO$_4$ and concentrated in vacuo to afford the crude title compound, which was used without further purification. MS (APCI pos) 345 (M+H).

Preparation XI—6-piperidin-1-ylmethyl-1,2,3,4-tetrahydro-naphthalen-2-ylamine (6-Piperidin-1-ylmethyl-1,2,3,4-tetrahydro-naphthalen-2-yl)-carbamic acid tert-butyl ester (0.113 g, 0.327 mmol) was suspended in CH$_2$Cl$_2$ (2.5 mL) then TFA was added (2.5 mL). The reaction was stirred at RT until complete consumption of starting material was observed by HPLC analysis (2 h). The reaction mixture was concentrated in vacuo to afford the crude title compound as the bis-TFA salt, which was used without further purification. MS (APCI pos) 245 (M+H).

Preparation XII—4-hydroxyimino-1-methyl-2,2-dioxo-1,2,3,4-tetrahydro-2$\lambda^6$-benzo[c][1,2]thiazine-7-carboxylic acid methyl ester NaOAc (3.66 g, 44.5 mmol) was added to an EtOH (100 mL) solution of 1-methyl-2,2,4-trioxo-1,2,3,4-tetrahydro-2$\lambda^6$-benzo[c][1,2]thiazine-7-carboxylic acid methyl ester (4.00 g, 14.8 mmol) and hydroxylamine hydrochloride (1.55 g, 22.3 mmol). After heating at reflux for 4 days, it was evaporated, diluted with $CH_2Cl_2$ (400 mL), washed with $H_2O$, dried over $MgSO_4$, filtered, and concentrated in vacuo. Crystallization from MeOH provided the title compound. MS (−APCI, m/z): 283 (M−H)$^-$.

Preparation XIII—4-Amino-1-methyl-2,2-dioxo-1,2,3,4-tetrahydro-2$\lambda^6$-benzo[c][1,2]thiazine-7-carboxylic acid methyl ester 4-Hydroxyimino-1-methyl-2,2-dioxo-1,2,3,4-tetrahydro-2$\lambda^6$-benzo[c][1,2]thiazine-7-carboxylic acid methyl ester (1.50 g, 5.28 mmol) was hydrogenated over $Pd(OH)_2$ (1.30 g, 20% on carbon, wet) in MeOH (100 mL) for 60 h. After filtration and evaporation, chromatography (silica, 0-3% MeOH in $CH_2CL_2$) furnished the title compound. MS (+APCI, m/z): 271 (M+H)$^+$, 254 (M−$NH_2$)$^+$, MS (−APCI, m/z): 252 (M−$N_4$)$^-$.

Preparation XIV—5(S)-Hydroxy-5,6,7,8-tetrahydro-naphthalene-2-carboxylic acid methyl ester To an oven-dried 2 L round-bottomed flask equipped with an argon inlet/outlet and magnetic stirring was added (R)-methyl CBS oxaborolidine (7.4 mL of a 1 M soln in toluene, 7.4 mmol, Aldrich). Toluene 190 mL was added and the reaction was cooled in an ice-salt bath (bath temp.=−10° C.). $BH_3$-$SMe_2$ was added (17 mL, 180 mmol, Aldrich), then 5-oxo-5,6,7,8-tetrahydro-naphthalene-2-carboxylic acid methyl ester (30 g, 150 mmol, Albany Molecular) in 200 mL of THF was added over 5 h using a syringe pump. After the addition was complete, the mixture was stirred for an additional 1 h. The mixture was poured into an addition funnel, and the mixture was added to 200 mL of MeOH, cooled in a ice-salt bath, over 30 min at such a rate that the internal temp. was kept below 0° C. The mixture was concentrated in vacuo. $Et_2O$ (1L) was added, and the mixture was washed with 1 M $H_3PO_4$ (3×), satd $NaHCO_3$, and brine (ca. 400 mL each wash). The organic layer was dried over $MgSO_4$, filtered and concentrated in vacuo. The residue was dissolved in $Et_2O$ again (500 mL), and the mixture was washed with 1M $H_3PO_4$ (3×200 mL), satd $NaHCO_3$, and brine. After drying the organic layer over $MgSO_4$, the mixture was filtered and concentrated in vacuo, which gave the title compound as a white-yellow solid. MS (+ion ESI) m/z=207 (MH$^+$), 189 (MH$^+$-$H_2O$).

Preparation XV—5(R)-Azido-5,6,7,8-tetrahydro-naphthalene-2-carboxylic acid methyl ester To a 500 mL three-neck round-bottomed flask equipped with argon inlet/outlet, thermometer, and magnetic stirring was added 5(S)-hydroxy-5,6,7,8-tetrahydro-naphthalene-2-carboxylic acid methyl ester (29 g, 140 mmol) in 280 mL of toluene. The reaction was cooled in a ice-salt bath, and DPPA (36 mL, 170 mmol, Aldrich) was added (internal temp.=−4° C.). DBU (25 mL, 170 mmol, Aldrich) was added over 10 min at such a rate that the internal temp. was kept below 1° C. The ice in the bath was allowed to melt, and the reaction continued for 12 h during which time the mixture stopped stirring because a precipitate had formed. Stirring was resumed, and the mixture was stirred at RT for another 11 h. The reaction contents were poured into a 2 L sep funnel, and the lower dark-brown layer was removed. Water (250 mL) was added to the remaining top layer, and the mixture was extracted with $Et_2O$ (3×250 mL). The combined organic layers were washed with 1 M $H_3PO_4$, water, satd $NaHCO_3$, and brine. The organic layer was dried over $MgSO_4$, filtered and concentrated in vacuo. Purification by silica gel chromatography (330 g Isco Redisepo column, 1:1 hexane-$CH_2Cl_2$) of the crude material provided the title compound. MS (+ion ESI) m/z=232 (MH$^+$).

Preparation XLVI—(5(R)-Amino-5,6,7,8-tetrahydro-naphthalen-2-yl)-methanol

To an oven-dried, 3-neck, 2 L round-bottomed flask equipped with argon inlet/outlet, addition funnel, thermometer, and overhead stirring was added 700 mL of THF and LAH (470 mL of a 1 M soln in THF, 470 mmol, Aldrich). The reaction was cooled in a ice-salt bath, and 5-azido-5,6,7,8-tetrahydro-naphthalene-2-carboxylic acid methyl ester (27 g, 120 mmol) in 100 mL of THF was added over ca. 30 min. The mixture was warmed to RT overnight, then cooled in an ice-salt bath the next morning. Water (18 mL) in THF (20 mL) was added to the reaction mixture over 4 h. Vigorous gas evolution occurred. 5M NaOH (18 mL) was added over 30 min followed by 54 mL of water. After stirring for an additional 1 h, the mixture was filtered, and the filtrate was concentrated in vacuo. The residue was reconstituted in MeOH and $CH_3CN$, and concentrated in vacuo again to provide the title compound as light-brown solid. MS (+ion ESI) m/z=161 (M−$NH_3$).

Similarly (4-(R)-amino-chroman-7-yl)-methanol and (1-(R)-amino-indan-5-yl)-methanol were prepared.

Preparation XVII—7-bromomethyl-6-chloro-chroman-4-one

A mixture of 6-chloro-7-methyl-chroman-4-one (20 g, 101.71 mmol), NBS (19.9 g, 111.88 mmol), and AIBN (4.17 g, 25.43 mmol) in anhydrous $CCl_4$ (300 mL) was heated at reflux in 24 h. The mixture was cooled, filtered the solid. The filtrate was concentrated and used in the next step without purification.

Preparation XVIII—7-(tert-butylamino-methyl)-6-chloro-chroman-4-one

To a stirred mixture of tert-butylamine (7.3 g, 99.78 mmol) and $Et_3N$ (10.1 g, 99.78 mmol) in anhydrous $CH_2Cl_2$ (50 mL) was added a solution of 7-bromomethyl-6-chloro-chroman-4-one (25 g, 90.71 mmol) in $CH_2Cl_2$ (150 mL) dropwise. Stirring was continued for 16 h. The mixture was concentrated, taken up in $H_2O$, acidified with 10% HCl until pH 1, and extracted with $Et_2O$ (discarded). The acidic aqueous layer was neutralized with 5 N NaOH, and extracted with $CH_2Cl_2$ (3×). The combined extracts were dried over $MgSO_4$, concentrated to give a yellow solid.

Preparation XIX—7-(tert-butylamino-methyl)-6-chloro-chroman-4(S)-ol

To a stirred solution of (1S,2S)-(+)-N-(4-toluene-sulfonyl)-1,2-diphenylethylenediamine (0.29 g, 8.08 mmol) in i-PrOH (15 mL) was added [$RuCl_2$(n6-p-cymene)]$_2$, and $Et_3N$ under argon. The mixture was heated at 80° C. for 1 h, cooled, and concentrated to dryness. To this mixture was added a solution of 7-(tert-butylamino-methyl)-6-chloro-chroman-4-one (12 g, 44.91 mole) in anhydrous $CH_3CN$ (150 mL), followed by 5:2 formic acid/TEA (6 mL). The reaction was stirred at RT for 24 h. The mixture was concentrated, taken up in $H_2O$, neutralized with 10% $Na_2CO_3$, extracted with $CH_2Cl_2$ (3×), dried over $MgSO_4$, concentrated to give a brown foam which was stirred in hexane/ether (1:1), and filtered. The filtrate was concentrated to give a light brown foam.

Preparation XX—4(R)-azido-6-chloro-chroman-7-ylmethyl)-tert-butylamine

To a stirred, cooled (0° C.) solution of 7-(tert-butylaminomethyl)-6-chloro-chroman-4(S)-ol (11.55 g, 42.91 mmol) in anhydrous toluene (150 mL) was added DPPA (23.6 g, 85.81 mmol) dropwise in 0.5 h and DBU (13.1 g, 85.91 mmol). The mixture was stirred at RT for 24 h. The mixture was concentrated, taken up in H₂O, extracted with CH₂Cl₂(3×), dried over MgSO₄, concentrated and purified by ISCO (3% MeOH/ CH₂Cl₂) to give a brown oil. MS (APCI) m/z 296 (M+2).

Preparation XXI—7-(tert-butylamino-methyl)-6-chloro-chroman-(4R)-ylamine

A mixture of 4(R)-azido-6-chloro-chroman-7-ylmethyl)-tert-butylamine (12 g, 40.73 mmol) and Ph₃P (16 g, 61.09 mmol) in anhydrous THF (100 mL) was stirred at RT in 3 h. H₂O (100 mL) was added and the mixture was heated at reflux for 24 h. The mixture was cooled, concentrated, taken up in toluene, extracted with 5N HCl. The aqueous layer was neutralized with 1ON NaOH, extracted with CHCl₃ (3×), dried over MgSO₄, concentrated to give a brown oil.

MS (APCI) m/z 270 (M+2).

Preparation XXII—(5,5-Dimethyl-3-oxo-1-(tolune-4-sulfonyl)piperazin-2-yl)acetic acid ethyl ester (5,5-Dimethyl-3-oxo-piperazin-2(R,S)-yl)acetic acid ethyl ester (2.0 g, 10 mmol, prepared according to the literature procedure of Dutta and Foye, J. Pharmaceutical Science 1990, 79, 447-452.) was added to 4-tolunesulfonyl chloride (Aldrich, 3.5 g, 20 mmol) and Na₂CO₃ (3.0 g, 30 mmol) in CH₃CN (40 mL). The mixture was heated at 45° C. overnight. The mixture was cooled to RT. EtOAc (200 mL) was added, and the mixture was washed with brine (3×100 mL). The EtOAc solution was dried and evaporated. The crude compound was purified by column chromatograph (silica gel, hexane-10% EtOAc/hexane-10% EtOAc/-CH₂Cl₂) to give the desired compound as a white solid: MS (APCI+, m/z): 369 (M+1)⁺.

The following compounds were prepared similar to that described above from the appropriate starting materials:
 a) (5,5-Dimethyl-3-oxo-1-(2,4,6-trimethylbenzene-sulfonyl)piperazin-2(R,S)-yl)acetic acid ethyl ester;
 b) 3-oxo-1-(2,4,6-trimethylbenzene-sulfonyl)piperazin-2(R,S)-yl)acetic acid ethyl ester; and
 c) 3-oxo-1-(4-tolune-sulfonyl)piperazin-2(R,S)-yl)acetic acid ethyl ester.

Preparation XXIII—(5.5-Dimethyl-3-oxo-1-(tolune-4-sulfonyl)piperazin-2(R,S)-yl)acetic acid (5,5-Dimethyl-3-oxo-1-(tolune-4-sulfonyl)piperazin-2(R, S)-yl)acetic acid ethyl ester (1.5 g, 4 mmol) was dissolved in 30 mL of MeOH and 30 mL of THF. LiOH (15 mmol) in water (10 mL) was added. The mixture was stirred at RT overnight. The mixture was concentrated, and acidified. After 30 min the precipitate was filtered, washed with water and dried in vacuo to give the titled compound. MS: 339 (M-1)⁺.

The following compounds were prepared similar to that described above from the appropriate starting materials:
 a) (5,5-dimethyl-3-oxo-1-(2,4,6-trimethylbenzene-sulfonyl)piperazin-2(R,S)-yl)acetic acid;
 b) 3-oxo-1-(2,4,6-trimethylbenzene-sulfonyl)piperazin-2 (R,S)-yl)acetic acid; and
 c) 3-oxo-1-(4-tolune-sulfonyl)piperazin-2(R,S)-yl)acetic acid.

Preparation XXIV—[1-(4-acetylamino-benzenesulfonyl)-3-oxo-piperazin-2-yl]-acetic acid To a stirred solution of [1-(4-acetylamino-benzenesulfonyl)-3-oxo-piperazin-2-yl]-acetic acid ethyl ester (0.2 g, 0.52 mmol) in EtOH (5 mL) was added IN LiOH (0.52 mL, 0.52 mmol). Stirring was continued for 24 h. Dowex 1×8–400 (1 g), i-Pr₂NEt (0.5 mL) was added and the mixtrue was stirred for 2 h. The resin was filtered, washed with MeOH/H₂O (85:15, 10 mL), dried and HCO₂H/H₂O (9:1 10 mL) was added and the mixtrue was stirred for 1 h. The resin was filtered off and washed with CH₃CN/H₂O (85:15). The filtrate was concentrated to give an off-white solid. MS (APCI) m/z 356 (M+1).

The following compounds were prepared similar to that described above from the appropriate starting materials:
 a) [3-oxo-1-toluene-4-sulfonyl)-piperazin-2-yl]-acetic acid; MS (APCI) m/z 313 (M+1).
 b) [3-oxo-1-(3-trifluoromethyl-benzenesulfonyl)-piperazin-2-yl]-acetic acid; MS (APCI) m/z 367 (M+1).
 c) [1-(4-methoxy-benzenesulfonyl)-3-oxo-piperazin-2-yl]-acetic acid; MS (APCI) m/z 329 (M+1).
 d) [1-(4-chloro-benzenesulfonyl)-3-oxo-piperazin-2-yl]-acetic acid; MS (APCI) m/z 333 (M+1).

EXAMPLE 1

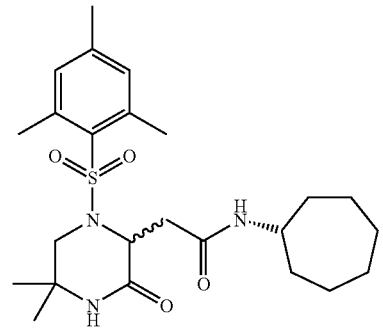

N-Cycloheptyl-2-(5,5-dimethyl-3-oxo-1-(2,4,6-trimethylbenzene-sulfonyl)piperazin-2(R,S)-yl)acetamide To (5,5-dimethyl-3-oxo-1-(2,4,6-trimethylbenzene-sulfonyl)piperazin-2-yl)acetic acid (0.32 g, 0.94 mmol) in DMF (3 mL) was added cycloheptyl amine (0.5 mL), EDC (0.5 g, 2.5 mmol), and DMAP (0.3 g, 2.6 mmol). The mixture was stirred at RT overnight. TLC indicated that the reaction was not complete. Additional EDC (0.3 g) was added and the mixture was heated at 65° C. for 1 h. The mixture was cooled to RT. EtOAc (80 mL) was added and mixture was washed with dilute HCl in brine. The EtOAc solution was dried and evaporated to give the crude compound. Column chromatograph purification (silica gel, 0-2% MeOH/CH₂Cl₂) gave the titled compound. MS: 464.1 (M+1)⁺.

EXAMPLE 2

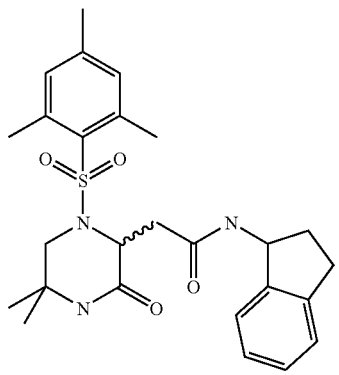

2-[5,5-Dimethyl-3-oxo-1-(2,4,6-trimethyl-benzene-sulfonyl)-piperazin-2(R,S)-yl]-N-indan-1-yl-acetamide

[5,5-Dimethyl-3-oxo-1-(2,4,6-trimethyl-benzenesulfonyl)-piperazin-2(R,S)yl]-acetic acid (50 mg, 0.135 mmol) was dissolved in DMF (2.5 mL) and DIEA (0.1 mL) was added to make a solution. HATU (117 mg, 0.31 mmol) was added and after stirring for two min, (R)-(−)-indanamine (0.1 mL) was added and the mixture was stirred overnight. The solution was poured into EtOAc (50 mL), washed with saturated $NH_4Cl$ (1×50 mL), 1 N HCl (1×50 mL), saturated $NaHCO_3$ (1×50 mL), and saturated brine (1×50 mL). The organic layer was dried with $Na_2SO_4$, filtered, and concentrated in vacuo to provide a crude brown oil (140 mg). This crude oil was purified by $SiO_2$ column chromatography (40 to 100% EtOAc in hexanes) to produce pure title compound. MS (APCI pos) 484 (M+H).

EXAMPLE 3

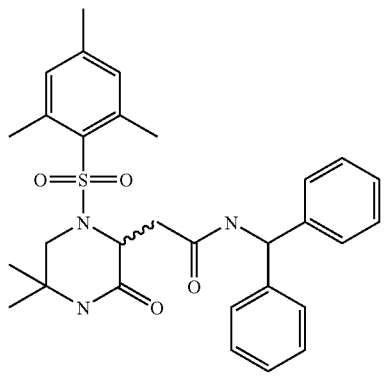

N-Benzhydryl-2-[5,5-dimethyl-3-oxo-1-(2,4,6-trimethyl-benzenesulfonyl)-piperazin-2(R,S)-yl]-acetamide 5,5-Dimethyl-3-oxo-1-(2,4,6-trimethyl-benzenesulfonyl)-piperazin-2(R,S)-yl]-acetic acid (100 mg, 0.27 mmol) was dissolved in DMF (3 mL) and DIEA (0.2 mL) was added to make a solution. HATU (206 mg, 0.54 mmol) was added and after the reaction was stirred for two min, aminodiphenylmethane (0.2 mL) was added and the reaction was stirred overnight. The solution was poured into EtOAc (50 mL), washed with saturated $NH_4Cl$ (1×50 mL), 1 N HCl (1×50 mL), saturated $NaHCO_3$ (1×50 mL), and saturated brine (1×50 mL). The organic layer was dried with $Na_2SO_4$, filtered, and concentrated in vacuo to provide crude brown oil (355 mg). This crude oil was purified by $SiO_2$ column chromatography (50 to 100% EtOAc in hexanes) to produce pure title compound. MS (APCI pos) 534 (M+H).

The following compounds were prepared similar to that described above from the appropriate starting materials:

EXAMPLE 3a 2-((2R,S)-5,5-dimethyl-3-oxo-1-((2,4,6-trimethylphenyl)sulfonyl)-2-piperazinyl)-N-((1R)-5-(hydroxymethyl)-2,3-dihydro-1H-inden-1-yl)acetamide; MS 514 (M+H).

EXAMPLE 3b 2-((2R,S)-5,5-dimethyl-3-oxo-1-((2,4,6-trimethylphenyl)sulfonyl)-2-piperazinyl)-N-(1,2,3,4-tetrahydro-1-naphthalenyl)acetamide;

MS 498 (M+H).

EXAMPLE 3c

2-[3-Oxo-1-(2,4,6-trimethylbenzenesulfonyl)-piperizin-2(R,S)-yl]-N-(1,2,3,4-tetrahydronaphthalen-1-yl)-acetamide. MS (ESI, pos. ion.) m/z: 470 (M+1).

EXAMPLE 4

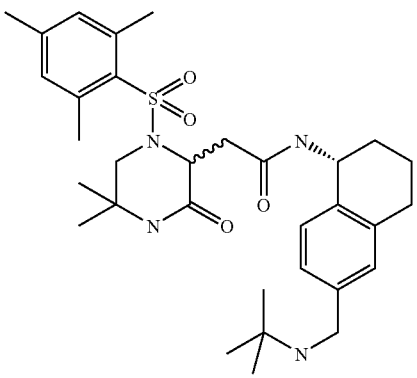

N-[6-(tert-Butylamino-methyl)-1,2,3,4-tetrahydro-naphthalen-1-yl]-2-[5,5-dimethyl-3-oxo-1-(2,4,6-trimethyl-benzenesulfonyl)-piperazin-2(R,S)-yl]-acetamide A) Preparation of 2-[5,5-dimethyl-3-oxo-1-(2,4,6-trimethyl-benzenesulfonyl)-piperazin-2(R,S)-yl]-N-(6-hydroxymethyl-1,2,3,4-tetrahydro-naphthalen-1(R)-yl)-acetamide [5,5-Dimethyl-3-oxo-1-(2,4,6-trimethyl-benzenesulfonyl)-piperazin-2(R,S)-yl]-acetic acid (600 mg, 1.6 mmol) and (5(R)-amino-5,6,7,8-tetrahydro-naphthalen-2-yl)-methanol (290 mg, 1.6 mmol) were dried by azeotroping with anhydrous toluene (3×1 mL) and dissolved in anhydrous DMF (10 mL). DIEA (0.55 mL, 3.2 mmol) and HATU (923 mg, 2.4 mmol) were added to the reaction and stirred for 18 h at RT. The reaction was diluted with EtOAc (30 mL), washed with dilute HCl (2×), 1N NaOH (2×), and brine, dried over MgSO₄, filtered, and concentrated in vacuo to provide a residue which was purified by column chromatography (SiO₂, 5% MeOH in CH₂Cl₂) to provide the title compound.

ESMS 528.4 (M+H), 526.6 (M−H).

B) Preparation of 2-[5,5-dimethyl-3-oxo-1-(2,4,6-trimethyl-benzenesulfonyl)-piperazin-2(R,S)-yl]-N-(6-formyl-1,2,3,4-tetrahydro-naphthalen-1(R)-yl)-acetamide Manganese (IV) oxide (1.0 g, 11.5 mmol) was added to a solution of 2-[5,5-dimethyl-3-oxo-1-(2,4,6-trimethyl-benzenesulfonyl)-piperazin-2(R,S)-yl]-N-(6-hydroxymethyl-1,2,3,4-tetrahydro-naphthalen-1(R)-yl)-acetamide (Step a, 620 mg, 1.17 mmol) in CH₂Cl₂ (25 mL). The reaction was stirred for 2 h at RT, filtered through Celite® and concentrated in vacuo to provide the title compound. ESMS 526.4 (M+H), 524.5 (M−H).

C) Preparation of N-[6-(tert-butylamino-methyl)-1,2,3,4-tetrahydro-naphthalen-1(R)-yl]-2-[5,5-dimethyl-3-oxo-1-(2,4,6-trimethyl-benzenesulfonyl)-piperazin-2(R,S)-yl]-acetamide 2-[5,5-Dimethyl-3-oxo-1-(2,4,6-trimethyl-benzenesulfonyl)-piperazin-2(R,S)-yl]-N-(6-formyl-1,2,3,4-tetrahydro-naphthalen-1(R)-yl)-acetamide (Step b, 550 mg, 1.0 mmol) was dissolved in 1,2-dicholoethane (10 mL) and tert-butylamine (1.5 mL). NaBH(OAc)₃ (1.5 g, 6.0 mmol) was added to the reaction, and heated to 85° C. in a sealed tube for 18 h. The mixture was cooled to RT, diluted with EtOAc (25 mL), washed with sat. NaHCO₃ solution (2×), and brine, dried over MgSO₄, filtered, and concentrated in vacuo to provide a residue which was purified by column chromatography (SiO₂, 10% MeOH in CH₂Cl₂+1% NH₃) to provide the title compound. ESMS 583.4 (M+H), 581.5 (M−H).

The following compounds were prepared similar to that described above from the appropriate starting materials:

EXAMPLE 4a

N-((1R)-5-(((1,1-dimethylethyl)amino) methyl)-2,3-dihydro-1H-inden-1-yl)-2-((2R,S)-5,5-dimethyl-1-((4-methylphenyl)sulfonyl)-3-oxo-2-piperazinyl) acetamide was made from 5,5-dimethyl-3-oxo-1-(2,4,6-trimethyl-benzenesulfonyl)-piperazin-2-yl]-acetic acid and (1-(R)-amino-indan-5-yl)methanol.

EXAMPLE 4b

N-((1R,S)-6-(((1,1-dimethylethyl)amino) methyl)-1,2,3,4-tetrahydro-1-naphthalenyl)-2-((2R,S)-5,5-dimethyl-1-((4-methylphenyl)sulfonyl)-3-oxo-2-piperazinyl)acetamide was made from 5-dimethyl-3-oxo-1-(4-tolune-sulfonyl)-piperazin-2-yl]-acetic acid and (5-(R,S)-amino-5,6,7,8-tetrahydro-naphthalen-2-yl)-methanol.

EXAMPLE 5

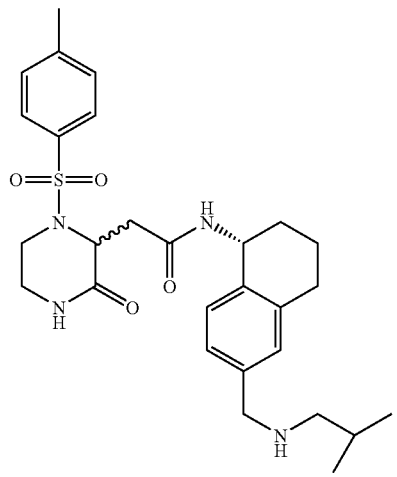

N-{6-[2-Methyl-propylamino)-methyl]-1,2,3,4-tetrahydro-naphthalen-1(R)-yl)-2-[3-oxo-1-(tolune-4-sulfonyl)-piperazin-2(R,S)-yl]-acetamide A) Preparation of N-(6-hydroxymethyl-1,2,3,4-tetrahydro-naphthalen-1(R)-yl)-2-[3-oxo-1-(toluene-4-sulfonyl)-piperazin-2 (R,S)-yl]-acetamide To a 50 mL flask was added 3-oxo-1-(4-toluene-sulfonyl) piperazin-2 (R,S)-yl)acetic acid (312 mg, 1.0 mmol), HOBT (162 mg, 1.2 mmol) and EDC (230 mg, 1.2 mmol). This mixture was dissolved in 2 mL of dichloroethane and 1 mL of NMP. This solution was added dropwise to a stirred solution of (5-(R)-amino-5,6,7,8-tetrahydro-naphthalen-2-yl)-methanol in 1 mL of NMP over 20 min. After stirring overnight at RT, the solution was diluted with EtOAc, and quenched with water. The aqueous phase was extracted with EtOAc (10 mL×2). The organic layers was combined and washed with water, sat. NaHCO₃ and brine, dried over Na₂SO₄ and evaporated in vacuo. Flash chromatography (SiO₂, EtOAc to MeOH/EtOAc=5% to 10% to 12%) afforded the titled compound as a white solid.

B) Preparation of N-(6-formyl-1,2,3,4-tetrahydro-naphthalen-1(R)-yl)-2-[3-oxo-1-(toluene-4-sulfonyl)-piperazin-2 (R,S)-yl]-acetamide To a solution of N-(6-hydroxymethyl-1,2,3,4-tetrahydro-naphthalen-1(R)-yl)-2-[3-oxo-1-(toluene-4-sulfonyl)-piperazin-2(R,S)-yl]-acetamide (425 mg, 0.90 mmol) in CH₂Cl₂ (10 mL) at RT was added MnO₂ (392 mg, 4.51 mmol). After stirring for 1 h, another 392 mg of MnO₂ was added. After 3 h, the mixture was filtered through a Celite® pad with the help of a mixed solvent (EtOAc/MeOH=2:1). The resulting solution was evaporated to give the title compound.

C) Preparation of N-{6-[2-methylpropylamino)-methyl]-1,2,3,4-tetrahydro-naphthalen-1(R)-yl)-2-[3-oxo-1-(toluene-4-sulfonyl)-piperazin-2(R,S)-yl]-acetamide To a solution of N-(6-formyl-1,2,3,4-tetrahydro-naphthalen-1(R)-yl)-2-[3-oxo-1-(toluene-4-sulfonyl)-piperazin-2(R,S)-yl]-acetamide (Step b, 646 mg, 1.38 mmol) and isobutylamine (0.69 mL, 6.89 mmol) in 12 mL of dichloroethane was added NaBH(OAc)₃ (875.5 mg, 4.13 mmol). After stirring overnight at RT, the reaction was diluted with EtOAc and washed with sat NaHCO₃ and brine. The organic phase was dried over Na₂SO₄ and evaporated to dryness in vacuo. Flash chromatography (SiO₂, EtOAc to EtOAc/MeOH=100:15 to EtOAc/NH₃ in MeOH=100:10 to 100:20) afforded the title compound as a white solid. MS: 527.3 (M+1).

The following compounds were prepared similar to that described above from the appropriate starting materials:

EXAMPLE 5a

N-((1R)-6-(((1,1-Dimethylethyl)amino) methyl)-1,2,3,4-tetrahydro-1-naphthalenyl)-2-((2R,S)-1-((4-methylphenyl)sulfonyl)-3-oxo-2-piperazinyl)acetamide; white solid. MS: 527.4 (M+1).

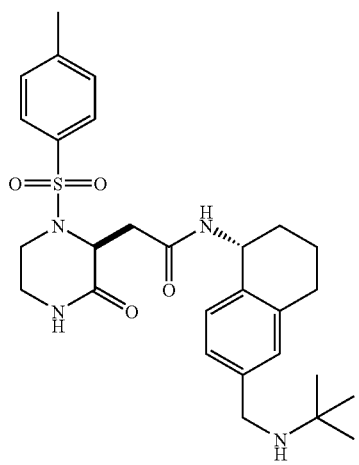

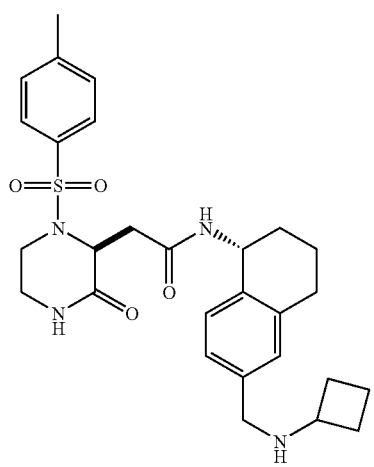

EXAMPLE 5b

N-((1R)-6-(((Cyclobutylamino)methyl)-1,2,3,4-tetrahydro-1-naphthalenyl)-2-((2R,S)-1-((4-methylphenyl)sulfonyl)-3-oxo-2-piperazinyl)acetamide; white solid. MS: 525.6 (M+1).

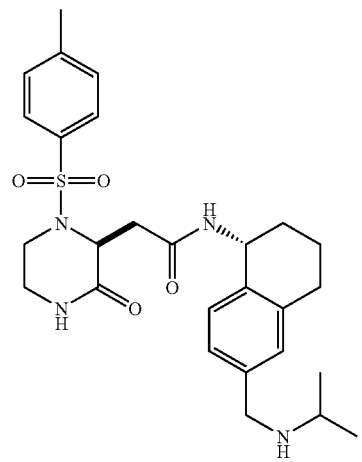

EXAMPLE 5c

N-((1R)-6-(((1-Methylethyl)amino)methyl)-1,2,3,4-tetrahydro-1-naphthalenyl)-2-((2R,S)-1-((4-methylphenyl)sulfonyl)-3-oxo-2-piperazinyl)acetamide; white solid. MS: 513.4 (M+1).

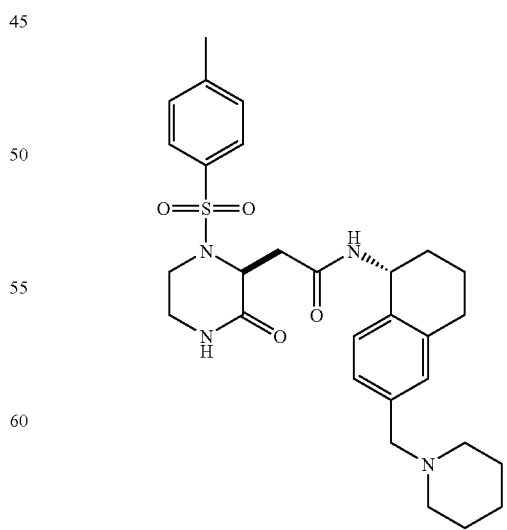

EXAMPLE 5d

2-[3-Oxo-1-(tolune-4-sulfonyl)-piperazin-2(R,S)-yl]-N-(6-piperidin-1-ylmethyl-1,2,3,4-tetrahydro-naphthalen-1(R)-yl)-acetamide. White solid. MS: 539.7 (M+1).

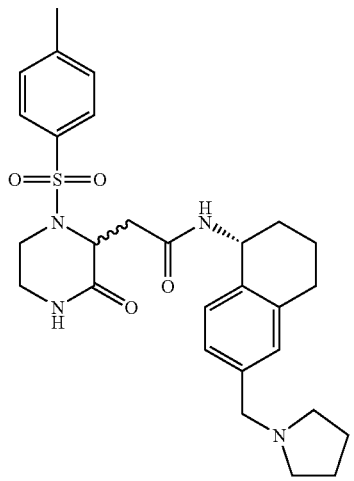

EXAMPLE 5e

2-[3-Oxo-1-(tolune-4-sulfonyl)-piperazin-2(R,S)-yl]-N-(6-pyrrolidin-1-ylmethyl-1,2,3,4-tetrahydro-naphthalen-1(R)-yl)-acetamide. White solid. MS: 525.4 (M+1).

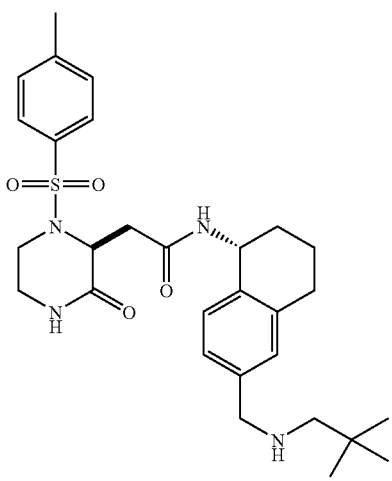

EXAMPLE 5f

N-{6-[2,2-dimethyl-propylamino)-methyl]-1,2,3,4-tetrahydro-naphthalen-1(R)-yl)-2-[3-oxo-1-(tolune-4-sulfonyl)-piperazin-2(R,S)-yl]-acetamide; White solid. MS: 541.4 (M+1).

EXAMPLE 6

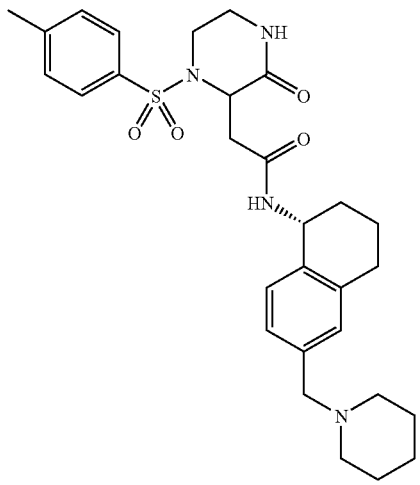

2-[3-Oxo-1-(toluene-4-sulfonyl)piperizin-2-yl]-N-(6-piperidin-1-ylmethyl-1,2,3,4-tetrahydronaphthalen-1-yl)-acetamide A) Preparation of 5(S)-Hydroxy-5,6,7,8-tetrahydronaphthalene-2-carbonitrile To a 250-mL three-necked flask containing (R)-CBS (2.9 mL, 1.0 M in toluene, 2.9 mmol, Aldrich) under $N_2$, was added a solution of $BH_3$-$SMe_2$ (4.0 g, 53 mmol, Aldrich) in toluene (50 mL) dropwise through an additional funnel. After the addition, the solution was cooled to 0° C. A solution of 5-oxo-5,6,7,8-tetrahydronaphthalene-2-carbonitrile (10 g, 58 mmol, Rintech) in THF (180 mL) was added through an addition funnel over a period of 1.5 h. The mixture was stirred at 0° C. for additional 30 min. A preformed mixture of MeOH (50 mL) and acetyl chloride (0.21 mL, 2.9 mmol, Aldrich) was added dropwise to the reaction mixture. The reaction was stirred at RT overnight. The solvents were removed in vacuo and the residue was dissolved in HCl (150 mL, 5%). The compound was extracted with EtOAc (3'250 mL). The combined organics were washed with brine (300 mL, 5%) and dried over $Na_2SO_4$. Filtration and concentration in vacuo afforded the title compound as a light yellow solid. MS (ESI, pos. ion.) m/z: 174 (M+1).

B) Preparation of 5(R)-azido-5,6,7,8-tetrahydronaphthalene-2-carbonitrile

To a 500-mL round-bottomed flask containing 5-hydroxy-5,6,7,8-tetrahydronaphthalene-2-carbonitrile [step a, 9.9 g, 57 mmol] in THF (240 mL) at RT was added DPPA (21 g, 77 mmol, Aldrich). The solution was cooled to 0° C. and DBU (12 g, 78 mmol, Aldrich) was added slowly through a syringe. The mixture was stirred at RT overnight. The reaction was quenched with HCl (100 mL, 10%) and THF was removed in vacuo. The residue was taken up in water (100 mL) and the compound was extracted with $CH_2Cl_2$ (3×200 mL). The combined organics were washed with brine (300 mL, 5%) and dried over $Na_2SO_4$. Filtration and concentration in vacuo followed by silica-gel chromatography (10:1 hexane:EtOAc) afforded the title compound as colorless oil.

C) Preparation of 5(R)-amino-5,6,7,8-tetrahydronaphthalene-2-carbonitrile

A solution of 5-azido-5,6,7,8-tetrahydronaphthalene-2-carbonitrile [10 g, 53 mmol, step (b)] in EtOH (150 mL) was stirred at RT in the presence of 10% Pd/C (1050 mg, Aldrich) under $H_2$ (1 atm) for 4 h. The reaction was passed through a pad of Celite® and the pad was washed with MeOH (2×100 mL). The filtrate was concentrated in vacuo to afford the title compound as an orange oil.

MS (ESI, pos. ion.) m/z: 173 (M+1).

D) Preparation of 5(R)-(1,3-dioxo-1,3-dihydro-isoindol-2-yl)-5,6,7,8-tetrahydronaphthalene-2-carbonitrile To a 200-mL round-bottomed flask equipped with Dean-Stark apparatus was added 5-amino-5,6,7,8-tetrahydro-naphthalene-2-carbonitrile [9.0 g, 52 mmol, step(c)], phthalic anhydride (8.5 g, 58 mmol, Aldrich), DIEA (2.4 g, 19 mmol, Aldrich), and toluene (175 mL). The reaction was heated at reflux for 3 h. After cooling to RT, the mixture was concentrated in vacuo. The residue was taken up in HCl (150 mL, 10%) and extracted with $CH_2Cl_2$ (3×150 mL). The organic phase was washed with 5% brine (2×70 mL), dried over $Na_2SO_4$, filtrated, and concentrated. The solution of the crude compound in $CH_2Cl_2$ (100 mL) sat overnight at RT and partially precipitated out as crystalline material. Crystalline solid was collected by filtration (2.4 g, 98% ee.). The mother liquor was concentrated in vacuo and purification by chromatography (silica gel, 5:1 hexane:EtOAc gave the title compound as an off-white solid. MS (ESI, pos. ion.) m/z: 303 (M+1).

E) Preparation of 5(R)-(1,3-dioxo-1,3-dihydro-isoindol-2-yl)-5,6,7,8-tetrahydronaphthalene-2-carbaldehyde To a 100-mL round-bottomed flask containing 5-(1,3-dioxo-1,3-dihydro-isoindol-2-yl)-5,6,7,8-tetrahydro-naphthalene-2-carbonitrile [0.95 g, 3.2 mmol, step d] in formic acid (11 mL, Aldrich), was added Raney-Ni (0.95 g, 3201, Aldrich) and water (1 mL). The reaction was heated at reflux for 6 h. After cooling to RT, the mixture was filtered through Celite and the filtrate was concentrated in vacuo. The residue was taken up in EtOAc (50 µL), washed with 5% brine (2×10 mL), and dried over $Na_2SO_4$. Filtration and concentration in vacuo afforded the crude compound. Purification by column chromatography over silica gel with hexane:EtOAc (5:1) gave the title compound as a white solid.

F) Preparation of 2-(6-piperidin-1-ylmethyl-1,2,3,4-tetrahydronaphthalene-1(R)-yl)-isoindole-1,3-dione To a 100-mL round-bottomed flask containing 5 (R)-(1,3-dioxo-1,3-dihydro-isoindol-2-yl)-5,6,7,8-tetrahydronaphthalene-2-carbaldehyde [0.54 g, 1.8 mmol, step (e)] in DMF, was added piperidine (0.35 mL, 3.5 mmol, Aldrich), $NaBH(OAc)_3$ (0.75 g, 3.5 mmol), and glacial AcOH (12 mg, 0.2 mmol, J. T. Baker). The reaction mixture was stirred at RT for 12 h. After removal of the solvent in vacuo, the residue was taken up in EtOAc (50 mL) and the resulting organic phase was washed with 5% brine (2×15 mL), and dried over $Na_2SO_4$. Filtration, concentration in vacuo afforded the title compound as a clear oil. MS (ESI, pos. ion.) m/z: 375 (M+1).

G) Preparation of 6-piperidin-1-ylmethyl-1,2,3,4-tetrahydronaphthalene-1(R)-ylamine To a 100-mL round-bottomed flask containing 2-(6-piperidin-1-ylmethyl-1,2,3,4-tetrahydronaphthalene-1(R)-yl)-isoindole-1,3-dione [0.63 g, 1.7 mmol, step (f)] in EtOH (10 mL), was added hydrazine (1.3 mL, 42 mmol, Aldrich). The reaction was stirred at RT for 2 h. After the removal of the solvent and excess hydrazine in vacuo, the residue was taken in EtOH (15 mL) and heated at reflux under $N_2$ for 2 h. After cooling to RT, filtration through a fritted-glass funnel gave the title compound as a clear oil. MS (ESI, pos. ion.) m/z: 245 (M+1).

H) Preparation of 2-[3-oxo-1-(toluene-4-sulfonyl)piperizin-2(R,S)-yl]-N-(6-piperidin-1-ylmethyl-1,2,3,4-tetrahydronaphthalen-1(R)-yl)-acetamide The coupling of [3-oxo-1-(toluene-4-sulfonyl)piperizin-2-yl]-acetic acid and 6-piperidin-1-ylmethyl-1,2,3,4-tetrahydro-naphthalene-1-ylamine (Step g) in the presence of HATU following the general procedure outline in Example 3 gave the titled compound. MS (ESI, pos. ion.) m/z: 539 (M+1).

The following compounds were prepared similar to that described above from the appropriate starting materials:

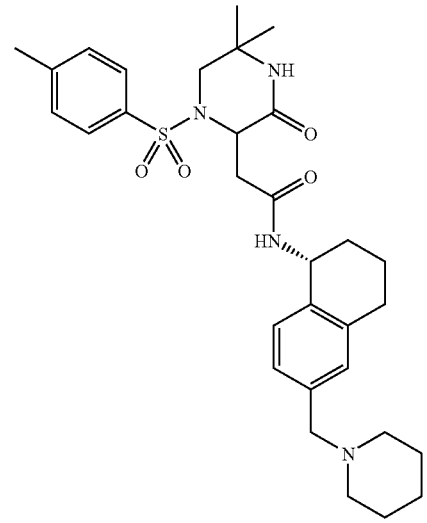

EXAMPLE 6a

2-[5,5-Dimethyl-3-oxo-1-(toluene-4-sulfonyl)-piperizin-2(R,S)-yl]-N-(6-piperidin-1-ylmethyl-1,2,3,4-tetrahydronaphthalen-1(R)-yl)-acetamide.

MS (ESI, pos. ion.) m/z: 567 (M+1).

EXAMPLE 7

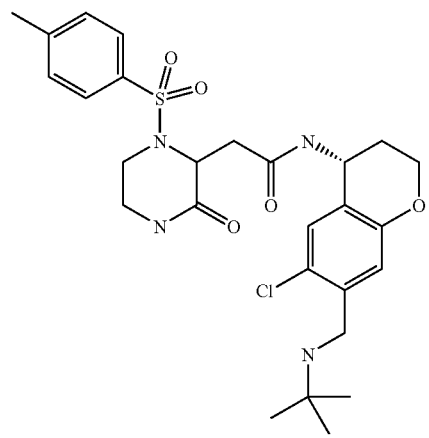

N-[7-(tert-Butylamino-methyl)-6-chloro-chroman-4-yl]-2-[3-oxo-1-(toluene-4-sulfonyl)-piperazin-2-yl]-acetamide A mixture of 3-oxo-1-toluene-4-sulfonyl)-piperazin-2-yl]-acetic acid (0.050 g, 0.14 mmol), HOAt (0.025 g, 0.18 mmol), i-Pr$_2$NEt (0.12 mL, 0.70 mmol), and EDC (0.035 g, 0.18 mmol) in anhydrous DMF (2 mL) was stirred at RT in 24 h. The mixture was concentrated, taken up in H$_2$O, extracted with CH$_2$Cl$_2$ (3×), dried over MgSO$_4$, concentrated and purified by pre-TLC plate to give the title compound. MS (APCI) m/z 563 (M+1). 562.20 Calc'd for C$_{27}$H$_{35}$ClN$_4$O$_5$S.

The following compounds were prepared similar to that described above from the appropriate starting materials:

EXAMPLE 8

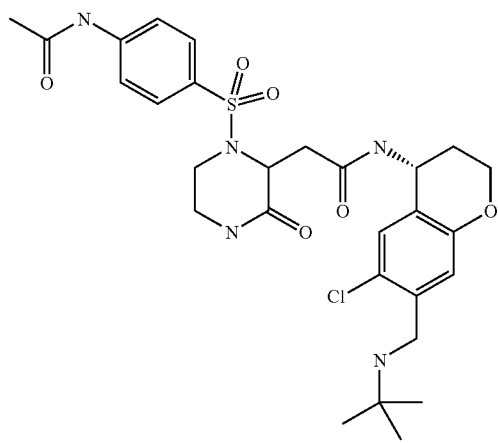

2-[1-(4-Acetylamino-benzenesulfonyl)-3-oxo-piperazin-2-yl]-N-[7-(tert-butylamino-methyl)-6-chloro-chroman-4-yl]-acetaminde MS (APCI) m/z 606 (M+1). 605.21 Calc'd for C$_{28}$H$_{36}$ClN$_5$O$_6$S.

EXAMPLE 9

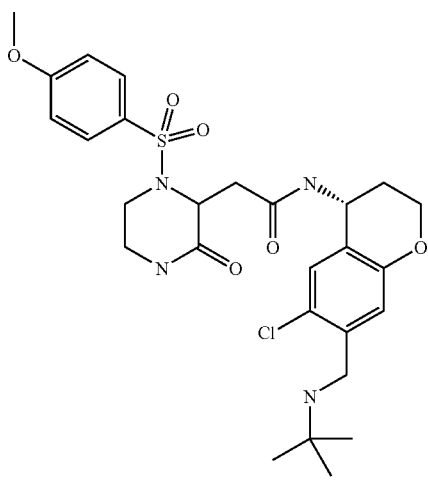

N-[7-(tert-Butylamino-methyl)-6-chloro-chroman-4-yl]-2-[3-oxo-1-(4-methoxy-benzenesulfonyl)-piperazin-2-yl]-acetamide MS (APCI) m/z 579 (M+1). 578.20 Calc'd for C$_{27}$H$_{35}$ClN$_4$O$_6$S.

EXAMPLE 10

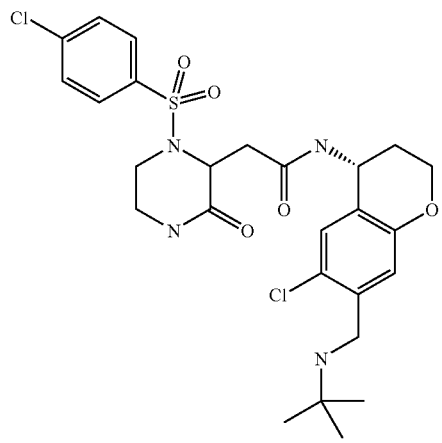

N-[7-(tert-Butylamino-methyl)-6-chloro-chroman-4-yl]-2-[3-oxo-1-(4-chloro-benzenesulfonyl)-piperazin-2-yl]-acetamide MS (APCI) m/z 583 (M+1). 582.15 Calc'd for C$_{26}$H$_{32}$Cl$_2$N$_4$O$_5$S.

EXAMPLE 11

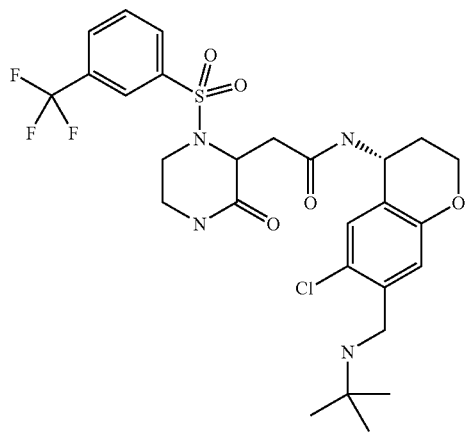

N-[7-(tert-Butylamino-methyl)-6-chloro-chroman-4-yl]-2-[3-oxo-1-(3-trifluoromethyl-benzenesulfonyl)-piperazin-2-yl]-acetamide MS (APCI) m/z 617 (M+1). 616.71 Calc'd for C$_{27}$H$_{32}$ClF$_3$N$_4$O$_5$S.

EXAMPLE 12

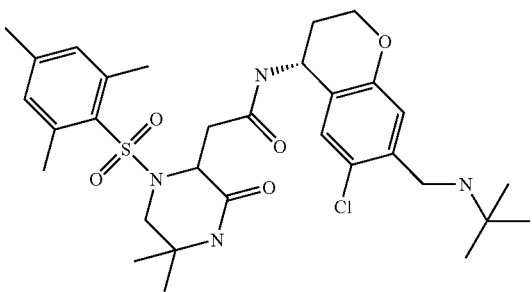

N-((4R)-6-Chloro-7-(((1,1-dimethylethyl)amino)methyl)-3,4-dihydro-2H-chromen-4-yl)-2-((2R,S)-5,5-dimethyl-3-oxo-1-((2,4,6-trimethylphenyl)sulfonyl)-2-piperazinyl)acetamide

EXAMPLE 13

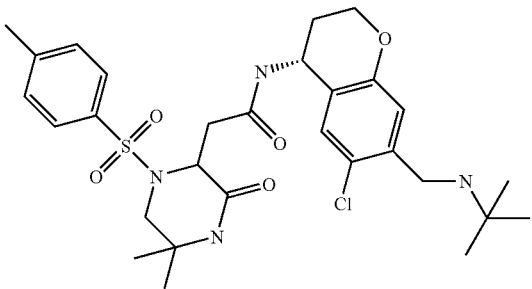

N-((4R)-6-Chloro-7-(((1,1-dimethylethyl)amino)methyl)-3,4-dihydro-2H-chromen-4-yl)-2-((2R,S)-5,5-dimethyl-1-((4-methylphenyl)sulfonyl)-3-oxo-2-piperazinyl)acetamide

EXAMPLE 14

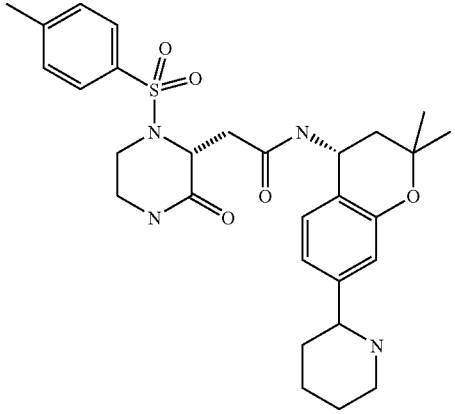

N-((4R)-2,2-dimethyl-7-(2-piperidinyl)-3,4-dihydro-2H-chromen-4-yl)-2-((2R)-1-((4-methylphenyl)sulfonyl)-3-oxo-2-piperazinyl)acetamide A) Preparation of N-(2,2-dimethyl-7-pyridin-2-yl-chroman-4R-yl)-2R-[3-oxo-1-toluene-4-sulfonyl)-piperazin-2-yl]-acetamide A mixture of [3-oxo-1-toluene-4-sulfonyl)-piperazin-2R-yl]-acetic acid (0.41 g, 1.30 mmol), HOAt (0.30 g, 1.95 mmol), i-Pr$_2$NEt, [2,2,-dimethyl-7-pyridin-2R-yl-chroman-4-ylamine (0.33 g, 1.30 mmol), and EDC (0.40 g, 1.95 mmol) in anhydrous DMF (10 mL) was stirred at RT in 24 h. The mixture was quenched by H$_2$O, and the solid was filtered, purified by ISCO (3% MeOH/-CH$_2$Cl$_2$) to give the title compound. MS (APCI) m/z 549 (M+1).

B) Preparation of N-((4R)-2,2-dimethyl-7-(2-piperidinyl)-3,4-dihydro-2H-chromen-4-yl)-2-((2R)-1-((4-methylphenyl)sulfonyl)-3-oxo-2-piperazinyl)acetamide A mixture of N-(2,2-dimethyl-7-pyridin-2-yl-chroman-4R-yl)-2R-[3-oxo-1-toluene-4-sulfonyl)-piperazin-2-yl]-acetamide (Step a, 0.15 g, 0.27 mmol), PtO$_2$ (0.20 g), and HOAc (0.1 mL) in MeOH (10 mL) was hydrogenated at RT in 24 h. The catalyst was filtered off. The filtrate was concentrated and purified by ISCO (15% MeOH/CH$_2$Cl$_2$) to give the title compound. MS (APCI) m/z 555 (M+1).

EXAMPLE 15

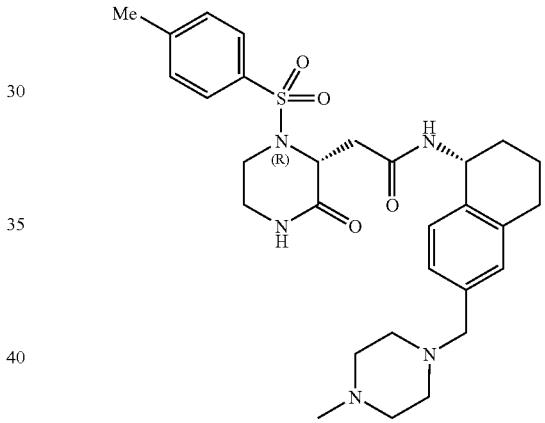

N-[6-(4-Methyl-piperazin-1-ylmethyl)-1,2,3,4-tetrahydronaphthalen-1R-yl]-2-[3-oxo-1-(toluene-4-sulfonyl)-piperazin-2R-yl]-acetamide A) Preparation of 3(R)-benzyloxycarbonylamino-N-(2,2-dimethoxy-ethyl)-succinamic acid tert-butyl ester A mixture of D-CBz-ASP(OTBU)—OH (5 g, 15.46 mmol), HOAt (2.72 g, 20.1 mmol), i-Pr$_2$NEt (10 g, 77.3 mmol), amino acetaldehyde dimethyl acetal (3.25 g, 30.92 mmol), and EDC (3.90 g, 20.1 mmol) in anhydrous CH$_3$CN (100 mL) was stirred at RT for 24 h. The mixture was concentrated, taken up in H$_2$O, extracted with EtOAc (3×), dried over MgSO$_4$, concentrated and purified by ISCO (30% EtOAc/Hexane) to give a colorless oil.

B) Preparation of 2R-tert-butoxycarbonylmethyl-3-oxo-3,4-dihydro-2H-pyrazine-1-carboxylic acid benzyl ester A mixture of 3R-benzyloxycarbonylamino-N-(2,2-dimethoxy-ethyl)-succinamic acid tert-butyl ester (Step a, 3.2 g, 7.80 mmol) and p-TsOH (0.13 g, 0.78 mmol) in anhydrous toluene (50 mL) was stirred at 55° C. for 1 h. The mixture was cooled, concentrated, and purified by ISCO (20% EtOAc/Hexane) to give a colorless oil.

C) Preparation of (3-oxo-piperazin-2R-yl)-acetic acid tert-butyl ester

A solution of 2R-tert-butoxycarbonylmethyl-3-oxo-3,4-dihydro-2H-pyrazine-1-carboxylic acid benzyl ester (Step b, 1.7 g, 4.91 mmol) in MeOH (20 mL) was hydrogenated at RT in 10% Pd/C (0.1 g) in 36 h. The catalyst was filtered off, and the filtrate was concentrated and used in the next step without further purification.

D) Preparation of [3-oxo-1-(toluene-4-sulfonyl)-piperazin-2R-yl]acetic acid tert-butyl ester To a stirred, cooled (0° C.) mixture of (3-oxo-piperazin-2R-yl)-acetic acid tert-butyl ester (Step c, 1.06 g, 4.95 mmol) and Et₃N (0.76 mL, 1.1 mmol) in anhydrous CH₂Cl₂ (15 mL) was added p-TsCl. The mixture was stirred at RT for 4 h, H₂O was added, and layers were separated. The organic extracts were dried over MgSO₄, concentrated, and used in the next step without further purification.

MS (APCI) m/z 369 (M+1).

E) Preparation of [3-oxo-1-toluene-4-sulfonyl)-piperazin-2R-yl]-acetic acid

To a stirred solution of 3-oxo-1-(toluene-4-sulfonyl)-piperazin-2R-yl]acetic acid tert-butyl ester (Step d, 1.7 g, 4.62 mmol) in CH₂Cl₂ (20 mL) was added 95% TFA/H₂O (1 mL) and stirred for 2 h. The mixture was concentrated, triturated in ether to give the title compound. MS (APCI) m/z 313 (M+1).

F) Preparation of N-(6-hydroxymethyl-1,2,3,4-tetrahydronaphthalen-1R-yl)-2-[3-oxo-1-(toluene-4-sulfonyl)-piperazin-2R-yl)]-acetamide Following the same preparation of N-(2,2-dimethyl-7-pyridin-2-yl-chroman-4R-yl)-2R-[3-oxo-1-(toluene-4-sulfonyl)-piperazin-2-yl]-acetamide (Example 14) gave the title compound. MS (APCI) m/z 472 (M+1).

G) Preparation of N-(6-chloromethyl-1,2,3,4-tetrahydronaphthalen-1R-yl)-2-[3-oxo-1-(toluene-4-sulfonyl)-piperazin-2R-yl]-acetamide To a stirred solution of N-(6-hydroxymethyl-1,2,3,4-tetrahydro-naphthalen-1R-yl)-2-[3-oxo-1-(toluene-4-sulfonyl)-piperazin-2-yl)]-acetamide (Step f, 0.16 g, 0.34 mmole) in anhydrous p-dioxane (5 mL) was added SOCl₂ (0.13 g, 1.02 mmol). Stirring was continued for 3 h. The mixture was concentrated to give a brown oil. MS (APCI) m/z 490 (M+1).

H) Preparation of N-[6-(4-methyl-piperazin-1-ylmethyl)-1,2,3,4-naphthalen-1R-yl]-2-[3-oxo-1-(toluene-4-sulfonyl)-piperazin-2R-yl]-acetamide To a stirred solution of N-(6-chloromethyl-1,2,3,4-tetrahydro-naphthalen-1R-yl)-2-[3-oxo-1-(toluene-4-sulfonyl)-piperazin-2R-yl]-acetamide (Step g, 0.16 g, 0.32 mmole) in anhydrous p-dioxane (2 mL) was added N-methylpiperazine (0.08 g, 1.1 mmol). Stirring was continued for 2 h. The mixture was concentrated, taken up in H₂O, and a tan solid was filtered. The solid was air dried and purified by prep-TLC to give a tan solid. MS (APCI) m/z 554 (M+1).

EXAMPLE 16

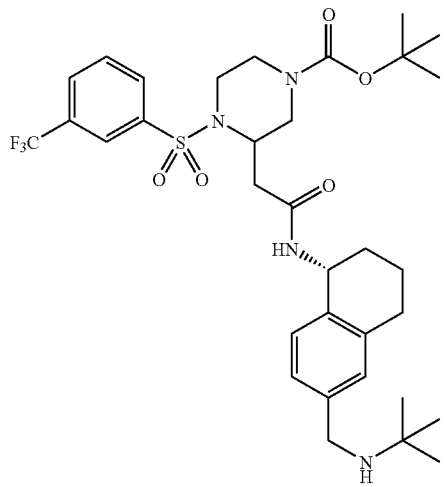

3-{[6-(tert-Butylamino-methyl)-1,2,3,4-tetrahydro-naphthalen-1(R)-ylcarbamoyl]-methyl}-4-(3-trifluoromethyl-benzenesufonyl)-piperazine-1(R,S)-carboxylic acid tert-butyl ester A) Preparation of 3(R,S)-methoxycarbonylmethyl-4-(3-trifluoromethyl-benzenesulfonyl)-piperazine-carboxylic acid tert-butyl ester To a 250-mL round-bottomed flask containing methyl 4-Boc-piperizine-2(R,S)-acetate (2.0 g, 7.7 mmol, Astatech) in THF (5 mL), was added 3-trifluoromethylbenzenesulfonyl chloride (1.9 g, 7.7 mmol, Aldrich) and sat K₂CO₃ (5 mL). The reaction was stirred at RT for 20 h. The compound was extracted with EtOAc (25 mL) and the organic phase was washed with 5% brine (2×5 mL), and dried over Na₂SO₄. Filtration and concentration in vacuo, followed by column chromatography over silica gel with hexane:EtOAc (3:1) gave the title compound as a clear oil. MS (ESI, pos. ion.) m/z: 467 (M+1).

B) Preparation of 3(R,S)-carboxyymethyl-4-(3-trifluoromethyl-benzenesulfonyl)-carboxylic-carboxylic acid tert-butyl ester To a 200-mL round-bottomed flask containing 3(R,S)-methoxycarnonylmethyl-4-(3-trifluoromethyl-benzenesulfonyl)-carboxylic-carboxylic acid tert-butyl ester [3.0 g, 6.4 mmol, step (a)] in THF (10 mL), was added LiOH (0.81 g, 19 mmol, Aldrich). The reaction was stirred at RT overnight. The mixture was acidified to pH 6 with 2 N HCl and the compound was extracted with EtOAc (2×30 mL). The organic phase was washed with 5% brine (2×10 mL), dried over Na₂SO₄. Filtration and concentration in vacuo afforded the title compound as a white solid. MS (ESI, pos. ion.) m/z: 453 (M+1).

C) Preparation of 3(R,S)-[6-hydroxymethyl-1,2,3,4-tetrahydronaphthalen-1(R)-ylcarbamoyl]-methyl]-4-(3-trifluoromethyl-benzenesulfonyl)-carboxylic-carboxylic acid tert-butyl ester To a 100-mL round-bottomed flask containing 3(R,S)-carboxymethyl-4-(3-trifluoromethyl-benzenesulfonyl)-car boxylic-carboxylic acid tert-butyl ester [0.30 g, 0.66 mmol, step (b)] in DMF (8 mL), was added 5(R)-amino-5,6,7,8-tetrahydro-naphthalen-2-yl)-methanol (0.12 g, 0.66 mmol) HATU (0.88 g, 2.3 mmol, PerSeptive Biosystem) and DIEA (0.40 mL, 2.3 mmol, Aldrich). The mixture was stirred at RT for 20 h. The reaction was quenched with water (10 mL) and the compound was extracted with EtOAc (2×20 mL). The organic phase was washed with 5% brine (2×10 mL), dried over Na$_2$SO$_4$, filtered, and concentrated. Purification with column chromatography over silica gel with hexane:EtOAc (1:1) gave the title compound as a clear oil. MS (ESI, pos. ion.) m/z: 612 (M+1).

D) Preparation of 3(R,S)-[6-formyl-1,2,3,4-tetrahydronaphthalen-1(R)-ylcarbamoyl)-methyl]-4-(3-trifluoromethyl-benzenesulfonyl)-carboxylic-carboxylic acid tert-butyl ester To a 100-mL round-bottomed flask containing 3(R,S)-[6-hydroxymethyl-1,2,3,4-tetrahydronaphthalen-1(R)-ylcarbamoyl)-methyl]-4-(3-trifluoromethyl-benzenesulfonyl)-carboxylic-carboxylic acid tert-butyl ester [0.39 g, 0.64 mmol, step (c)] in CH$_2$Cl$_2$ (10 mL), was added MnO$_2$ (0.83 g, 9.6 mmol, Aldrich). The reaction was stirred at RT for 3 h. After filtration through Celite®, the solution was concentrated in vacuo to give the title compound as a white powder. MS (ESI, pos. ion.) m/z: 611 (M+1).

E) Preparation of 3(R,S)-{[6-(tert-Butylamino-methyl)-1,2,3,4-tetrahydro-naphthalen-1(R)-ylcarbamoyl]-methyl}-4-(3-trifluoromethyl-benzenesufonyl)-piperazine-1-carboxylic acid tert-butyl ester To a 50-mL reaction tube containing 3(R,S)-[6-formyl-1,2,3,4-tetrahydronaphthalen-1(R)-ylcarbamoyl)-methyl]-4-(3-trifluoromethyl-benzenesulfonyl)-carboxylic-carboxylic acid tert-butyl ester [0.35 g, 0.58 mmol, step (d)] in DMF (10 µL), was added tert-butylamine (0.61 mL, 5.8 mmol, Aldrich) and AcOH (33 µL, 0.58 mmol). The reaction tube was sealed and the mixture was stirred at 55° C. for 1 h. After cooling to RT, NaBH(OAc)$_3$ (0.35 g, 2.88 mmol, Aldrich) was added and the mixture was stirred at RT overnight. The reaction was quenched with 5% brine (5 mL) and the compound was extracted with EtOAc (2×5 mL). The organic phase was washed with 5% brine (2×5 mL), dried over Na$_2$SO$_4$, filtered, and concentrated. Column chromatography over silica gel with hexane:EtOAc:MeOH (5:5:1) gave the title compound as clear oil. MS (ESI, pos. ion.) m/z: 667 (M+1).

EXAMPLE 17

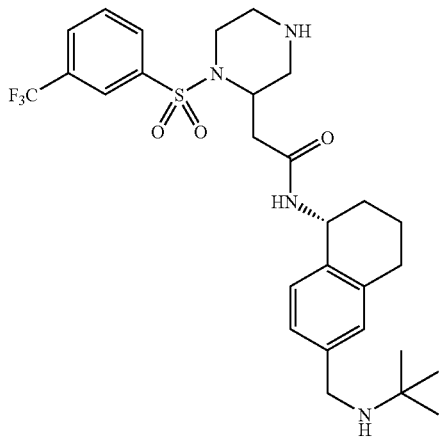

N-[6-(tert-Butylamino-methyl)-1,2,3,4-tetrahydro-naphthalen-1(R)-yl]-2-[1-(3-trifluoromethyl-benzenesufonyl)-piperazin-2(R,S)-yl-acetamide.

To a 50-mL round-bottomed flask was added 3(R,S)-{[6-(tert-butylamino-methyl)-1,2,3,4-tetrahydro-naphthalen-1(R)-ylcarbamoyl]-methyl}-4-(3-trifluoromethyl-benzenesufonyl)-piperazine-1-carboxylic acid tert-butyl ester (33 mg, 0.050 mmol, Example 16) and HCl (1.5 mL, 6.0 mmol, 4.0 M in 1,4-dioxane, Aldrich) and MeOH (2 mL). The reaction was stirred at RT for 1 h. The solution was concentrated in vacuo to give the compound as a white solid. MS (ESI, pos. ion.) m/z: 567(M+1).

EXAMPLE 18

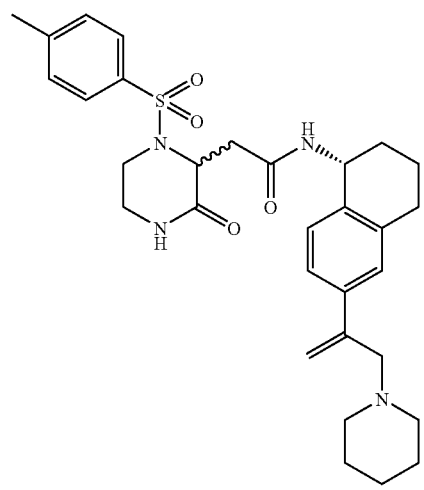

2-[3-Oxo-1-(toluene-4-sulfonyl)-piperazin-2-yl]-N-[6-(1-piperidin-1-ylmethyl-vinyl)-1,2,3,4-tetrahydro-naphthalen-1(R)-yl]-acetamide A) Preparation of trifluoro-methanesulfonic acid 5-oxo-5,6,7,8-tetrahydro-naphthalen-2-yl ester To a 1 L round-bottomed flask charged with 6-hydroxy-1-tetralone (Aldrich, 21.97 g, 0.136 mol) at 0° C. was added CH$_2$Cl$_2$ (500 mL) and pyridine (Aldrich, 11 mL, 0.136 mmol). Triflic anhydride (Aldrich, 23 mL, 0.136 mmol) was added through an additional funnel over a period of 12 min. The mixture was gradually warmed to RT and stirred at RT overnight. The residue was diluted with water and two phases were separated. The organic phase was washed with 1 N HCl (100 mL×2), sat NaHCO$_3$, and brine, dried over Na$_2$SO$_4$. After filtration and concentration in vacuo, the crude was purified by flash chromatography (5-11% EtOAc-hexane) to provide the title compound as yellow oil. MS (ESI): 295 (M+H)$^+$.

B) Preparation of trifluoro-methanesulfonic acid 5(S)-hydroxy-5,6,7,8-tetrahydro-naphthalen-2-yl ester To a dry three-necked flask containing (R)-2-methyl-CBS-oxazaborolidine (Aldrich, 1.94 mL, 1.0 M in toluene, 1.93 mmol, 0.05 eq) under $N_2$ was added a solution of $BH_3$-$Me_2S$ (Aldrich, 3.30 mL, 34.80 mmol, 0.9 eq) in toluene (200 mL) through an addition funnel. After the addition, the reaction was cooled to 0° C. A solution of trifluoro-methanesulfonic acid 5-oxo-5,6,7,8-tetrahydro-naphthalen-2-yl ester (step a, 11.37 g, 38.67 mmol, 1.0 eq) in THF (180 mL) was added drop-wise through an addition funnel. Following the addition, the reaction mixture was stirred at RT for 40 min, then quenched with MeOH. The solvent was removed in vacuo and the crude was diluted with $H_2O$ (50 mL). The aqueous phase was extracted with ether (3×150 mL). The combined organic layer was washed with brine, dried over $Na_2SO_4$, filtered and concentrated. The title compound was obtained as an off-white solid by flash chromatography (16-22% EtOAc-hexane).

C) Preparation of trifluoro-methanesulfonic acid 5(R)-azido-5,6,7,8-tetrahydro-naphthalen-2-yl ester To a solution of trifluoro-methanesulfonic acid 5-hydroxy-5,6,7,8-tetrahydro-naphthalen-2-yl ester (Step b, 11.2 g, 37.9 mmol, 1.0 eq) in THF (150 mL) at RT was added DPPA (Aldrich, 11.1 mL, 51.6 mmol, 1.36 eq). The resulting mixture was cooled to 0° C. and DBU (Aldrich, 7.7 mL, 51.6 mmol, 1.36 eq) was added slowly through a syringe. The mixture was warmed to RT and stirred over the weekend. The reaction was concentrated in vacuo. The crude compound was dissolved in EtOAc (400 mL). The organic layer was washed with $NH_4Cl$ (twice), $H_2O$, and brine, dried over $Na_2SO_4$. After filtration and concentration in vacuo, the crude was purified by flash chromatography (5% EtOAc-hexane) to provide the title compound.

D) Preparation of trifluoro-methanesulfonic acid 5(R)-amino-5,6,7,8-tetrahydro-naphthalen-2-yl ester To a solution of trifluoro-methanesulfonic acid 5-azido-5,6,7,8-tetrahydro-naphthalen-2-yl ester (step c, 10.3 g, 32.1 mmol, 1.0 eq) in THF (70 mL) was added $PPh_3$ (Aldrich, 8.4 g, 32.1 mmol, 1.0 eq), and $H_2O$ (30 mL) at 0° C. The mixture was warmed to RT and stirred overnight. 2 N HCl was added until the mixture was acidic (pH=1-2). The mixture was extracted with toluene (3×100 mL). The aqueous phase was neutralized with 5N NaOH until the pH=12-13, extracted with $Et_2O$ (3×150 μL). The ether solution was dried over $Na_2SO_4$, filtered and concentrated in vacuo. The crude was purified by flash chromatography (6% MeOH-$CH_2Cl_2$) to provide the title compound.

E) Preparation of trifluoro-methanesulfonic acid 5 (R)-tert-butoxycarbonylamino-5,6,7,8-tetrahydro-naphthalen-2-yl ester To a solution of trifluoro-methanesulfonic acid 5 (R)-amino-5,6,7,8-tetrahydro-naphthalen-2-yl ester (Step d, 2.0 g, 6.8 mmol, 1.0 eq) in $CH_2Cl_2$ (20 mL) was added $Et_3N$ (1.9 mL, 13.6 mmol, 2.0 eq) and di-tert-butyl carbonate (Aldrich, 1.8 g, 8.1 mmol, 1.2 eq). The mixture was stirred at RT overnight, washed with saturated $NaHCO_3$ (2×20 mL) and brine, and dried over $Na_2SO_4$. After filtration and concentration in vacuo, the crude was purified by flash chromatography (4-10% EtOAc-hexane) to provide the title compound as a white solid.

F) Preparation of [6-(1-piperidin-1-ylmethyl-vinyl)-1,2,3,4-tetrahydro-naphthalen-1(R)-yl]-carbamic acid tert-butyl ester To a solution of trifluoro-methanesulfonic acid 5-tert-butoxycarbonylamino-5,6,7,8-tetrahydro-naphthalen-2-yl ester (Step e, 1.89 g, 4.79 mmol, 1.0 eq) in $CH_3CN$ (25 mL) purged with $N_2$ was added palladium (II) acetate (Strem Chemicals, 65 mg, 0.29 mmol, 0.06 eq), 1,1'-bis(diphenylphosphino)ferrocene (Aldrich, 0.70 g, 1.26 mmol, 0.26 eq), $K_2CO_3$ (0.99 g, 7.18 mmol, 1.5 eq) and N-allyl piperidine (Lancaster, 3.00 g, 23.96 mmol, 5.0 eq). The vessel was sealed with a septum and heated to 80° C. overnight. After cooling to RT, the mixture was diluted with $H_2O$, and extracted with $Et_2O$ (3×). The ether solution was dried over $Na_2SO_4$, filtered and concentrated in vacuo. The crude was purified by flash chromatography (14-21% EtOAc-Hexane) to provide the title compound.

MS (ESI): 371(M+H)$^+$.

G) Preparation of 6-(1-piperidin-1-ylmethyl-vinyl)-1,2,3,4-tetrahydro-naphthalen-1(R)-ylamine To a solution of [6-(1-piperidin-1-ylmethyl-vinyl)-1,2,3,4-tetrahydro-naphthalen-1(R)-yl]-carbamic acid tert-butyl ester in $CH_2Cl_2$ (3 mL) was added TFA (3 mL). The mixture was stirred at RT for 4 h, concentrated in vacuo. The crude was neutralized with 10% $Na_2CO_3$ until the aqueous phase was basic, then extracted with $CH_2Cl_2$ three times. The organic solution was washed with brine, dried over $Na_2SO_4$, filtered and concentrated in vacuo to provide the title compound. MS (ESI): 271 (M+H)$^+$.

H) Preparation of 2-[3-oxo-1-(toluene-4-sulfonyl)-piperazin-2-yl]-N-[6-(1-piperidin-1-ylmethyl-vinyl)-1,2,3,4-tetrahydro-naphthalen-1(R)-yl]-acetamide To a 20 mL flask equipped with stirring was added [3-oxo-1-(toluene-4-sulfonyl)-piperazin-2-yl]-acetic acid (104 mg, 0.33 mmol), 6-(1-piperidin-1-ylmethyl-vinyl)-1,2,3,4-tetrahydro-naphthalen-1(R)-ylamine (Step g, 90 mg, 0.33 mmol), EDC (Aldrich, 96 mg, 0.50 mmol), HOBt (Aldrich, 45 mg, 0.33 mmol), and $CH_2Cl_2$ (2 mL). The reaction mixture was stirred at RT overnight and diluted with $CH_2Cl_2$ (50 mL). The organic phase was washed with saturated $NaHCO_3$ and brine, dried over $Na_2SO_4$, filtered and concentrated in vacuo. The crude was purified by preparative TLC in 10% MeOH-$CH_2Cl_2$ to afford the title compound as a mixture of two diastereomers. MS (ESI): 565 (M+H)$^+$.

EXAMPLE 19

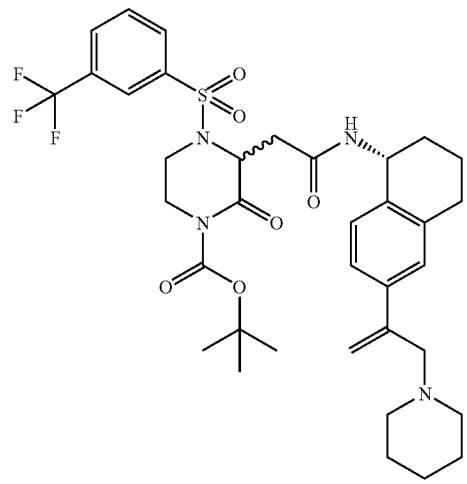

3-{[6-(1-Piperidin-1-ylmethyl-vinyl)-1,2,3,4-tetrahydro-naphthalen-1(R)-ylcarbamoyl]-methyl}-4-(3-trifluoromethyl-benzenesulfonyl)-piperazine-1-carboxylic acid tert-butyl ester 3-{[6-(1-Piperidin-1-ylmethyl-vinyl)-1,2,3,4-tetrahydro-naphthalen-1(R)-ylcarbamoyl]-methyl}-4-(3-trifluoromethyl-benzenesulfonyl)-piperazine-1-carboxylic acid tert-butyl ester was prepared from 3-carboxymethyl-4-(3-trifluoromethyl-benzenesulfonyl)-piperazine-1-carboxylic acid tert-butyl ester using essentially the same procedure described in Example 18 yielding a light yellow solid. MS (ESI): 705 (M+H)+.

EXAMPLE 20

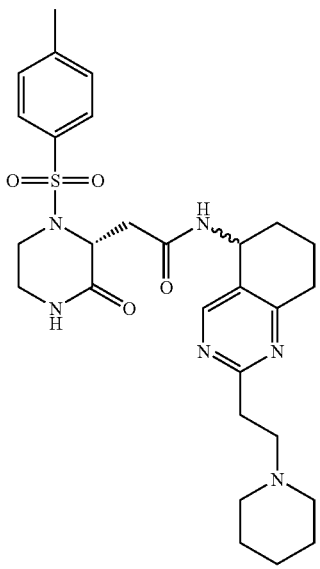

(R)-2-(3-oxo-1-tosylpiperazin-2-yl)-N-(2-(2-(Piperidin-1-yl)ethyl)-5,6,7,8-tetrahydroquinazolin-5-yl) acetamide A. Preparation of 3-(tert-butyldiphenyl-silyloxy)propanenitrile.

To a solution of 3-hydroxypropanenitrile (7.1 g, 0.1 mol) and DMAP (1.22 g, 0.01 mmol) in 30 mL of dry DCM at room temperature was added NEt3 (30.3 g, 0.3 mol), followed by tert-butyldiphenyl-silylchloride (27.5 g, 0.1 mol). A lot of white solid appeared. After stirring at room temperature overnight, the reaction mixture was quenched with Sat. NH$_4$Cl solution, extracted with DCM, dried over Na2SO4, and evaporated in vaco. Flash chromatography (SiO2, hexane/EtOAc=100:2 to 100:5 to 100:10) gave the title compound as a white solid.

B. Preparation 3-(tert-butyldiphenylsilyloxy)propanamidine.

To a suspension of NH$_4$Cl (5.35 g, 0.1 mol) in 60 mL of dry benzend at 0 C was slowly added 50 mL of 2 M solution of trimethylaluminum in toluene. After the addition was complete, the reaction mixture was allowed to warm up to room temperature and was stirred for 2 h until gas evolution had ceased. A solution of the above nitrile in 20 mL of dry benzene was added to the aluminum amide reagent and the resulting mixture was heated up to 80 C for 20 h. The reaction mixture was slowly cooled to room temperature and then carefully poured into a slurry of 300 mL of DCM and 200 g of silica gel. It was then filtered and washed thoroughly with MeOH/DCM (1:2). After concentration, flash chromatography (SiO2, EtOAc to EtOAc/MeOH=100:20 to 100:30 to EtOAc/2 m NH$_3$ in MeOH=100:30) gave the product as a white solid.

C. Preparation of 3-(tert-butyldiphenylsilyloxy)propanamidine2-(2-(tert-butyldiphenylsilyloxy)ethyl)-7,8-dihydroquinazolin-5(6H)-one.

A Solution of 3-(tert-butyldiphenylsilyloxy) propanamidine (25 g, 77 mmol) and 2-((dimethylamino)methylene)cyclohexane-1,3-dione (12.8 g, 77 mmol) in 400 mL of dry EtOH was heated at 80° C. for 3 h. After cooling to room temperature, the solvent was evaporated. Flash chromatography (SiO$_2$, EtOAc/hexane=1:1) gave the title compound as a white solid.

D. Preparation of 2-(2-(tert-butyldiphenylsilyloxy)ethyl)-5,6,7,8-tetrahydro-quinazolin-5-ol.

A solution of the above ketone (2.16 g, 5 mmol) in 30 mL of dry MeOH was treated with NaBH$_4$ (189 mg, 5 mmol). After 5 min, the reaction was quenched with 5 mL of Sat. NH$_4$Cl solution. The MeOH was evaporated and the residue was extracted with DCM, dried over Na$_2$SO$_4$ and evaporated. Flash chromatography (SiO$_2$, DCM to EtOAc) gave the title compound as a white solid.

E. Preparation of 5-azido-2-(2-(tert-butyldiphenyl silyloxy) ethyl)-5,6,7,8-tetrahydroquinazoline.

To a solution of the above product (2.0 g, 4.63 mmol) in 25 mL of toluene at −10° C. was added DPPA (1.2 mL, 5.56 mmol). To this stirred solution was then added DBU (0.83 mL, 5.56 mmol) dropwise while keeping the temperature below 0° C. After stirring at room temperature for 16 h, the reaction was evaporated to dryness and directly submitted to flash chromatography (SiO$_2$, hexane/DCM=1:2) to afford the azide as a white solid.

F. Preparation of 2-(2-(tert-butyldiphenylsilyloxy)ethyl)-5,6,7,8-tetrahydro-quinazolin-5-amine.

A suspension of 80 mg of Pd/C (10% w/w) in a solution of the above azide (800 mg, 1.75 mmol) in 30 mL of EtOAc was stirred under H$_2$ atomosphere overnight. The reaction mixture was then directly submitted to flash chromatograph (SiO$_2$, EtOAc to EtOAc/MeOH=100:15 to EtOAc/2M NH$_3$ in MeOH=2:1) to give the amine (570 mg, 76%) as a white solid.

G. Preparation of 2-(5-amino-5,6,7,8-tetrahydroquinazolin-2-yl)ethanol.

A solution of the above product (570 mg, 1.32 mmol) in 10 mL of THF at 0° C. was treated with a 1M TBAF solution in THF (1.56 mL, 1.56 mmol). After stirring at room temperature overnight, the reaction mixture was directly submitted to flash chromatograph (SiO$_2$, EtOAc to EtOAc/MeOH=100:15 to EtOAc/2M NH$_3$ in MeOH=1:1) to the title compound as a white solid.

H. Preparation of(R)-N-(2-(2-hydroxyethyl)-5,6,7,8-tetrahydroquinazolin-5-yl)-2-(3-oxo-1-tosylpiperazin-2-yl)acetamide.

A solution of (R)-2-(3-oxo-1-tosylpiperazin-2-yl)acetic acid (1.55 g, 5.0 mmol), crude $^2$-(5-amino-5,6,7,8-tetrahydroquinazolin-2-yl)ethanol (966 mg, 5.0 mmol), HOBt (676 mg, 5.0 mmol) and EDCI (959 mg, 5.0 mmol) in 2.5 mL of DMF was stirred overnight at room temperature. After quenching with Sat. NaHCO$_3$ solution, the reaction mixture was extracted with EtOAc. The combined organic phase was washed brine, dried over Na$_2$SO$_4$, and evaporated in vaco. Flash chromatography (SiO$_2$, EtOAc/MeOH=100:15 to 100:20 to 100:25 to 100:30) gave the title compound as a white solid.

I. Preparation of (R)-2-(5-(2-(3-oxo-1-tosylpiperazin-2-yl)acetamido)-5,6,7,8-tetrahydroquinazolin-2-yl)ethyl methanesulfonate.

To a solution of the product from the previous step (1.22 g, 2.5 mmol) in dry DCM at 0° C. was added MsCl (860 mg, 7.5 mmol), followed by NEt₃ (1.25 g, 12.5 mmol). After stirring at 0° C. for 20 min, the reaction mixture was quenched with sat. NaHCO₃ solution, extracted with EtOAc, dried over Na₂SO₄, and evaporated in vaco. Flash chromatography (SiO₂, EtOAc/MeOH=100:10 to 100:15 to 100:16 to 100:18) gave the title compound as a white solid. MS: 566.2 (M+1).

J. Preparation of (R)-2-(5-(2-(3-oxo-1-tosylpiperazin-2-yl)acetamido)-5,6,7,8-tetrahydroquinazolin-2-yl)ethyl methanesulfonate A solution of (R)-2-(5-(2-(3-oxo-1-tosylpiperazin-2-yl)acetamido)-5,6,7,8-tetrahydroquinazolin-2-yl)ethyl methanesulfonate (565 mg, 1.0 mmol) and piperidine (170 mg, 2.0 mmol) in dry DCM at room temperature was stirred overnight. The reaction mixture was quenched with sat. NH₄Cl solution, extracted with EtOAc, wasched with water, dried over Na₂SO₄, and evaporated in vaco. Flash chromatography (SiO₂, EtOAc/MeOH=100:15 to 100:20 to EtOAc/2M NH₃ in MeOH=100:15 to 100:20 to 100:30) gave the title compound as a white solid. MS: 555.2 (M+1).

EXAMPLE 21

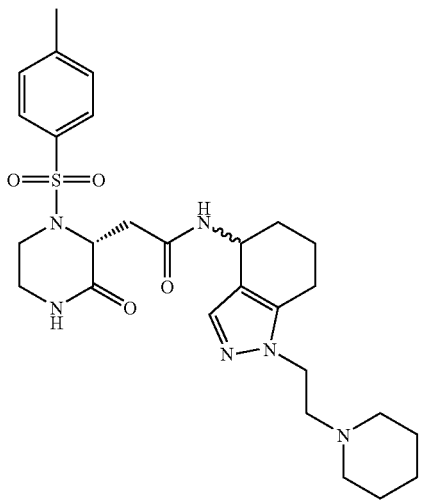

(R)-2-(3-oxo-1-tosylpiperazin-2-yl)-N-(1-(2-(piperidin-1-yl)ethyl)-4,5,6,7-tetrahydro-1H-indazol-4-yl)acetamide A. Preparation of 1-(2-hydroxyethyl)-6,7-dihydro-1H-indazol-4(5H)-one.

2-hydroxyethyl hydrazine (1.36 mL, 20 mmol) was slowly added to an ice-cooled solution of 2-((dimethylamino)methylene)cyclohexane-1,3-dione (3.34 g) in methanol (50 mL). After stirring at room temperature for 20 min, the solvent was evaporated. Flash chromatography (SiO₂, EtOAc/MeOH=100:5 to 100:7 to 100:10) gave the title compound as a white solid.

B. Preparation of 1-(2-(tert-butyldimethylsilyloxy)ethyl)-6,7-dihydro-1H-indazol-4(5H)-one.

To a solution of the product from step A (14 g, 77.8 mmol) in 100 mL of dry DCM was added NEt₃ (22 mL, 155.6 mmol), followed by TBSCl (14 g, 93.3 mmol) and DMAP (95 mg, 0.78 mmol). After stirring at room temperature overnight, the reaction was quenched with brine and extracted with EtOAc. Flash chromatography (SiO₂, EtOAc/hexane=1:1) gave the title compound as a white solid.

C. Preparation of 1-(2-(tert-butyldimethylsilyloxy)ethyl)-4,5,6,7-tetrahydro-1H-indazol-4-ol A solution of the product of step B (21 g, 71.4 mmol) in 200 mL of dry MeOH was treated with NaBH4 (2.7 g, 71.4 mmol). After 30 min, the reaction was quenched with 15 mL of Sat. NH₄Cl solution. The MeOH was evaporated and the residue was extracted with EtOAc, dried over Na₂SO₄ and evaporated. Flash chromatography (SiO₂, EtOAc/hexane=1:1 to EtOAc) gave the title compound as a white solid.

D. Preparation of 4-azido-1-(2-(tert-butyldimethyl silyloxy)ethyl)-4,5,6,7-tetrahydro-1H-indazole.

To a solution of the above alcohol (23 g, 77.7 mmol) in 200 mL of toluene at −10° C. was added DPPA (20 mL, 93.2 mmol). To this stirred solution was then added DBU (13.9 mL, 93.2 mmol) dropwise while keeping the temperature below 0° C. After stirring at room temperature for 18 h, the reaction was evaporated to dryness and directly submitted to flash chromatography (SiO₂, hexane/EtOAc=2:1 to EtOAc) to afford the title compound as a colorless liquid, together with 12 g of recovered starting alcohol.

E. Preparation of 1-(2-(tert-butyldimethylsilyloxy)ethyl)-4,5,6,7-tetrahydro-1H-indazol-4-amine.

A suspension of 150 mg of Pd/C (10% w/w) in a solution of the product from step D (2.0 g, 6.23 mmol) in 100 mL of EtOAc was stirred under H₂ atomosphere overnight. The reaction mixture was then directly submitted to flash chromatograph (SiO₂, EtOAc to EtOAc/MeOH=100:20 to EtOAc/2M NH₃ in MeOH=100:20 to 100:30 to 100:40) to give the title compound as a white solid.

F. Preparation of (R)-N-(1-(2-(tert-butyldimethylsilyloxy)ethyl)-4,5,6,7-tetrahydro-1H-indazol-4-yl)-2-(3-oxo-1-tosylpiperazin-2-yl)acetamide.

A solution of (R)-2-(3-oxo-1-tosylpiperazin-2-yl)acetic acid (624 mg, 2.0 mmol), 1-(2-(tert-butyldimethylsilyloxy)ethyl)-4,5,6,7-tetrahydro-1H-indazol-4-amine (649 mg, 2.2 mmol), HOBt (297 mg, 2.2 mmol) and EDCI (422 mg, 2.2 mmol) in 1.2 mL of DMF was stirred overnight at room temperature. After quenching with Sat. NaHCO₃ solution, the reaction mixture was extracted with EtOAc. The combined organic phase was washed brine, dried over Na₂SO₄, and evaporated in vaco. Flash chromatography (SiO₂, EtOAc/MeOH=100:4 to 100:8 to 100:10 to 100:15) gave the title compound as a white solid. MS: 590.2 (M+1).

G. Preparation of (R)-N-(1-(2-hydroxyethyl)-4,5,6,7-tetrahydro-1H-indazol-4-yl)-2-(3-oxo-1-tosylpiperazin-2-yl)acetamide.

A solution of the product from step F (810 mg, 1.375 mmol) in 15 mL of THF at 0° C. was treated with HOAc (991 mg, 16.5 mmol) followed by a 1.0M solution of TBAF in THF (5.5 mL, 5.5 mmol). After stirring at room temperature overnight, the reaction mixture was evaporated to dryness and was directly submitted to flash chromatograph (SiO₂, EtOAc to EtOAc/MeOH=100:15 to 100:18 to 100:20 to 100:25 to 100:30) to give the title compound as a white solid. MS: 476.2 (M+1).

H. Preparation of (R)-2-(4-(2-(3-oxo-1-tosylpiperazin-2-yl)acetamido)-4,5,6,7-tetrahydroindazol-1-yl)ethyl methanesulfonate.

To a solution of the product of step G (900 mg, 1.89 mmol) in dry DCM at 0° C. was added MsCl (0.44 mL, 5.68 mmol), followed by NEt$_3$ (1.3 mL, 9.45 mmol). After stirring at 0° C. for 15 min, the reaction mixture was quenched with sat. NaHCO$_3$ solution, extracted with EtOAc, dried over Na$_2$SO$_4$, and evaporated in vaco. Flash chromatography (SiO$_2$, EtOAc/MeOH=100:12 to 100:15 to 100:18 to 100:20 to 100:25 to 100:30) gave the crude product as a white solid.

I. Preparation of((R)-2-(3-oxo-1-tosylpiperazin-2-yl)-N-(1-(2-(piperidin-1-yl)ethyl)-4,5,6,7-tetrahydro-1H-indazol-4-yl)acetamide.

A solution of the product of step H (220 mg, 0.4 mmol) and piperidine (135 mg, 1.6 mmol) in dry DCM at room temperature was stirred overnight. The reaction mixture was quenched with Sat. NH$_4$Cl solution, extracted with EtOAc, wasched with water, dried over Na$_2$SO$_4$, and evaporated in vaco. Flash chromatography (SiO$_2$, EtOAc/MeOH=100:15 to 100:20 to EtOAc/2M NH$_3$ in MeOH=100:15 to 100:20 to 100:25) gave the title compound as a white solid.

MS: 543.2 (M+1).

EXAMPLE 22

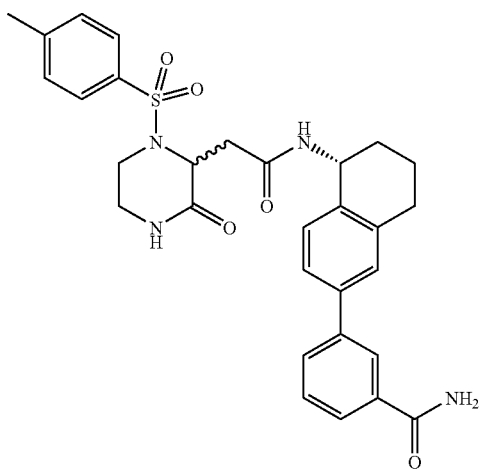

3-((5R)-5-(2-(3-oxo-1-tosylpiperazin-2-yl)acetamido)-5,6,7,8-tetrahydronaphthalen-2-yl)benzamide Preparation of -3-((5R)-5-(2-(3-oxo-1-tosylpiperazin-2-yl)acetamido)-5,6,7,8-tetrahydronaphthalen-2-yl)benzamide To a 25 mL pressure tube was added (R)-5-(2-(3-oxo-1-tosylpiperazin-2-yl)acetamido)-5,6,7,8-tetrahydronaphthalen-2-yl trifluoromethanesulfonate (150 mg, 0.25 mmol), benzamide-3-boronic acid (Frontier, 63 mg, 0.38 mmol), tetrakis(triphenylphosphine)-palladium (O) (Aldrich, 30 mg, 0.025 mmol), Toluene (1.5 mL), EtOH (0.4 μL), and 1M NaHCO$_3$ (0.4 mL) at room temperature under N$_2$. The reaction mixture was sealed and stirred at 80° C. overnight, cooled to room temperature, and diluted with EtOAc (40 mL). The organic layer was separated, washed with saturated NaHCO$_3$, water and brine, dried over Na$_2$SO$_4$, filtered and concentrated in vacuo. The residue was purified by silica gel chromatography to provide the title compound. MS (ES1): 561 (M+H)$^+$.

EXAMPLE 23

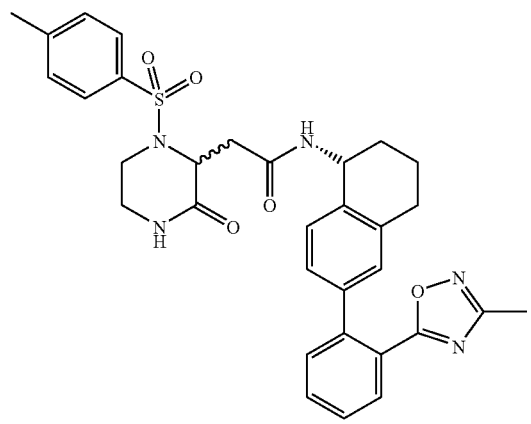

N-((1R)-6-(2-(3-methyl-1,2,4-oxadiazol-5-yl)phenyl)-1,2,3,4-tetrahydronaphthalen-1-yl)-2-(3-oxo-1-tosylpiperazin-2-yl)acetamide A. Preparation of tert-butyl (1R)-6-(2-(hydroxymethyl)phenyl)-1,2,3,4-tetrahydronaphthalen-1-ylcarbamate To a 150 mL sealed tube was added (R)-5-(tert-butoxycarbonyl)-5,6,7,8-tetrahydronaphthalen-2-yl trifluoromethanesulfonate (1.0 g, 3.38 mmol) followed by (2-hydroxymethylphenyl)boronic acid (677.0 mg, 5.05 mmol), Pd(PPh$_3$)$_4$ (292.0 mg, 0.253 mmol), EtOH (5 mL), NaHCO$_3$ (1M, 5 mL) and toluene (20 mL). The resulting mixture was capped and heated at 80° C. for 20 h. The solution mixture was partitioned between EtOAc and H$_2$O. The organic layer was washed with brine, dried over MgSO$_4$, and removed solvent. The residue was purified by chromatography on silica gel. Elution with Hex:EtOAc mixture (80:20) gave title compound. MS m/z: 354.3 (M+H). Calc'd. for C$_{22}$H$_{27}$NO$_3$-353.47.

B. Preparation of 2-((5R)-5-(tert-butoxycarbonyl)-5,6,7,8-tetrahydronaphthalen-2-yl)benzoic acid.

To a 100 mL round bottom flask was added (tert-butyl (1R)-6-(2-(hydroxymethyl)phenyl)-1,2,3,4-tetrahydronaphthalen-1-ylcarbamate (200.0 mg, 0.565 mmol) followed by CCl$_4$ (2 mL), MeCN (2 mL), H$_2$O (3 mL), NaIO$_4$ (363.0 mg, 1.70 mmol), and RuCl$_3$ (hydrate, 6 mg, 0.0289 mmol) The resulting mixture was capped and stirred at rt for 2 h. The solution mixture was partitioned between EtOAc and H$_2$O. The organic layer was separated from the RuCl$_3$ by passing through the celite. The organic layer was dried over MgSO$_4$ and removed solvent. The residue was purified by chromatography on silica gel. Elution with CH$_2$Cl$_2$:MeOH mixture (95:5) gave title compound. MS m/z: 368.4 (M+H). Calc'd. for C$_{22}$H$_{25}$NO$_4$-367.45.

C. Preparation of tert-butyl (1R)-6-(2-(chlorocarbonyl)phenyl)-1,2,3,4-tetrahydronaphthalen-1-ylcarbamate To a 100 mL round bottom flask was added 2-((5R)-5-(tert-butoxycarbonyl)-5,6,7,8-tetrahydronaphthalen-2-yl)benzoic acid (270.0 mg, 0.735 mmol) followed by CH$_2$Cl$_2$ (15 mL), oxalyl chloride (0.7 mL, 1.5 mmol), and DMF (2 drops). The resulting mixture was stirred at rt for 3 h. The solution mixture was evaporated all solvent off to dryness to give title compound. MS m/z: 386.4 (M+H). Calc'd. for $C_{22}H_{24}ClNO_3$-385.89.

D. Preparation of tert-butyl (1R)-6-(2-(3-methyl-1,2,4-oxadiazol-5-yl)phenyl)-1,2,3,4-tetrahydronaphthalen-1-ylcarbamate To a 100 mL round bottom flask was added tert-butyl (1R)-6-(2-(chlorocarbonyl)phenyl)-1,2,3,4-tetrahydronaphthalen-1-ylcarbamate (150.0 mg, 0.388 mmol) followed by dry $CH_2Cl_2$ (15 mL), $NEt_3$ (0.11 mL, 1.3 mmol), and acetamide (86 mg, 1.17 mmol). The resulting mixture was stirred at rt for 20 h. Removed solvent to dryness. Added toluene (15 mL) and heated at 115° C. for 20 h. Solvent was removed. The residue was purified by chromatography on silica gel. Elution with $CH_2Cl_2$:MeOH mixture (95:5) gave title compound (75 mg, 48%). MS m/z: 406.2 (M+H). Calc'd. for $C_{24}H_{27}N_3O_3$-405.3.

E. (1R)-6-(2-(3-methyl-1,2,4-oxadiazol-5-yl)phenyl)-1,2,3,4-tetrahydronaphthalen-1-amine.

To a solution of the product of step D (75 mg, 0.184 mmol) in anhydrous ethyl acetate (100 mL) was added 20 mL of 4 N HCl in dioxane the resulting mixture was stirred at RT for 3 h then evaporated to afford the title compound as a colorless glass.

MS m/z: 306.2 (M+H). Calc'd. for $C_{19}H_{19}N_3O$-305.3.

F. Preparation of N-((1R)-6-(2-(3-methyl-1,2,4-oxadiazol-5-yl)phenyl)-1,2,3,4-tetrahydronaphthalen-1-yl)-2-(3-oxo-1-tosylpiperazin-2-yl)acetamide To a 100 mL round bottom flask was added (1R)-6-(2-(3-methyl-1,2,4-oxadiazol-5-yl)phenyl)-1,2,3,4-tetrahydronaphthalen-1-amine (25.0 mg, 0.06 mmol), followed by 2-(3-oxo-1-tosylpiperazin-2-yl)acetic acid (50 mg, 0.016 mmol), dry $CH_2Cl_2$ (10 mL), HATU (12 mg, 0.03 mmol), EDCI (13 mg, 0.068 mmol) and hunig base (0.022 mL, 0.123 mmol). The resulting mixture was stirred at rt for 20 h. Removed solvent to dryness. Solvent was removed. The residue was purified by chromatography on silica gel. Elution with $CH_2Cl_2$:MeOH mixture (97:3) gave final compound. MS m/z: 600.3 (M+H). Calc'd. for $C_{32}H_{33}N_5O_5S$ -599.71.s A. Preparation of Diethyl 3-(2-aminoethylamino)pentanedioate.

To ethylenediamine (13.0 ml, 194 mmol) under $N_2$ was added diethyl glutaconate (3.40 ml, 19.2 mmol) over 5 min. After 15 min, the mixture was concentrated under reduced pressure and dried in vacuo to yield the title compound. MS: 247.2

B. Preparaton of Ethyl 2-(7-oxo-4-tosyl-1,4-diazepan-5-yl)acetate.

A solution of the product of step A (1.34 g, 5.44 mmol) was stirred in THF (30 ml) at 0*C. $Bu_3SnOTf$ (90%, 2.73 g, 5.60 mmol) in THF 8.0 ml was added dropwise over 6 min, and the mixture was heated to reflux for 22 h. The reaction was cooled to 0° C., and triethylamine (1.52 ml, 10.9 mmol) and dimethylaminopyridine (0.135 g, 1.11 mmol) were added followed by p-toluenesulfonyl chloride (2.09 g, 11.0 mmol) in THF 4.0 ml. The reaction was allowed to r.t. and after 4 h concentrated under reduced pressure. AcOEt (100 ml) was added to the residue and washed with 0.1 N HCl aq. (100 ml×2), sat'd $NaHCO_3$ aq. (100 ml×2) and sat'd NaCl aq. (100 ml×2), dried over $Na_2SO_4$ and concentrated under reduced pressure. The crude product was chromatographed on silica (AcOEt→AcOEt/-MeOH=80/1) to yield the title compound. MS:355.2

C. 2-(7-Oxo-4-tosyl-1,4-diazepan-5-yl)acetic acid (3)

To a solution of the product of step B (0.416 g, 1.17 mmol) in 1,4-dioxane (24 ml) and MeOH (24 ml), 0.13 N LiOH (28 ml, 3.6 mmol) was added, and the mixture was heated to reflux for overnight. The reaction was cooled to r.t. and AcOEt (400 ml) was added and washed with sat'd NaCl (400 ml×5), dried over $Na_2SO_4$ and concentrated under reduced pressure to yield the title compound. MS: 327.1

D. (R)-2-(7-Oxo-4-tosyl-1,4-diazepan-5-yl)-N-(6-(piperidin-1-ylmethyl)-1,2,3,4-tetrahydronaphthalen-1-yl)acetamide.

To a mixture of 2-(7-oxo-4-tosyl-1,4-diazepan-5-yl)acetic acid (0.115 g, 0.352 mmol), (R)-6-(piperidin-1-ylmethyl)-1,2,3,4-tetrahydronaphthalen-1-amine (0.0945 g, 0.387 mmol) and HOBt (<5% $H_2O$, ~0.398 mmol) in DMF (3.0 ml) was added EDCI*HCl (0.0805 g, 0.420 mmol), and stirred overnight under $N_2$. AcOEt (60 ml) was added and washed with sat'd $NaHCO_3$ aq. (60 ml×3) and sat'd NaCl aq. (60 ml×3), dried over $Na_2SO_4$ and concentrated under reduced pressure. The crude product was chromatographed on silica ($CH_2Cl_2$/MeOH with 2N $NH_3$=10/1) to yield the title compound. MS: 553.1

EXAMPLE 24

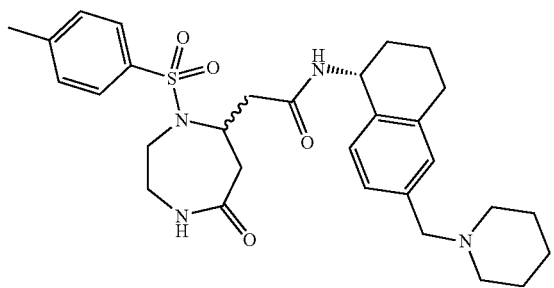

(R)-2-(7-Oxo-4-tosyl-1,4-diazepan-5-yl)-N-(6-(piperidin-1-ylmethyl)-1,2,3,4-tetrahydronaphthalen-1-yl)acetamide.

EXAMPLE 25

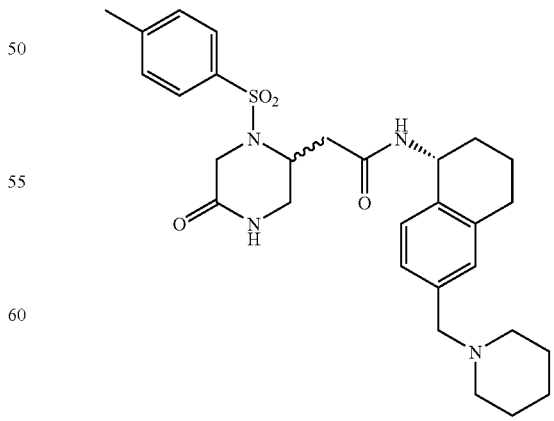

(R)-2-(5-oxo-1-tosylpiperazin-2-yl)-N-(6-(piperidin-1-ylmethyl)-1,2,3,4-tetrahydronaphthalen-1-yl)acetamide

105

A. Preparation of Ethyl 4-(2-(benzyloxycarbonyl)acetamido)-3-oxobutanoate.

2-(2-(benzyloxycarbonyl)acetamido)acetic acid (1.0 g, 3.75 mmol) and 1,1'-carbonyldiimidazole (730 mg, 4.5 mmol, 1.2 equiv) were stirred in THF (10 mL) at room temperature for 1 h and subsequently cooled to −78° C. In a separate oven-dried round-bottomed flask, ethyl acetate (1.9 mL, 19.5 mmol, 5.2 equiv) in THF (5 mL) was cooled to −78° C. and treated with a dropwise addition of Lithium bis(trimethylsilyl)amide (20 mL of a 1.0 M solution in THF, 5.3 equiv, 19.8 mmol). After 90 min, the acid imidazolide solution was transferred to this flask via cannula. The reaction was warmed to room temperature over 75 min, quenched with saturated ammonium chloride solution (10 μL) and extracted with ethyl acetate (2×20 mL). The combined organic layers were dried over MgSO₄, concentrated and purified on silica gel using 80% ethyl acetate in hexane as the eluant, affording ethyl 4-(2-(benzyloxycarbonyl)acetamido)-3-oxobutanoate. MS: 337.2 (M+H)⁺.

B. Preparation of Ethyl 2-(5-oxo-1-tosylpiperazin-2-yl)acetate.

A solution of ethyl 4-(2-(benzyloxycarbonyl)acetamido)-3-oxobutanoate (630 mg, 1.87 mmol) in dioxane (25 mL) was treated with Pd/C (10%, 100 mg) and stirred under an atmosphere of hydrogen at room temperature for 24 h. The catalyst was filtered through celite, the filtrate concentrated, dissolved in 1,2-dichloroethane (25 mL), treated with sodium cyanoborohydride (352 mg, 5.61 mmol, 3.0 equiv) and zinc (II) chloride (3.8 mL of a 0.5 M solution in THF, 1.87 mmol, 1.0 equiv). The reaction was heated to 50° C. for 2 h, cooled to room temperature and concentrated in vacuo. The crude reaction mixture was dissolved in 1:1 dioxane:water (40 mL) and p-toluenesulfonyl chloride (680 mg, 3.74 mmol, 2.0 equiv) and sodium carbonate (1.9 g, 18 mmol, 10.0 equiv) were added while stirring at room temperature. After 4 h, the reaction was diluted with ethyl acetate (50 mL) and washed with HCl solution (10%), water, brine, dried over MgSO₄, concentrated and purified on silica gel using 4% methanol in methylene chloride as eluant, affording ethyl 2-(5-oxo-1-tosylpiperazin-2-yl)acetate. MS: 341.2 (M+H)⁺.

C. Preparation of 2-(5-Oxo-1-tosylpiperazin-2-yl)acetic acid. Ethyl 2-(5-oxo-1-tosylpiperazin-2-yl)acetate (500 mg, 1.47 mmol) in 4:1 THF:water (10 mL) was mixed with LiOH·H₂O (75 mg, 1.76 mmol, 1.2 equiv) and stirred at room temperature for 1 h. The reaction was quenched with Dowex-50 acidic resin, filtered and concentrated to afford 2-(5-oxo-1-tosylpiperazin-2-yl)acetic acid. MS: 313.2 (M+H)⁺.

D. Preparation of (R)-2-(5-oxo-1-tosylpiperazin-2-yl)-N-(6-(piperidin-1-ylmethyl)-1,2,3,4-tetrahydronaphthalen-1-yl)acetamide.

Coupling of 2-(5-oxo-1-tosylpiperazin-2-yl)acetic acid with (R)-6-(piperidin-1-ylmethyl)-1,2,3,4-tetrahydronaphthalen-1-amine was conducted in the usual way with standard peptide coupling reagents as exemplified previously, to afford the title compound.

MS: 539.2 (M+H)⁺.

EXAMPLE 26

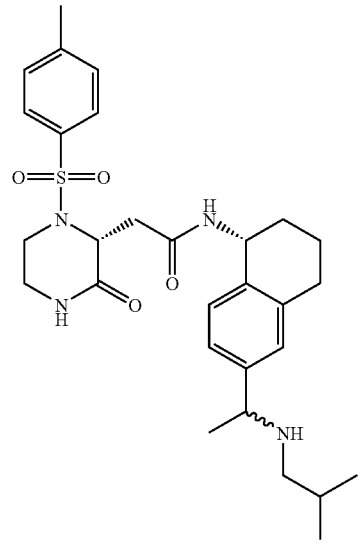

N-((R)-6-((R,S)-1-(isobutylamino)ethyl)-1,2,3,4-tetrahydronaphthalen-1-yl)-2-((R)-3-oxo-1-tosylpiperazin-2-yl)acetamide Step A—Preparation of (6-hydroxymethyl-1,2,3,4-tetrahydro-naphthalen-1-yl)-carbamic acid tert-butyl ester A mixture of (5-amino-5,6,7,8-tetrahydro-naphthalen-2-yl)-methanol (2.50 g, 14.1 mmol, 1.0 eq) and di-tert-butyl dicarbonate (Aldrich, 3.69 g, 16.9 mmol, 1.2 eq) and triethylamine (Aldrich, 2.85 g, 28.2 mmol, 2.0 eq) in CH₂Cl₂ (60 mL) was stirred at room temperature overnight. The reaction was quenched with H₂O (100 mL) and extracted with CH₂Cl₂ (100 mL×3). The extract phase was washed with saturated NaCl, dried over Na₂SO₄, filtered and concentrated. Flash column chromatography (silica gel, 0-35% EtOAc-Hexane) afforded the title compound as a white solid. MS (ESI, pos. ion) m/z: 278 (M+1).

Step B—Preparation of (6-formyl-1,2,3,4-tetrahydro-naphthalen-1-yl)-carbamic acid tert-butyl ester A mixture of (6-hydroxymethyl-1,2,3,4-tetrahydro-naphthalen-1-yl)-carbamic acid tert-butyl ester (3.16 g, 11.4 mmol, 1.0 eq) and MnO₂ (Aldrich, 12.9 g, 148.3 mmol, 13 eq) in CH₂Cl₂ (110 mL) was stirred at room temperature overnight. The reaction mixture was allowed to pass through a pad of Celite and the pad was washed with CH₂Cl₂ (100 mL×2). The concentration of the filtrate afforded the title compound as a white sticky semisolid. MS (ESI, pos. ion) m/z: 298 (M+Na).

Step C—Preparation of [6-(1-hydroxy-ethyl)-1,2,3,4-tetrahydro-naphthalen-1-yl]-carbamic acid tert-butyl ester To a sulution of (6-formyl-1,2,3,4-tetrahydro-naphthalen-1-yl)-carbamic acid tert-butyl ester (2.80 g, 10.2 mmol, 1.0 eq) in THF (100 mL) at −78° C. was added a solution of MeMgBr [Aldrich, 1.4 M in toluene/THF (3:1), 29 mL, 40.7 mmol, 4.0 eq] slowly. The reaction mixture was stirred at −78° C. for 20 min, warmed up to room temperature and stirred at room temperature for 2 h. The reaction was quenched with saturated NaHCO₃ (120 mL), and the crude product was extracted with EtOAc (100 mL×3). The extract phase was washed with saturated NaCl, dried over Na₂SO₄, filtered and concentrated. The title compound was obtained as a white solid. MS (ESI, pos. ion) m/z: 292 (M+1).

Step D—Preparation of (6-acetyl-1,2,3,4-tetrahydro-naphthalen-1-yl)-carbamic acid tert-butyl ester A mixture of [6-(1-hydroxy-ethyl)-1,2,3,4-tetrahydro-naphthalen-1-yl]-carbamic acid tert-butyl ester (2.63 g, 9.04 mmol, 1.0 eq) and MnO₂ (Aldrich, 10.2 g, 117.5 mmol, 13 eq) in CH₂Cl₂ (100 mL) was stirred at room temperature overnight. The reaction mixture was allowed to pass through a pad of Celite and the pad was washed with CH₂Cl₂ (100 mL×2). The concentration of the filtrate afforded the title compound as a white sticky semisolid. MS (ESI, pos. ion) m/z: 290 (M+1).

Step E—Preparation of N-((R)-6-acetyl-1,2,3,4-tetrahydronaphthalen-1-yl)-2-((R)-3-oxo-1-tosylpilperazin-2-yl) acetamide A mixture of (6-acetyl-1,2,3,4-tetrahydro-naphthalen-1-yl)-carbamic acid tert-butyl ester (463 mg, 1.6 mmol, 1.0 eq) in HCl/EtOAc (4.7 M, 20 mL) was stirred at room temperature for 5 h. The solvent was removed with a rotary evaporator, and the resulting 1-(5-amino-5,6,7,8-tetrahydro-naphthalen-2-yl)-ethanone hydrogen chloride was dried in vacuo.

A mixture of 1-(5-amino-5,6,7,8-tetrahydro-naphthalen-2-yl)-ethanone hydrogen chloride, (R)-2-(3-oxo-1-tosylpiperazin-2-yl)acetic acid (500 mg, 1.6 mmol, 1.0 eq), EDCI (Aldrich, 552 mg, 2.88 mmol, 1.8 eq), HOBt (Aldrich, 43 mg, 0.32 mmol, 0.2 eq) and diisobutylethylamine (Aldrich, 416 mg, 3.2 mmol, 2.0 eq) in CH₂Cl₂ (20 mL) was stirred at room temperature overnight. The reaction was quenched with 5% HCL (80 mL). The crude product was extracted with CH₂Cl₂ (80 mL×3). The extract phase was washed with saturated NaCl, dried over Na₂SO₄, filtered and concentrated. Flash column chromatography (silica gel, 0-5% MeOH-CH₂Cl₂) afforded the title compound as a white solid. MS (ESI, pos. ion) m/z: 484 (M+1).

Step F—Preparation of N-((R)-6-((R,S)-1-(isobutylamino) ethyl)-1,2,3,4-tetrahydronaphthalen-1-yl)-2-((R)-3-oxo-1-tosylpiperazin-2-yl)acetamide A mixture of N-((R)-6-acetyl-1,2,3,4-tetrahydronaphthalen-1-yl)-2-((R)-3-oxo-1-tosylpiperazin-2-yl)acetamide (120 mg, 0.248 mmol, 1.0 eq), isobutylamine (Aldrich,145 mg, 1.99 mmol, 8.0 eq), NaBH(OAc)₃ (Aldrich, 158 mg, 0.744 mmol, 3.0 eq) and glacial acetic acid (J, T. Baker, 30 mg, 0.496 mmol, 2.0 eq) in ClCH₂CH₂Cl (4 mL) was stirred at room temperature for 3 days. The reaction was quenched with saturated NaHCO₃ (60 mL). The crude product was extracted with CH₂Cl₂ (60 mL×3). The extract phase was washed with saturated NaCl, dried over Na₂SO₄, filtered and concentrated. Flash column chromatography (silica gel, 0-10% MeOH-CH₂Cl₂) afforded the title compound as a white solid. MS (ESI, pos. ion) m/z: 541 (M+1).

EXAMPLE 27

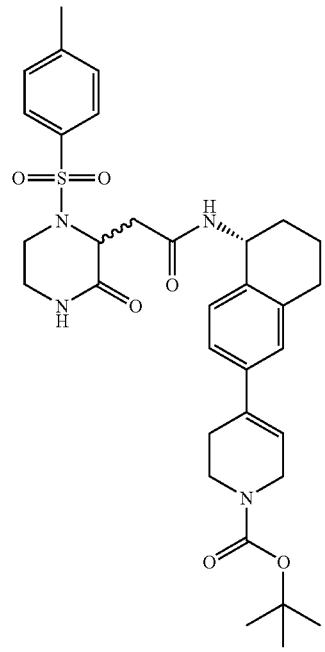

tert-butyl 4-((R)-5-(2-((R,S)-3-oxo-1-tosylpiperazin-2-yl)acetamido)-5,6,7,8-tetrahydronaphthalen-2-yl)-5,6-dihydropyridine-1(2H)-carboxylate Preparation of tert-butyl 4-((R)-5-(2-((R,S)-3-oxo-1-tosylpiperazin-2-yl)acetamido)-5,6,7,8-tetrahydronaphthalen-2-yl)-5,6-dihydropyridine-1(2H)-carboxylate A mixture of (R)-5-(2-(3-oxo-1-tosylpiperazin-2-yl)acetamido)-5,6,7,8-tetrahydronaphthalen-2-yl trifluoromethanesulfonate (330 mg, 0.562 mmol, 1.0 eq), tert-butyl 4-(4,4,5,5-tetramethyl-1,3,2-dioxaborolan-2-yl)-5,6-dihydropyridine-1(2H)-carboxylate (ChemShop, 261 mg, 0.843 mmol, 1.5 eq) and Pd(PPh₃)₄ (Aldrich, 65 mg, 0.0562 mmol, 0.1 eq) in toluene (3 mL), ethanol (0.7 mL) and aqueous NaHCO₃ (1.0 M, 0.7 mL) was stirred under N₂ at 80° C. for 20 h. The reaction mixture was allowed to cool down to room temperature and diluted with saturated NaHCO₃ (60 mL). The crude product was extracted with EtOAc (60 mL×3). The extract phase was washed with saturated NaCl, dried over Na₂SO₄, filtered and concentrated.

The reaction was repeated under the same condition as described above with 5-(2-((R,S)-3-oxo-1-tosylpiperazin-2-yl)acetamido)-5,6,7,8-tetrahydronaphthalen-2-yl trifluoromethanesulfonate (900 mg, 1.53 mmol, 1.0 eq), tert-butyl 4-(4,4,5,5-tetramethyl-1,3,2-dioxaborolan-2-yl)-5,6-dihydropyridine-1(2H)-carboxylate (ChemShop, 710 mg, 2.3 mmol, 1.5 eq) and Pd(PPh₃)₄ (Aldrich, 177 mg, 0.153 mmol, 0.1 eq).

Purification of the combined product from the above two experiments by flash column chromatography (silica gel, 0-7% MeOH-CH$_2$Cl$_2$) afforded the title compound as a tan solid. MS (ESI, pos. ion) m/z: 623 (M+1).

EXAMPLE 28

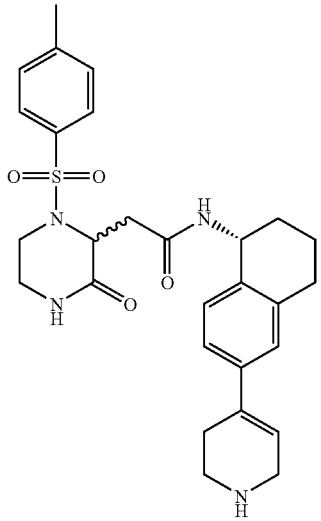

2-((R,S)-3-oxo-1-tosylpiperazin-2-yl)-N-((R)-6-(1,2, 3,6-tetrahydropyridin-4-yl)-1,2,3,4-tetrahydronaphthalen-1-yl)acetamide A mixture of tert-butyl 4-((R)-5-(2-((R,S)-3-oxo-1-tosylpiperazin-2-yl)acetamido)-5,6,7,8-tetrahydronaphthalen-2-yl)-5,6-dihydropyridine-1(2H)-carboxylate (1.10 g, 1.77 mmol, 1.0 eq) in HCl/EtOAc (4.7 M, 20 mL) was stirred at room temperature for 1 h. The reaction was quenched with saturated NaHCO$_3$ (100 mL). The product was extracted with CH$_2$Cl$_2$ (100 mL×4). The extract phase was washed with saturated NaCl, dried over Na$_2$SO$_4$ and filtered. Concentration with a rotary evaporator afforded the title compound as a yellow solid. MS (ESI, pos. ion) m/z: 523 (M+1).

EXAMPLE 29

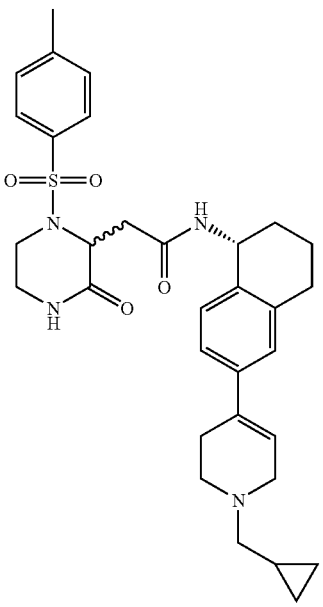

N-((R)-6-(1-(cyclopropylmethyl)-1,2,3,6-tetrahydropyridin-4-yl)-1,2,3,4-tetrahydronaphthalen-1-yl)-2-((R,S)-3-oxo-1-tosylpiperazin-2-yl)acetamide A mixture of 2-((R,S)-3-oxo-1-tosylpiperazin-2-yl)-N-((R)-6-(1,2,3,6-tetrahydropyridin-4-yl)-1,2,3,4-tetrahydronaphthalen-1-yl)acetamide (97 mg, 0.19 mmol, 1.0 eq), cyclopropanecarbaldehyde (Aldrich, 20.3 mg, 0.29 mmo, 1.5 eq) and NaBH(OAc)$_3$ in ClCH$_2$CH$_2$Cl (2 mL) was stirred under N$_2$ at room temperature overnight. The reaction was quenched with saturated NaHCO$_3$ (30 mL). The crude product was extracted with CH$_2$Cl$_2$ (40 mL×3). The extract phase was washed with saturated NaCl, dried over Na$_2$SO$_4$, filtered and concentrated. Flash column chromatography (silica gel, 0-10% MeOH-CH$_2$Cl$_2$) afforded the title compound as a white solid. MS (ESI, pos. ion) m/z: 577 (M+1).

EXAMPLE 30

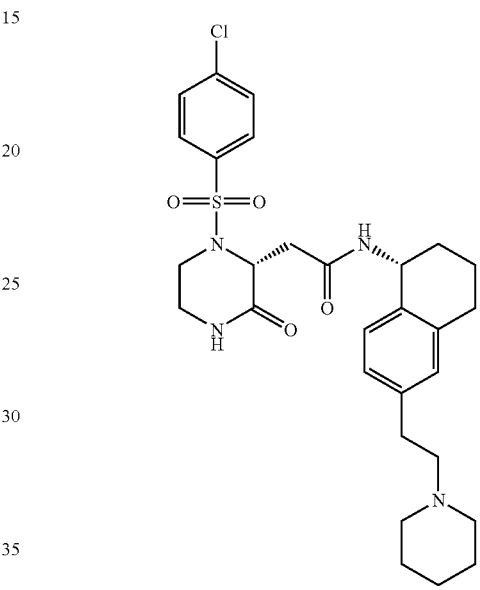

2-((R)-1-(4-chlorophenylsulfonyl)-3-oxopiperazin-2-yl)-N-((R)-6-(2-(piperidin-1-yl)ethyl)-1,2,3,4-tetrahydronaphthalen-1-yl)acetamide A. Preparation of S)-tert-butyl 6-(iodomethyl)-1,2,3,4-tetrahydronaphthalen-1-ylcarbamate To a solution of (R)-tert-butyl 6-(hydroxymethyl)-1,2,3,4-tetrahydronaphthalen-1-ylcarbamate (415.5 mg, 1.5 mmol) in dichloromethane/ether (1:1, 30 mL) at room temperaturewere added triphenylphosphine (590 mg, 2.25 mmol) and imidazole (153 mg, 2.25 mmol). To this stirred solution was then added iodine (571 mg, 2.25 mmol). After stirring for 20 min, the reaction was quenched with 10% Na$_2$S$_2$O$_3$ (15 mL) until it became a clear two-phase solution. The aqueous phase was extracted with ether. The combined organic phase was dried over Na$_2$SO$_4$, filtered, and evaporated to dryness. Flash chromatography (SiO$_2$, hexane/CH$_2$Cl$_2$=3:1 to pure CH$_2$Cl$_2$) afforded the title compound as a white solid.

B. Preparation of (R)-tert-butyl 6-(2-(1,3-dithian-2-yl)ethyl)-1,2,3,4-tetrahydronaphthalen-1-ylcarbamate.

To a solution of 1,3-dithiane (1.01 g, 8.4 mmol) in 10 mL of dry THF at −30° C. was added dropwise 2.5M n-butyllithium in hexane (3.36 mL, 8.4 mmol). After stirring at −20° C. for 1.5 h, a solution of the iodide from the previous (542 mg, 1.4 mmole, azeotroped with benzene) in 10 mL of dry THF was added dropwise at −20° C. The reaction was stirred at −5° C. to 0° C. for 1 h. It was then quenched with sat. NH$_4$Cl solution, extracted with EtOAc, dried over Na$_2$SO$_4$, filtered, and evaporated to dryness. Flash chromatography (SiO$_2$, CH$_2$Cl$_2$/hexane=1:1 to 2:1 to CH$_2$Cl$_2$/EtOAc=100:3) afforded the title compound as a white solid.

C. Preparation of (R)-6-(2-(1,3-dithian-2-yl)ethyl)-1,2,3,4-tetrahydronaphthalen-1-amine To a solution of the above dithiane (146 mg, 0.385 mmol) in 5 mL of methanol at room temperature was added 4 N HCl in dioxane (0.48 mL, 1.93 mmol). After stirring at room temperature for 2 h, the reaction solution was evaporated to dryness. The residue was treated with 0.5 mL of triethylamine and it was evaporated again in vacuo. The crude product was azeotroped with benzene and directly used in the next step.

D. Preparation of N-((R)-6-((1,3-dithian-2-yl)methyl)-1,2,3,4-tetrahydronaphthalen-1-yl)-2-((R)-1-(4-chlorophenylsulfonyl)-3-oxopiperazin-2-yl)acetamide A solution of (R)-2-(1-(4-chlorophenylsulfonyl)-3-oxopiperazin-2-yl)acetic acid (1.98 g, 6.0 mmol), crude (R)-6-(2-(1,3-dithian-2-yl)ethyl)-1,2,3,4-tetrahydronaphthalen-1-amine (1.8 g, 6.45 mmol), HOBt (892 mg, 6.6 mmol) and EDCI(1.265 g, 6.6 mmol)in 15 mL of DMF was stirred overnight at room temperature. After quenching with Sat. NaHCO₃ solution, the reaction mixture was extracted with EtOAc/hexane (1:1, 200 mL×2). The combined organic phase was washed brine, dried over Na₂SO₄, and evaporated in vaco. Flash chromatography (SiO₂, hexane/EtOAc=2:1 to 3:2 to 1:1) gave the title compound as a white solid. MS: 609.7 (M+1).

E. Preparation of 2-((R)-1-(4-chlorophenylsulfonyl)-3-oxopiperazin-2-yl)-N-((R)-6-(2-oxoethyl)-1,2,3,4-tetrahydronaphthalen-1-yl)acetamide Dithiane from the above step (3.5 g, 5.56 mmol) and CaCO₃ (1.61 g, 16.08 mmol) were suspended in 60 mL of THF/water (5:1). Then a solution of Hg(ClO₄)₂ (4.28 g, 10.72 mmol) in 10 mL of water was added dropwise. After stirring at room temperature for 1 h, the reaction mixture was filtered through a silica gel pad with the help of EtOAc. The filtrate was evaporated to dryness. Flash chromatography (SiO₂, hexane/EtOAc=3:2 to 1:2) gave the title compound as a white solid, together with 230 mg of recovered starting material.

F. Preparation of 2-((R)-1-(4-chlorophenylsulfonyl)-3-oxopiperazin-2-yl)-N-((R)-6-(2-(piperidin-1-yl)ethyl)-1,2,3,4-tetrahydronaphthalen-1-yl)acetamide To a solution of the product from step E (63 mg, 0.116 mmol) and piperidine (20 mg, 0.23 mmol) in 1 mL of dichloroethane was added sodium triacetoxyborohydride (49 mg, 0.23 mmol). After stirring overnight at room temperature, the reaction solution was diluted with EtOAc and washed with sat. NaHCO₃ and brine. The organic phase was dried over Na₂SO₄ and evaporated to dryness in vaco. Flash chromatography (SiO₂, EtOAc to EtOAc/MeOH=100:10 to 100:12) afforded the title compound as a white solid. MS: 573.2 (M+1).

EXAMPLE 31

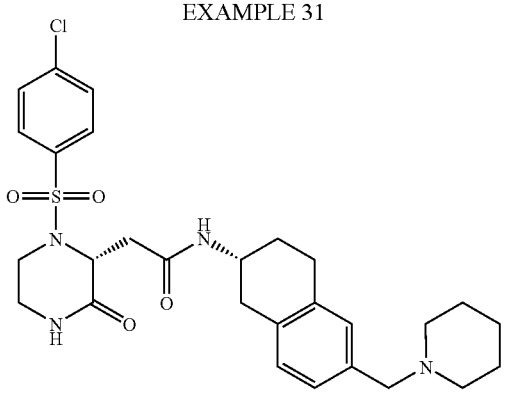

R)-2-(l-(4-chlorophenylsulfonyl)-3-oxopiperazin-2-yl)-N-(6-(Piiperidin-1-ylmethyl)-1,2,3,4-tetrahydronaphthalen-2-yl)acetamide A. Preparation of (R)-tert-butyl 6-bromo-1,2,3,4-tetrahydronaphthalen-2-ylcarbamate.

To a solution of (t-Boc)₂O (3.28 g, 15 mmol) and (R)-6-bromo-1,2,3,4-tetrahydronaphthalen-2-amine (3.94 g, 15 mmol) in DMF (10 mL)was added dropwise triethylamine (3.0 g, 30 mmol) at 0 C. After stirring 3 h at room temperature, the reaction solution was diluted with EtOAc/Hexane (2:1), washed with water, dried over Na₂SO₄ and evaporated to afford the title compound as a white solid.

B. Preparation of (R)-tert-butyl 6-vinyl-1,2,3,4-tetrahydronaphthalen-2-ylcarbamate.

A mixture of the above product (1.63 g, 5 mmol), vinyltributyltin (2.2 g, 7 mmol), tri-t-butylphosphine (101 mg, 0.5 mmol), triethylamine (1.0 g, 10 mmol) and Pd₂(dba)₃ (229 mg, 0.25 mmol) in toluene (2 mL) was heated at 80° C. in microwave for 20 min. After cooling down to room temperature, the reaction solution was quenched with sat. NH₄Cl, extracted with EtOAc, dried, and evaporated to dryness. Flash chromatography (SiO₂, hexane to hexane/DCM=2:1 to 1:1 to pure DCM) afforded the title compound as a white solid.

C. Preparation of (R)-tert-butyl 6-vinyl-1,2,3,4-tetrahydronaphthalen-2-ylcarbamate.

TFA (0.7 mL, 9.07 mmol) was added dropwise to a solution of the product from step A (620 mg, 2.27 mmol) in DCM (10 mL). After stirring at room temperature for 4 h, the reaction mixture was evaporated to dryness. NEt₃ (1 mL) was added to the residue and evaporated again to give the crude product, which was directly used in the next step.

D. Preparation of (R)-2-(1-(4-chlorophenylsulfonyl)-3-oxopiperazin-2-yl)-N-(6-vinyl-1,2,3,4-tetrahydronaphthalen-2-yl)acetamide A solution of 2-(1-(4-chlorophenylsulfonyl)-3-oxopiperazin-2-yl)acetic acid (332 mg, 1 mmol), crude 48999-36 (190 mg, 1.1 mmol), II (135 mg, 1 mmol) and III (191 mg, 1 mmol) in 1 mL of DMF was stirred overnight at room temperature. After quenching with sat. NaHCO₃ solution, the reaction mixture was extracted with EtOAc. The combined organic phase was washed brine, dried over Na₂SO₄, and evaporated in vaco. Flash chromatography (SiO₂, EtOAc to EtOAc/MeOH=100:3 to 100:5 to 100:6) gave the title compound as a white solid.

E. Preparation of (R)-2-(1-(4-chlorophenylsulfonyl)-3-oxopiperazin-2-yl)-N-(6-formyl-1,2,3,4-tetrahydronaphthalen-2-yl)acetamide.

To a solution of the procuct of step D. (280 mg, 0.575 mmol) in 13 mL of a mixture solvent t-butanol/THF/water (10:2:1) was added NMO (135 mg, 1.15 mmol), followed by OsO₄ (2.5% w/w in t-butanol, 175 mg, 0.017 mmol). After stirring overnight at room temperature, 4 mL of pH 7.2 phosphate buffer was added, followed by NaIO₄ (615 mg, 2.875 mmol). After stirring for 5 h at room temperature, the reaction solution was diluted with EtOAc and washed with brine. The organic phase was dried over Na₂SO₄ and evaporated to dryness in vaco. Flash chromatography (SiO₂, EtOAc/hexane=1:1) afforded the title compound as a white solid.

Preparation of (R)-2-(1-(4-chlorophenylsulfonyl)-3-oxopiperazin-2-yl)-N-(6-(piperidin-1-ylmethyl)-1,2,3,4-tetrahydronaphthalen-2-yl)acetamide.

To a solution of the product of the previous step (60 mg, 0.123 mmol) and piperidine (20 mg, 0.23 mmol) in 1 mL of dichloroethane was added sodium triacetoxyborohydride (49 mg, 0.23 mmol). After stirring overnight at room temperature, the reaction solution was diluted with EtOAc and washed with sat. $NaHCO_3$ and brine. The organic phase was dried over $Na_2O_4$ and evaporated to dryness in vaco. Flash chromatography ($SiO_3$, EtOAc to EtOAc/MeOH=100:15 to 100:20 to EtOAc/2.0 M $NH_3$ in MeOH=100:15 to 100:20) afforded the title compound as a white solid. MS: 559.2 (M+1).

EXAMPLE 32

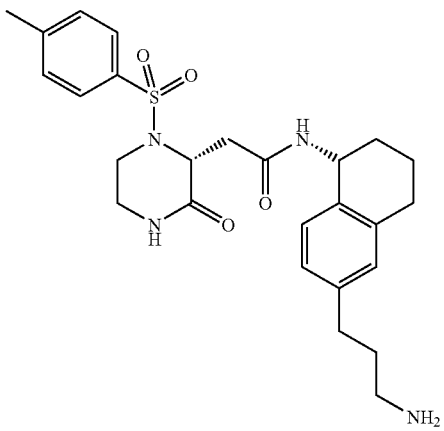

N-((R)-6-(3-aminopropyl)-1,2,3,4-tetrahydronaphthalen-1-yl)-2-((R)-3-oxo-1-tosylpiperazin-2-yl)acetamide A. Preparation of (R,E)-tert-butyl 6-(2-cyanovinyl)-1,2,3,4-tetrahydronaphthalen-1-ylcarbamate To a 300 mL flame dry 3-neck round bottom flask was added diethyl cyanophosphonate (14.86 g, 83.89 mmol) and THF (100 mL). After cooled to 0° C., sodium bis(trimethyl-silyl) amide (72.0 mL, 71.90 mmol) was added dropwise via the addition funnel. After stirred for 30 min at 0° C., It was cooled to −78° C. followed by adding (R)-tert-butyl-6-formyl-1,2,3,4-tetrahydronaphthalen-1-ylcarbamate (6.6 g, 23.97 mmol) in TBF (60 mL) dropwise via the addition funnel. It was stirred for 18 h. Acetone cyanohydrin (3.1 mL, 33.48 mmol) was then added dropwise via the addition funnel. The resulting mixture was warmed up to rt and continued to stir for 18 h. The reaction mixture was quenched with sat. $NH_4Cl$. Solvent was evaporated in vacuo. The residue was extracted with EtOAc. The organic layer was washed with $H_2O$, brine, dried over $MgSO_4$ and removed solvent. The crude product was purified by chromatography on silica gel. Elution with Hex:EtOAc mixture (70:30) gave final compound. MS m/z: 299.12 (M+H). Calc'd. for $C_{18}H_{22}N_2O_2$-298.23.

B. (R,E)-3-(5-amino-5,6,7,8-tetrahydronaphthalen-2-yl)acralonitrile

The product from the previous step was deprotected using HCl in dioxane to give the title compound in quantitative yield. MS m/z: 199.12 (M+H). Calc'd. for $C_{13}H_{14}N_2$-198.23.

C. N-((R)-6-((E)-2-cyanovinyl)-1,2,3,4-tetrahydronaphthalen-1-yl)-2-((R)-3-oxo-1-tosylpiperazin-2-yl)acetamide To a 250 mL round bottom flask was added (R)-2-(3-oxo-1-tosylpiperazin-2-yl)acetic acid (2.0 g, 6.40 mmol), followed by (R,E)-3-(5-amino-5,6,7,8-tetrahydronaphthalen-2-yl)acrylonitrile (1.26 g, 6.40 mmol), dry $CH_2Cl_2$ (70 mL), HATU (1.2 mg, 3.20 mmol), EDCI (1.4 g, 7.04 mmol) and hunig base (2.2 mL, 12.80 mmol). The resulting mixture was stirred at rt for 20 h. Removed solvent to dryness. The residue was purified by chromatography on silica gel. Elution with $CH_2Cl_2$:MeOH mixture (95:5) gave final compound (2.1 g, 66%). MS m/z: 493.3 (M+H). Calc'd. for $C_{26}H_{28}N_4O_4S$ -492.6.

D. N-((R)-6-(3-aminopropyl)-1,2,3,4-tetrahydronaphthalen-1-yl)-2-((R)-3-oxo-1-tosylpiperazin-2-yl)acetamide To a solution of N-((R)-6-((E)-2-cyanovinyl)-1,2,3,4-tetrahydronaphthalen-1-yl)-2-((R)-3-oxo-1-tosylpiperazin-2-yl)acetamide (1.6 g, 3.25 mmol) in EtOH:$CHCl_3$=20:1 solvent mixture (40 mL) was added $PtO_2$ (221.0 mg, 0.97 mmol). It was flushed with $N_2$ followed by evacuating—this was done 3 times to ensure free of air and $N_2$. After last evacuation, $H_2$ balloon was inserted. It was stirred at rt under $H_2$ for 20 h. The solvent was separated from the catalyst by passing through celite. Solvent was then removed to give the final product. MS m/z: 499.1 (M+H). Calc'd. for $C_{26}H_{34}N_4O_4S$ -498.6.

EXAMPLE 33

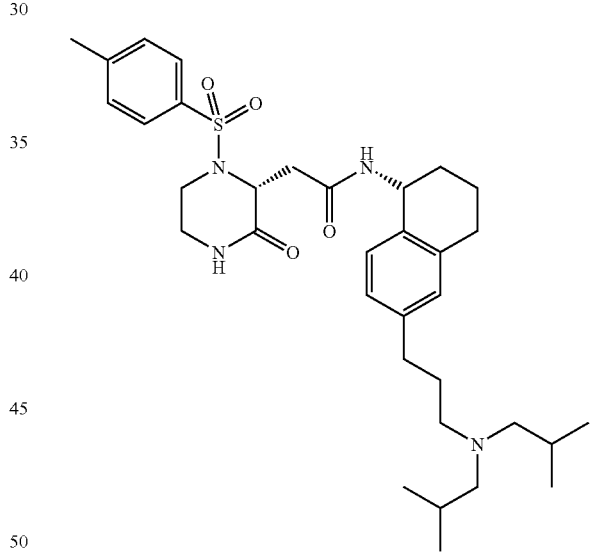

N-((R)-6-(3-(diisobutylamino)propyl)-1,2,3,4-tetrahydronaphthalen-1-yl)-2-((R)-3-oxo-1-tosylpiperazin-2-yl)acetamide To a solution of N-((R)-6-(3-aminopropyl)-1,2,3,4-tetrahydronaphthalen-1-yl)-2-((R)-3-oxo-1-tosylpiperazin-2-yl)acetamide (650.0 mg, 1.3 mmol) in dry DCM (15 mL) was added isobutyraldehyde (240.0 μL, 2.61 mmol) and HOAc (2 drops). The resulting mixture was stirred at rt under $N_2$. After 1 h, MS showed the formation of imine; NaBH(OAc)$_3$ (830.0 mg, 3.91 mmol) was then added. The resulting mixture was stirred for 10 min. The reaction mixture was quenched with sat. $NaHCO_3$. The organic layer was dried over $MgSO_4$ and evaporated in vacuo. The crude solid was purified by chromatography on silica gel. Elution with DCM:MeOH(2M NH$_3$) mixture (95:5) gave final compound. MS m/z: 611.21 (M+H). Calc'd. for $C_{34}H_{50}N_4O_4S$ -610.87.

Examples numbers marked with "*" indicate the stereochemical bond in the alpha position on the piperazinone ring is predominantly in the R configuration.

The following compounds were made using the methods described in Examples 1-17.

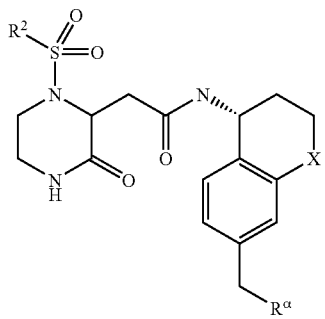

| No. | R$^2$ | R$^\alpha$ | X | MW | MS data |
|---|---|---|---|---|---|
| 34 | 5-chlorobenzo[b]thiophen-2-yl | 1-piperidinyl | CH$_2$ | 615.215 | 614.7, 616.7 |
| 35 | 4-pentafluoroethylphenyl | tert-butylamino | CH$_2$ | 630.675 | 631.1 |
| 36 | 3-methyl-5-chlorobenzo[b]-thiophen-2-yl | tert-butylamino | O | 619.203 | 619 |
| 37 | 3-methyl-5-chlorobenzo[b]-thiophen-2-yl | cyclopentylamino | CH$_2$ | 629.24 | 629 |
| 38 | 3-trifluoromethyl-4-methylphenyl | tert-butylamino | CH$_2$ | 594.695 | 595.2 |
| 39 | 3-trifluoromethyl-4-methylphenyl | 1-piperidinyl | CH$_2$ | 606.705 | 607.2 |
| 40 | 3-trifluoromethyl-4-methylphenyl | isobutylamino | CH$_2$ | 594.695 | 595.2 |
| 41 | 3-trifluoromethyl-4-methylphenyl | 2,2-dimethyl-propylamino | CH$_2$ | 608.72 | 609.2 |
| 42 | 3,5-dibromo-4-methylphenyl | tert-butylamino | CH$_2$ | 684.49 | 685.1 |
| 43 | 3,5-diD-4-methylphenyl | tert-butylamino | CH$_2$ | 528.71 | 529.2 |
| 44 | 3-trifluoromethyl-4-methylphenyl | hydroxy | CH$_2$ | 539.57 | 540.2 |
| 45 | 3-trifluoromethyl-4-chlorophenyl | tert-butylamino | CH$_2$ | 615.115 | 615.2 |
| 46 | 4-methylphenyl | 2,2-dimethyl-propylamino | CH$_2$ | 540.725 | 541.4 |
| 47 | 3-trifluoromethylphenyl | piperidin-1-yl | CH$_2$ | 578.695 | 579 |
| 48 | 2,5-dimethyl-4-chlorophenyl | 4-methylpiperazin-1-yl | O | 604.17 | 605.3 |
| 49 | 2,5-dimethyl-4-chlorophenyl | tetrahydropyran-4-ylamino | O | 605.15 | 606.2 |
| 50 | 2,5-dimethyl-4-chlorophenyl | (cyclopropylmethyl)-amino | O | 575.125 | 576.3 |
| 51 | 2,5-dimethyl-4-chlorophenyl | cyclopentylamino | O | 589.155 | 590.4 |
| 52 | 2,5-dimethyl-4-chlorophenyl | cyclopentylamino | CH$_2$ | 587.18 | 588.3 |
| 53 | 2,5-dimethyl-4-chlorophenyl | 4-methylpiperazin-1-yl | CH$_2$ | 602.195 | 603.4 |
| 54 | 2,5-dimethyl-4-chlorophenyl | tetrahydropyran-4-ylamino | CH$_2$ | 603.18 | 604.3 |
| 55 | 2,5-dimethyl-4-chlorophenyl | (cyclopropylmethyl)-amino | CH$_2$ | 573.155 | 574.2 |
| 56 | 4-trifluoromethoxyphenyl | tert-butylamino | CH$_2$ | 596.665 | 597.2 |
| 57 | 4-trifluoromethoxyphenyl | tert-butylamino | O | 598.64 | 599 |
| 58 | 4-trifluoromethoxyphenyl | isobutylamino | CH$_2$ | 596.665 | 597.2 |
| 59 | 4-trifluoromethoxyphenyl | (cyclopropylmethyl)-amino | CH$_2$ | 594.65 | 595.2 |
| 60 | 4-trifluoromethoxyphenyl | isopropylamino | CH$_2$ | 582.64 | 583.2 |
| 61 | 4-trifluoromethoxyphenyl | cyclobutylamino | CH$_2$ | 594.65 | 595.2 |
| 62 | 4-trifluoromethylphenyl | tert-butylamino | CH$_2$ | 580.67 | 581.2 |
| 63 | 4-trifluoromethylphenyl | piperidin-1-yl | CH$_2$ | 592.68 | 593.3 |
| 64 | 4-trifluoromethylphenyl | isobutylamino | CH$_2$ | 580.67 | 581.2 |
| 65 | 4-trifluoromethylphenyl | cyclopentylamino | CH$_2$ | 592.68 | 593.3 |
| 66 | 4-methylphenyl | tert-butylamino | O | 563.115 | 563.4, 564.4 |
| 67 | 4-methylphenyl | 4-methylpiperazin-1-yl | CH$_2$ | 553.724 | 554.1 |
| 68 | 4-methylphenyl | cyclopentylamino | O | 540.681 | 541.2 |

-continued

| No. | R² | Rᵃ | X | MW | MS data |
|---|---|---|---|---|---|
| 69 | 3,4-dichlorophenyl | tert-butylamino | CH₂ | 609.615 | 609 |
| 70 | 3,4-dichlorophenyl | tert-butylamino | CH₂ | 581.56 | 581 |
| 71 | 3,4-dichlorophenyl | piperidin-1-yl | CH₂ | 593.575 | 593 |
| 72 | 3,4-dichlorophenyl | 4-fluoropiperidin-1-yl | CH₂ | 611.565 | 611 |
| 73 | 3,4-dichlorophenyl | pyrrolidin-1-yl | CH₂ | 579.545 | 579 |
| 74 | 3,4-dichlorophenyl | isobutylamino | CH₂ | 581.56 | 581 |
| 75 | 2,5-dichlorophenyl | piperidin-1-yl | CH₂ | 593.575 | 593 |
| 76 | 2,5-dimethyl-4-chlorophenyl | piperidin-1-yl | CH₂ | 587.18 | 587 |
| 77 | 3-methylphenyl | piperidin-1-yl | CH₂ | 538.71 | 539 |
| 78 | 2-methylphenyl | piperidin-1-yl | CH₂ | 538.71 | 539 |
| 79 | 3-chloro-4-fluorophenyl | piperidin-1-yl | CH₂ | 577.12 | 577 |
| 80 | 4-tert-butylphenyl | piperidin-1-yl | CH₂ | 580.79 | 581 |
| 81 | 2,4-dichlorophenyl | piperidin-1-yl | CH₂ | 593.58 | 593 |
| 82 | 2-chlorophenyl | piperidin-1-yl | CH₂ | 559.13 | 559 |
| 83 | phenyl | piperidin-1-yl | CH₂ | 524.68 | 525 |
| 84 | 3-trifluorophenyl | piperidin-1-yl | CH₂ | 592.68 | 593 |
| 85 | 3-bromo-5-chlorothiophen-2-yl | piperidin-1-yl | CH₂ | 644.05 | 645 |
| 86 | 4-methylphenyl | piperidin-1-yl | CH₂ | 538.71 | 539.7 |
| 87 | 4-methylphenyl | 2-(pyrrolidin-1-yl)ethylamino | CH₂ | 567.751 | 568.5 |
| 88 | 4-methylphenyl | 4-fluoropiperidin-1-yl | CH₂ | 556.699 | 557.2 |
| 89 | 4-methylphenyl | morpholin-4-yl | CH₂ | 540.681 | 541.4 |
| 90 | 4-methylphenyl | isopentylamino | CH₂ | 540.725 | 541.4 |
| 91 | 4-methylphenyl | isopentylamino | CH₂ | 554.752 | 555.4 |
| 92 | 4-methylphenyl | cyclohexylmethylamino | CH₂ | 566.765 | 567.4 |
| 93 | 4-methylphenyl | 2-(2-fluorophenyl)-ethylamine | CH₂ | 592.73 | 593.2 |
| 94 | 4-methylphenyl | benzylamino | CH₂ | 560.715 | 561.4 |
| 95 | 4-methylphenyl | piperidin-1-ylmethyl | CH₂ | 552.735 | 553.2 |
| 96 | 4-chlorophenyl | piperidin-1-yl | CH₂ | 559.13 | 559.2 |
| 97 | 4-chlorophenyl | morpholin-4-yl | CH₂ | 561.1 | 561.2 |
| 98 | 4-chlorophenyl | 4-methylpiperazin-1-yl | CH₂ | 574.14 | 574.2 |
| 99 | 4-chlorophenyl | 2,2-dimethyl-propylamino | CH₂ | 561.145 | 561.2 |
| 100 | 4-chlorophenyl | isobutylamino | CH₂ | 547.115 | 547.2 |
| 101 | 4-chlorophenyl | benzylamino | CH₂ | 581.135 | 581.2 |
| 102 | 4-chlorophenyl | 2-phenylethylamino | CH₂ | 595.16 | 595.2 |
| 103 | 4-chlorophenyl | 2-(2-fluorophenyl)-ethylamino | CH₂ | 613.15 | 613.2 |
| 104 | 4-chlorophenyl | cyclobutylamino | CH₂ | 545.1 | 545.2 |
| 105 | 4-chlorophenyl | 2-(pyrrolidin-1-yl)ethylamino | CH₂ | 588.17 | 588.2 |
| 106 | 4-chlorophenyl | isopentylamino | CH₂ | 561.145 | 561.2 |
| 107 | 4-chlorophenyl | 4-fluoropiperidin-1-yl | CH₂ | 577.12 | 577.2 |
| 108 | 4-chlorophenyl | (naphth-1-yl-methyl)amino | CH₂ | 631.195 | 631.2 |
| 109 | 4-chlorophenyl | 2-(2-methoxyphenyl)-ethylamino | CH₂ | 625.185 | 625.2 |
| 110 | 4-chlorophenyl | H | CH₂ | 491.01 | 491.2 |
| 111 | 4-methylphenyl | 2-methoxyethylamino | CH₂ | 528.67 | 529.2 |
| 112 | 4-methylphenyl | 2-hydroxymethylamino | CH₂ | 514.644 | 515.2 |
| 113 | 3-methyl-5-chlorothiophen-2-yl | tert-butylamino | CH₂ | 617.23 | 617 |

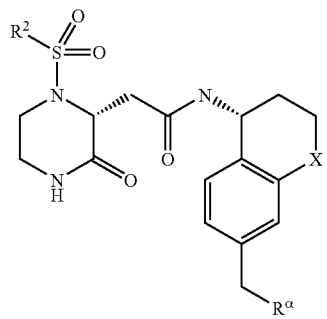

| No. | R² | Rᵃ | X | MW | MS data |
|---|---|---|---|---|---|
| 114 | 3,5-dibromo-4-methylphenyl | 2,2-dimethyl-propylamino | CH₂ | 698.517 | 699 |
| 115 | 4-methylphenyl | 4-fluoropiperidin-1-yl | CH₂ | 556.699 | 557.2 |
| 116 | 4-methylphenyl | piperidin-1-yl | O | 540.681 | 541 |
| 117 | 4-methylphenyl | piperidin-1-yl | CH₂ | 538.709 | 539.2 |
| 118 | 3,4-dichlorophenyl | tert-butylamino | O | 617.979 | 617.2, 619.2 |
| 119 | 4-methylphenyl | tert-butylamino | O | 528.67 | 529 |
| 120 | 5-chlorothiophen-2-yl | 4-methylpiperazin-1-yl | O | 582.143 | 583 |

-continued

| No. | R² | Rᵅ | X | MW | MS data |
|---|---|---|---|---|---|
| 121 | 4-methylphenyl | 4-methylpiperazin-1-yl | O | 555.696 | 556 |
| 122 | 4-chlorophenyl | piperidin-1-yl | CH₂ | 559.128 | 559.2 |
| 123 | 4-chlorophenyl | tert-butylamino | CH₂ | 547.117 | 547.2 |
| 124 | 4-chlorophenyl | 2,2-dimethyl-propylamino | CH₂ | 561.143 | 561.2 |
| 125 | 4-chlorophenyl | 2,2-dimethyl-propylamino | O | 563.115 | 563.2 |
| 126 | 4-chlorophenyl | isobutylamino | CH₂ | 547.117 | 547.2 |
| 127 | 4-chlorophenyl | cyclobutylamino | CH₂ | 545.101 | 545.2 |
| 128 | 4-methylphenyl | tert-butylamino | CH₂ | 526.698 | 527.4 |
| 129 | 4-methylphenyl | 2,2-dimethyl-propylamino | CH₂ | 540.725 | 541.4 |
| 130 | 4-methylphenyl | isobutylamino | CH₂ | 526.698 | 527.2 |
| 131 | 4-methylphenyl | isopentylamino | CH₂ | 540.725 | 541.2 |
| 132 | 4-methylphenyl | (S)-sec-butylamino | CH₂ | 526.698 | 527.2 |
| 133 | 4-methylphenyl | 2-(pyrrolidin-1-yl)ethylamino | CH₂ | 567.751 | 568.2 |
| 134 | 4-methylphenyl | cyclohexylmethylamino | CH₂ | 566.763 | 567.2 |
| 135 | 4-methylphenyl | cyclohexylamino | CH₂ | 552.736 | 553.2 |
| 136 | 4-methylphenyl | (cyclopropyl-methyl)amino | CH₂ | 524.682 | 525.2 |
| 137 | 4-methylphenyl | morpholin-4-yl | CH₂ | 540.681 | 541.2 |
| 138 | 4-methylphenyl | cyclopentylamino | CH₂ | 538.709 | 539.2 |
| 139 | 4-methylphenyl | cyclopropylamino | CH₂ | 510.656 | 511.2 |
| 140 | 4-methylphenyl | azepan-1-yl | CH₂ | 552.736 | 553.2 |
| 141 | 4-methylphenyl | 3-hydroxypiperidin-1-yl | CH₂ | 554.71 | 555.2 |

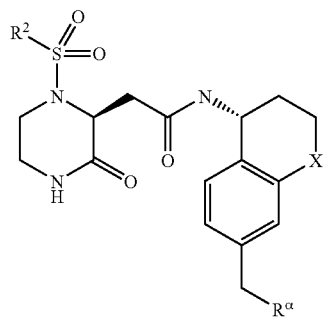

| No. | R² | Rᵅ | X | MW | MS data |
|---|---|---|---|---|---|
| 142 | 4-methylphenyl | tert-butylamino | CH₂ | 526.698 | 527.4 |
| 143 | 3,5-dibromo-4-methylphenyl | tert-butylamino | CH₂ | 684.49 | 685 |

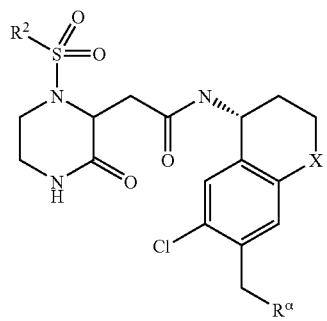

| No. | R² | Rᵅ | X | MW | MS data |
|---|---|---|---|---|---|
| 144 | 2,4,6-trimethylphenyl | tert-butylamino | O | 591.17 | 591.3, 593.3 |
| 145 | 3,4-dichlorophenyl | tert-butylamino | O | 617.98 | 617.2 |
| 146 | naphth-2-yl | tert-butylamino | O | 599.15 | 599.2, 601.2 |

-continued

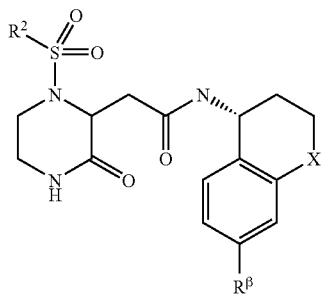

| No. | R² | Rᵝ | X | MW | MS data |
|---|---|---|---|---|---|
| 147 | 3,4-dichlorophenyl | H | $CH_2$ | 496.413 | 496 |
| 148 | 4-methylphenyl | H | $SO_2$ | 491.587 | 492.4 |

The following compounds were made using the methods described in Example 26.

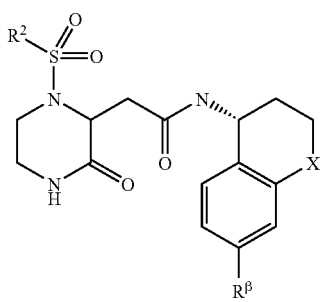

| No. | R² | Rᵝ | X | MW | MS data |
|---|---|---|---|---|---|
| 149 | 4-methylphenyl | (R)-CH(CH₃)-N(H)isobutyl | $CH_2$ | 540.725 | 541 |

-continued

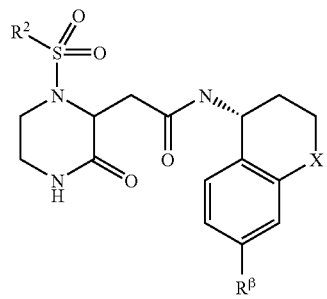

| No. | R² | Rᵝ | X | MW | MS data |
|---|---|---|---|---|---|
| 150 | 4-methylphenyl | (R)-CH(CH₃)-N(H)cyclopentyl | $CH_2$ | 552.735 | |

The following compounds were made using the methods described in Examples 22, 23 and 27.

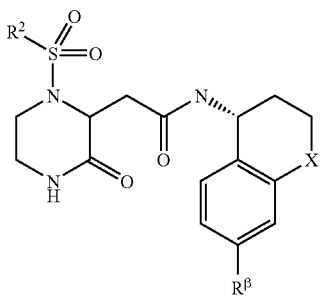

| No. | R² | Rᵝ | X | MW | MS data |
|---|---|---|---|---|---|
| 151 | 4-methylphenyl | (structure shown) | $CH_2$ | 622.783 | 623 |

-continued

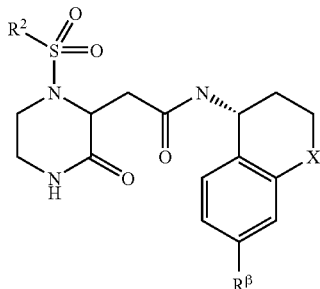

| No. | R² | Rᵝ | X | MW | MS data |
|---|---|---|---|---|---|
| 152 | 4-methylphenyl | 3,6-dihydro-2H-pyridin-4-yl | $CH_2$ | 522.667 | 523 |
| 153 | 4-methylphenyl | | $CH_2$ | 576.758 | 577 |
| 154 | 4-methylphenyl | | $CH_2$ | 578.774 | 579 |
| 155 | 4-methylphenyl | | $CH_2$ | 564.747 | 565 |
| 156 | 4-methylphenyl | | $CH_2$ | 606.82 | 607 |
| 157 | 4-methylphenyl | | $CH_2$ | 618.838 | 619 |
| 158 | 4-methylphenyl | | $CH_2$ | 612.791 | 613 |
| 159 | 4-methylphenyl | pyridin-3-yl | $CH_2$ | 518.635 | 519.4 |
| 160 | 4-methylphenyl | 3-(isobutylamino)prop-1-yn-1-yl | $CH_2$ | 550.72 | 551.3 |
| 161 | 4-methylphenyl | 3-cyanophenyl | $CH_2$ | 542.655 | 543.2 |
| 162 | 4-methylphenyl | piperidin-3-yl | $CH_2$ | 524.68 | 525.3 |
| 163 | 4-methylphenyl | pyridin-2-yl | $CH_2$ | 518.635 | 519.2 |
| 164 | 4-methylphenyl | piperidin-2-yl | $CH_2$ | 524.68 | 525.3 |
| 165 | 4-methylphenyl | 2-(3-methyl-1,2,4-oxadiazol-5-yl)phenyl | $CH_2$ | 599.71 | 600.5 |
| 166 | 4-methylphenyl | 1-(pyrrolidin-1-ylmethyl)ethen-1-yl | $CH_2$ | 550.72 | 551 |

-continued

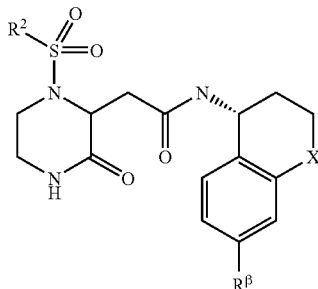

| No. | R² | Rᵝ | X | MW | MS data |
|---|---|---|---|---|---|
| 167 | 4-methylphenyl | 3-carbamoylphenyl | $CH_2$ | 560.67 | 561 |
| 168 | 4-methylphenyl | 3-(methoxycarbonyl)phenyl | $CH_2$ | 575.685 | 576 |
| 169 | 4-methylphenyl | 3-acetamidophenyl | $CH_2$ | 574.7 | 575 |
| 170 | 4-methylphenyl | 3-methylsulfonylphenyl | $CH_2$ | 595.74 | 596 |
| 171 | 4-methylphenyl | 3-(hydroxymethyl)phenyl | $CH_2$ | 547.675 | 548 |
| 172 | 4-methylphenyl | 3-(cyclobutylaminomethyl)phenyl | $CH_2$ | 600.78 | 601 |
| 173 | 4-methylphenyl | 3-carboxyphenyl | $CH_2$ | 561.655 | 562 |
| 174 | 4-methylphenyl | 3-fluoro-4-carboxyphenyl | $CH_2$ | 579.645 | 580 |
| 175 | 4-methylphenyl | 3-(isobutylaminomethyl)phenyl | $CH_2$ | 602.795 | 603 |
| 176 | 4-methylphenyl | 3-(cyclopentylaminomethyl)phenyl | $CH_2$ | 614.805 | 615 |
| 177* | 4-methylphenyl | 1-(piperidin-1-ylmethyl)ethen-1-yl | $CH_2$ | 564.747 | 565 |
| 178 | 4-methylphenyl | 2-(methoxycarbonyl)ethenyl | $CH_2$ | 525.625 | 526.4 |

The following compounds were made using the methods described in Example 25.

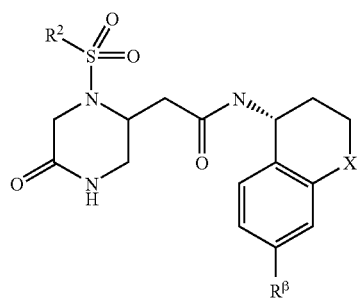

| No. | R² | Rᵝ | X | MW | MS data |
|---|---|---|---|---|---|
| 179 | 4-methylphenyl | piperidin-1-ylmethyl | $CH_2$ | 538.71 | 539.2 |
| 180 | 4-methylphenyl | 1-(piperidin-1-ylmethyl)ethenyl | $CH_2$ | 564.745 | 565.2 |
| 181 | 3,4-dichlorophenyl | piperidin-1-ylmethyl | $CH_2$ | 593.575 | 593.2, 595.2 |

The following compounds were made using the methods described in Examples 32 and 33.

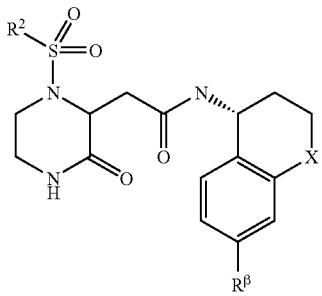

| No. | R² | Rᵝ | X | MW | MS data |
|---|---|---|---|---|---|
| 182 | 4-methylphenyl | 3-(isobutylamino)prop-1-yl | CH₂ | 554.75 | 555.4 |
| 183 | 4-methylphenyl | 3,3-bis(isobutylamino)-prop-1-yl | CH₂ | 610.86 | 611.4 |
| 184 | 4-methylphenyl | 3-((cyclopentylmethyl)-amino)prop-1-yl | CH₂ | 580.79 | 581.5 |
| 185 | 2,5-dimethyl-4-chlorophenyl | 3-aminopropyl | CH₂ | 547.115 | 548.3 |
| 186 | 2,5-dimethyl-4-chlorophenyl | 3-((pyridin-4-yl-methyl)amino)prop-3-yl | CH₂ | 638.23 | 639.4 |
| 187* | 4-methylphenyl | 3-aminopropyl | CH₂ | 498.645 | 499.5 |
| 188* | 4-methylphenyl | 3,3-bis(isobutylamino)-prop-1-yl | CH₂ | 610.859 | 611.3 |
| 189* | 4-methylphenyl | 3-(isobutylamino)prop-1-yl | CH₂ | 554.752 | 555.4 |
| 190 | 2,5-dimethyl-4-chlorophenyl | 3-((tetrahydro-2H-pyran-4-ylmethyl)amino)prop-3-yl | CH₂ | 645.26 | 645.3 |

The following compounds were made using the methods described in Example 18.

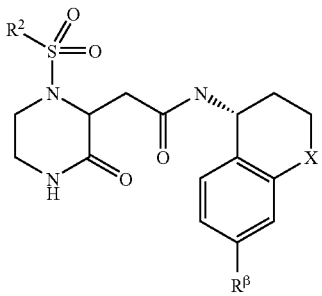

| No. | R² | Rᵝ | X | MW | MS data |
|---|---|---|---|---|---|
| 191 | 4-methylphenyl | 1-(piperidin-1-ylmethyl)ethenyl | CH₂ | 564.745 | 565 |
| 192 | 3-trifluoromethylphenyl | 1-(piperidin-1-ylmethyl)ethenyl | CH₂ | 604.735 | 605 |
| 193 | 4-methylphenyl | 1-(piperidin-1-ylmethyl)ethyl | CH₂ | 566.763 | 567 |
| 194 | 4-methylphenyl | 1-((isobutylamino)-methyl)ethenyl | CH₂ | 552.735 | 553 |
| 195 | 4-methylphenyl | 1-((tert-butylamino)-methyl)ethenyl | CH₂ | 552.735 | 553 |
| 196 | 4-methylphenyl | 1-(((cyclopropyl-methyl)amino)-methyl)ethenyl | CH₂ | 550.72 | 551 |
| 197 | 4-methylphenyl | 1-((cyclobutylamino)-methyl)ethenyl | CH₂ | 550.72 | 551 |

-continued

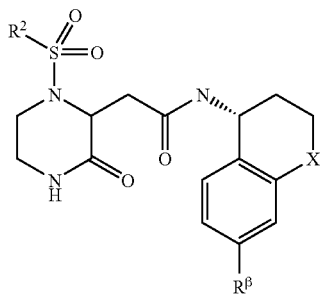

| No. | R² | Rᵝ | X | MW | MS data |
|---|---|---|---|---|---|
| 198 | 4-methylphenyl | 1-(azetidin-1-ylmethyl)ethenyl | CH₂ | 536.695 | 537 |
| 199 | 4-methylphenyl | 1-(4-fluoropiperidin-1-ylmethyl)ethenyl | CH₂ | 582.735 | 583 |
| 200 | 4-methylphenyl | 1-((2,2-dimethylpropyl-amino)methyl)ethenyl | CH₂ | 566.765 | 567 |
| 201* | 4-methylphenyl | 1-(pyrrolidin-1-ylmethyl)ethenyl | CH₂ | 550.72 | 551 |

The following compounds were made using the methods described in Example 30.

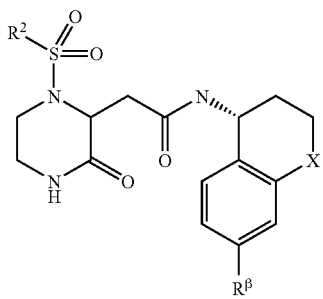

| No. | R² | Rᵝ | X | MW | MW data |
|---|---|---|---|---|---|
| 202 | 4-chlorophenyl | 2-piperidin-1-ylethyl | CH₂ | 573.155 | 573.2 |
| 203 | 4-chlorophenyl | 2-(isobutylamino)ethyl | CH₂ | 561.145 | 561.2 |
| 204 | 4-chlorophenyl | 2-(tert-butylamino)ethyl | CH₂ | 561.145 | 561.2 |
| 205 | 4-chlorophenyl | 2-((2,2-dimethyl-propyl)amino)ethyl | CH₂ | 575.17 | 575.2 |
| 206 | 4-chlorophenyl | 2-(cyclobutylamino)-ethyl | CH₂ | 559.13 | 559.2 |
| 207 | 4-chlorophenyl | 2-(benzylamino)ethyl | CH₂ | 595.16 | 595.2 |
| 208 | 4-chlorophenyl | 2-morpholin-4-ylethyl | CH₂ | 575.125 | 575.1 |
| 209 | 4-chlorophenyl | 2-pyrrolidin-1-ylethyl | CH₂ | 559.13 | 559.2 |
| 210 | 4-methylphenyl | (cyclopentylamino)-methyl | CH₂ | 538.71 | 539.4 |
| 211* | 4-methylphenyl | 2-piperidin-1-ylethyl | CH₂ | 552.736 | 553.2 |
| 212* | 4-chlorophenyl | 2-piperidin-1-ylethyl | CH₂ | 573.154 | 573.2 |

The following compounds were made using the methods described in Example 31.

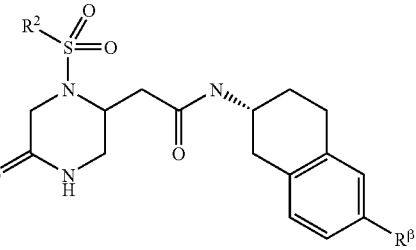

| No. | R² | Rᵝ | MW | MS data |
|---|---|---|---|---|
| 213 | 4-chlorophenyl | piperidin-1-ylmethyl | 559.13 | 559.2 |
| 214 | 4-chlorophenyl | 2-((2-pyrrolidin-1-ylethyl)amino)ethyl | 602.195 | 588.2 |

The following compounds were prepared using a procedure essentially as described above.

EXAMPLE 215

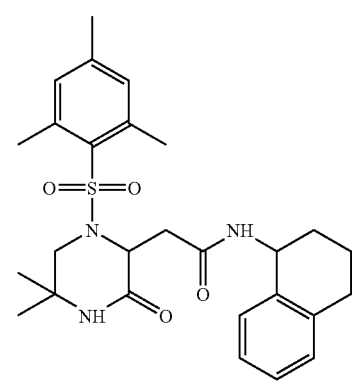

2-[5,5-Dimethyl-3-oxo-1-(2,4,6-trimethyl-benzene-sulfonyl)-piperazin-2-yl]-N-(1,2,3,4-tetrahydro-naphthalen-1-yl)-acetamide

EXAMPLE 216

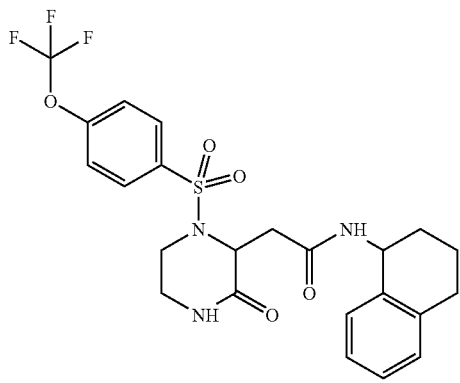

2-[3-Oxo-1-(4-trifluoromethoxy-benzenesulfonyl)-piperazin-2-yl]-N-(1,2,3,4-tetrahydro-naphthalen-1-yl)-acetamide

EXAMPLE 217

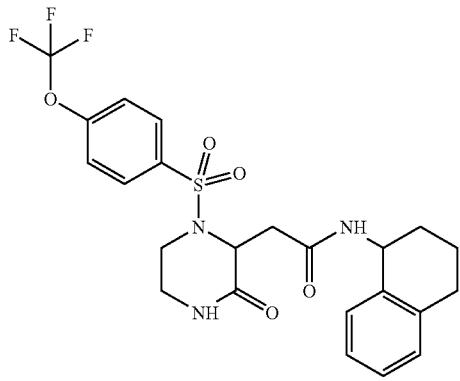

2-[3-Oxo-1-(4-trifluoromethoxy-benzenesulfonyl)-piperazin-2-yl]-N-(1,2,3,4-tetrahydro-naphthalen-1-yl)-acetamide

EXAMPLE 218

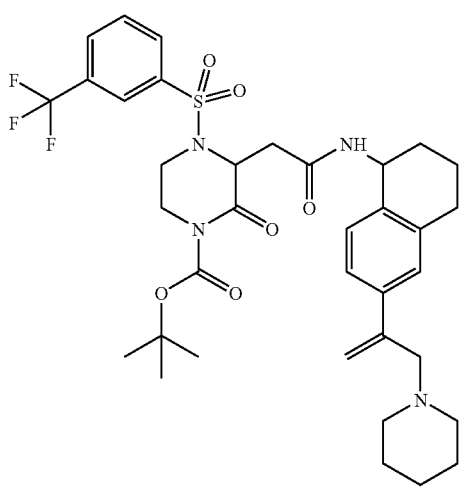

3-{[6-(1-Piperidin-1-ylmethyl-vinyl)-1,2,3,4-tetrahydro-naphthalen-1-ylcarbamoyl]-methyl}-4-(3-trifluoromethyl-benzenesulfonyl)-piperazine-1-carboxylic acid tert-butyl ester

EXAMPLE 219

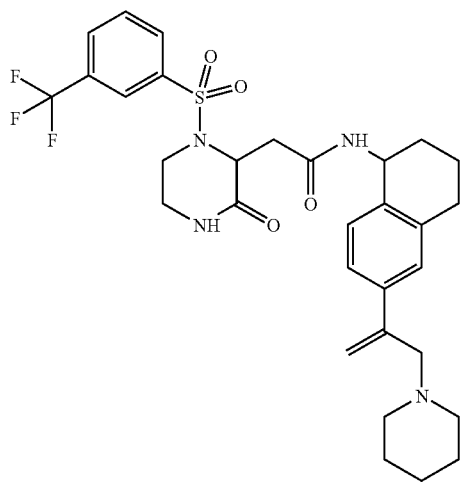

N-[6-(1-Piperidin-1-ylmethyl-vinyl)-1,2,3,4-tetrahydro-naphthalen-1-yl]-2-[1-(3-trifluoromethyl-benzenesulfonyl)-piperazin-2-yl]-acetamide

EXAMPLE 220

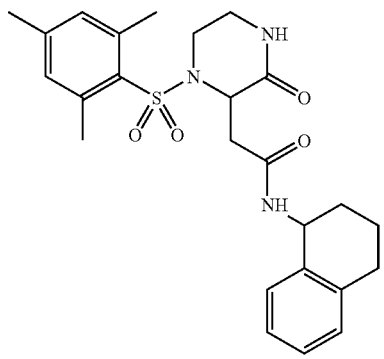

2-((2R)-3-oxo-1-((2,4,6-trimethylphenyl)sulfonyl)-2-piperazinyl)-N-((1R)-1,2,3,4-tetrahydro-1-naphthalenyl)acetamide

EXAMPLE 221

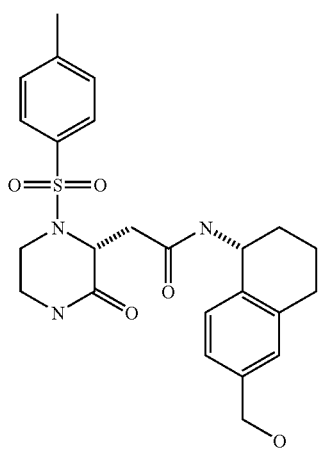

N-((1R)-6-(hydroxymethyl)-1,2,3,4-tetrahydro-1-naphthalenyl)-2-((2R)-1-((4-methylphenyl)sulfonyl)-3-oxo-2-piperazinyl)acetamide The following examples can be made using the above examples and generic schemes.

| R[7'] | p |
|---|---|
| piperidin-1-yl | 2 |
| (CH$_3$)$_2$N— | 1 |
| piperazin-1-yl | 1 |
| 4-CH$_3$-piperazin-1-yl | 1 |
| (Et$_2$)N— | 1 |
| (CH$_3$)(Et)N— | 2 |
| piperazin-1-yl | 2 |

TABLE 3

| R[7'] | p |
|---|---|
| piperidin-1-yl | 2 |
| (CH$_3$)$_2$N— | 1 |
| piperazin-1-yl | 1 |
| 4-CH$_3$-piperazin-1-yl | 1 |
| (Et$_2$)N— | 1 |
| 2-imidazolin-2-yl | 1 |
| (CH$_3$)(Et)N— | 2 |
| piperazin-1-yl | 2 |

TABLE 3-continued

R[2]

5,6,7,8-tetrahydronaphth-2-yl
2-quinolyl
phenyl
2-chlorophenyl
3-chlorophenyl
4-chlorophenyl
4-methoxyphenyl
3,5-dichlorophenyl
3-methoxyphenyl
3-fluorophenyl
3-biphenyl
4-biphenyl
3-methylphenyl
3-CF$_3$-phenyl
2,4,6-trichlorophenyl
2,3,4-trichlorophenyl
2,4,5-trichlorophenyl
3,4-dichlorophenyl
4-t-butylphenyl
1-naphthyl
4-methyl-1-naphthyl
phenyl-ethenyl
benzo[1,2,5]oxadiazol-5-yl
5-(dimethylamino)naphth-1-yl
5-chloro-3-methylphenyl
benzothiazol-2-yl
2,3,4,5,6-pentamethylphenyl
6-methoxy-2-naphthyl
3-chloro-4-methylphenyl
5-methoxy-3-methylbenzothien-2-yl
6-methoxy-3-methylbenzothien-2-yl
5-chloro-3-methylbenzothien-2-yl
3-methylbenzothien-2-yl
2,4-dichloro-5-methylphenyl
3,5-dichloro-4-methylphenyl
2,4-dichloro-3-methylphenyl
7-methoxy-2-naphthyl
6-fluoroethoxy-2-naphthyl
3-methyl-5-trifluoromethoxybenzofur-2-yl
3-methyl-5-methoxybenzofur-2-yl
5-chloro-benzo[1,2,5]oxadiazol-4-yl
3-methyl-5-trifluoromethoxybenzothien-2-yl
6-ethoxy-2-naphthyl
2-Cl-4-CF$_3$-phenyl
6-bromonaphthyl
3-methylbenzofur-2-yl
3-chlorobenzothien-2-yl
5-chloro-benzo[1,2,5]thiadiazol-4-yl
5-chloro-1,3-dimethyl-1H-pyrazol-4-yl
2,3-dichlorothien-5-yl
2,5-dichlorothien-3-yl
5-chloro-2-naphthyl
4-butoxyphenyl
3,5-di(trifluoromethyl)phenyl
5-(isoxazol-3-yl)thien-2-yl
2-chlorothien-5-yl
4-chloro-benzo[1,2,5]oxadiazol-7-yl
2,4-dichloro-6-methylphenyl
2,4,6-trimethylphenyl
2,5-dimethylphenyl

TABLE 3-continued 4-chloro-2,5-dimethylphenyl
2,5-dichlorophenyl
3,4-difluorophenyl
3-chloro-4-fluorophenyl
2-methyl-5-trifluoromethylphenyl
4-methylcyclohexyl
3,5-dimethylbenzothien-2-yl
5-fluoro-3-methylbenzothien-2-yl
5-methylbenzothien-2-yl
5-chloro-3-methylbenzofur-2-y
3-pyridyl

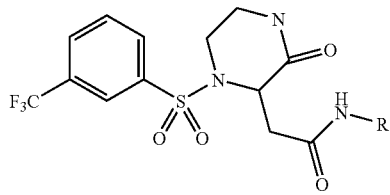

R 3-isopropyl-7-(1-methylpiperidin-2-yl)chroman-4-yl
2,2-dimethyl-7-(1-methylpiperidin-2-yl)chroman-4-yl
7-(piperidin-2-yl)chroman-4-yl
2,2-dimethyl-7-(methylaminomethyl)chroman-4-yl
7-(dimethylaminomethyl)-1,2,3,4-tetrahydonaphth-4-yl
7-(piperidin-1-ylaminomethyl)-1,2,3,4-tetrahydonaphth-2-yl
5-(piperidin-1-yl)methylindan-1-yl
6-(4-methylpiperazin-1-yl)methylindan-1-yl
4-(piperazin-1-yl)methylindan-1-yl
2-(di-ethylaminomethyl)-5,6,7,8-tetrahydoquinolin-5-yl
2-(isopropylaminomethyl)-5,6,7,8-tetrahydoquinolin-8-yl
2-(t-butylaminomethyl)-5,6,7,8-tetrahydoisoquinolin-8-yl
7-(morpholin-4-ylmethyl)-quinolin-4-yl
1-methyl-2-oxo-6-(piperidin-1-yl)methylindol-3-yl
7-(dimethylaminomethyl)-1,2,3,4-tetrahydonaphth-2-yl
7-(diethylaininomethyl)-4,5,6,7-tetrahydobenzofur-4-yl
7-(4-morpholinylmethyl)-4,5,6,7-tetrahydobenzothien-4-yl
7-(aminomethoxy)chroman-4-yl
4-4-(4,5-dihydro-1H-imidazol-2-yl)-phenylethyl
4-4-(4,5-dihydro-1H-imidazol-2-yl)-phenyl
4-(aminopropyl)phenyl
4-(aminoethyl)phenyl

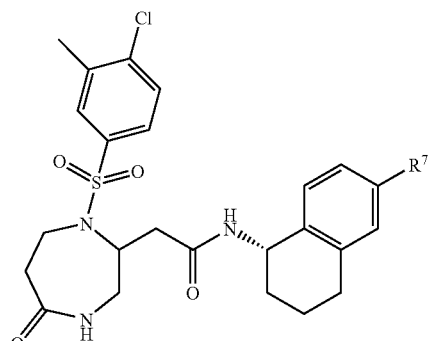

R[7]

piperidin-1-ylmethyl
CH$_3$NH-methyl
piperazin-1-yl-methyl
4-CH$_3$-piperazin-1-ylmethyl
(t-but)NH-methyl
(Et)NH-vinyl
1-methylpiperazin-1-yl-vinyl

TABLE 3-continued

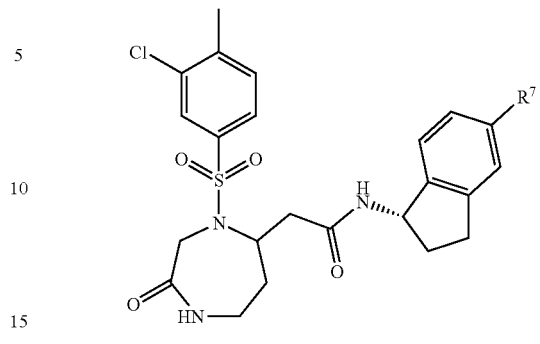

R[7]

piperidin-1-ylmethyl
CH$_3$NH-methyl
piperazin-1-yl-methyl
4-CH$_3$-piperazin-1-ylmethyl
(t-but)NH-methyl
(Et)NH-vinyl
1-methylpiperazin-1-yl-vinyl

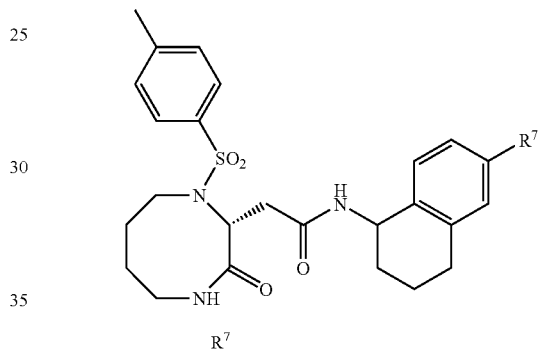

R[7]

piperidin-1-ylmethyl
CH$_3$NH-methyl
piperazin-1-yl-methyl
4-CH$_3$-piperazin-1-ylmethyl
(t-but)NH-methyl
(Et)NH-vinyl
1-methylpiperazin-1-yl-vinyl Although the pharmacological properties of the compounds of Formula I-VI vary with structural change, in general, activity possessed by compounds of Formula I-VI may be demonstrated in vivo. The pharmacological properties of the compounds of this invention may be confirmed by a number of pharmacological in vitro assays. The exemplified pharmacological assays, which follow, have been carried out with the compounds according to the invention and their salts. Compounds of the present invention showed binding IC$_{50}$'s of B1 at doses less than 20 µM.

Biological Testing

Human Bradykinin B1 Receptor and human B2 Receptor In Vitro Binding Assay Supporting Methods Preparation of Membranes Expressing Human B1 and Human B2 Bradykinin Receptor Membranes were prepared from CHO-d-AQN cells stably transfected with human bradykinin B1 receptor cDNA. For large-scale production of membranes, cells were grown in 100L suspension culture to 1.0E8 cells/mL then harvested using the Viafuge at continuous centrifugation of 1000 g. For pilot studies, cells were grown in 2 L spinner culture and harvested by centrifugation (1900 g, 10 min, 4° C.). The cell pellet was washed with PBS, centrifuged (1900 g, 10 min, 4° C.), then the cells resuspended in lysis buffer (25 mM HEPES, pH 7.4, 5 mM EDTA, 5 mM EGTA, 3 mM $MgCl_2$, 10% (w/v) sucrose, Complete Protease Inhibitor tablets (EDTA-free)) to a density of 14% w/v for passage through a microfluidizer (Microfluidics 110S, 3 passes, 6,000 psi). The resulting cell lysate was centrifuged (1900 g, 10 min, 4° C.), and the crude particulate fraction isolated by centrifugation (142,000 g, 1 h, 4° C.) of the low-speed supernatant. The resulting pellet was resuspended in ⅓ the original lysis buffer volume, homogenized, and recentrifuged as above. The membrane pellet was resuspended by homogenization in storage buffer (25 mM HEPES, pH 7.4, 3 mM $MgCl_2$, 10% (w/v) sucrose and Complete Protease Inhibitor tablets (EDTA-free)). Single-use aliquots were made and flash-frozen in liquid $N_2$ prior to storage at −80° C.

Membranes containing human bradykinin B2R were purchased from Receptor Biology (now Perkin Elmer Life Sciences). They were derived from a CHO-K1 line stably expressing the human B2 receptor developed by Receptor Biology and subsequently purchased by Amgen. For some studies, membranes were prepared in-house from this same cell line using the method described for human B1 receptor membranes, except cells were grown in roller bottles and harvested using Cellmate.

Radiolijand Binding Assay for Human B1 and Human B2 Bradykinin Receptor

Human B1 receptor binding assay was performed in 96-well polypropylene plates (Costar 3365) by adding 50 µl [$^3$H] des-arg$^{10}$ kallidin (NET 1064; Perkin Elmer Life Sciences) to 10 µl test compound diluted in 90 µl assay buffer (24 mM TES, pH 6.8, 1 mM 1,10 o-phenanthroline, 0.3% BSA, 0.5 mM Pefabloc SC, 2 µg/mL aprotinin, 5 µg/mL leupeptin, and 0.7 µg/mL pepstatin A). Membranes (50 µl) were added last. [$^3$H] des-arg$^{10}$ kallidin was diluted from stock into assay buffer to yield a final concentration of 0.3 nM in the assay but was adjusted as needed to ensure a concentration at or below the $K_d$ determined for each batch of receptor membranes. Nonspecific binding was defined with 2 µM des-Arg$^{10}$Leu$^9$ kallidin. Membranes were diluted in assay buffer to yield a final concentration of 0.068 nM hB1 receptor in the assay. Compounds were solubilized in either DMSO or dd$H_2O$, plated into polypropylene plates (Costar 3365), then serially diluted in either DMSO or dilution buffer (20 mM Hepes, pH 7.6, 0.1% BSA) to yield a final concentration of either 5% DMSO or no DMSO in the assay. The assay mixture was incubated with shaking for 1 hr at RT and then filtered through GF/C plates presoaked in 0.5% polyethyleneimine (Unifilter; Perkin Elmer Life Sciences) using a Filtermate 96-well harvester (Perkin Elmer Life Sciences). Filter plates were rapidly washed 6 times with 200 µl ice-cold buffer (50 mM Tris, pH 7.4), dried in a vacuum oven at 55° C. for 15-20 min, backed, and 40 µl per well of Microscint 20 was added. The plates were sealed and activity read on Topcount (Perkin Elmer Life Sciences) using a count time of 3 min per channel.

For human B2 bradykinin receptor, the same procedure was followed with the following exceptions: [$^3$H] bradykinin (NET706; Perkin Elmer Life Sciences) was used at a final concentration of ~0.2 nM and non-specific binding was defined with 2 µM bradykinin. Human B2 receptor concentration was 0.068 nM final in the assay.

Data Analysis

Data was analyzed in XLFit with the four-parameter logistic $y=A+((B-A)/(1+((C/x)^D)))$ and fit with the Levenburg-Marquardt algorithm. Raw cpm were converted to percent of control values prior to analysis (POC=((compound cpm— nonspecfic cpm)/(no-compound cpm—nonspecific cpm) *100)). $K_i$ values were determined from the $IC_{50}$ using the Cheng-Prusoff equation and $K_d$ values determined by direct saturation binding of the radioligands.

The compounds of examples 3b-3c, 4, 4b, 5a, 6, 6a, 7, 9-12, and 14 have binding Ki's to the hB1 receptor at a level below 1 µM. The compounds should have binding Ki's to the hB2 receptor at a level above 1 µM.

In Vitro B1-Inhibition Activity

In vitro Assay of Human B1 Receptor Function Using Calcium Flux

Activation of the $G_q$ linked B1 receptor results in an increase in intracellular calcium. The calcium sensitive photoprotein aequorin can, therefore, be used as an indicator of B1 receptor activation. Aequorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, $CO_2$, and light that can be detected by conventional luminometry.

A stable CHO D-/hB1/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1X Non-Essential Amino Acids (Gibco 11140-050), 1X Glutamine-Pen-Strep (Gibco 10378-016), and Hygromycin, 300 µg/mL (Roche 843555). 15-24 h prior to the luminometer assay, 25,000 cells/well (2.5E6 cells/10 mL/plate) were plated in 96-well black-sided clear bottom assay plates (Costar #3904).

Media was removed from the wells and replaced with 60 µl of serum free HAM's F12 with 30 mM HEPES (pH 7.5) and 15 µM coelenterazine (Coelenterazine h Luciferin #90608 from Assay Designs). The plates were incubated for 1.5-2 h. Ten point $IC_{50}$ compound plates containing 1:3 or 1:5 dilutions of antagonist compounds and an agonist activator plate (20 nM des-Arg10-Kallidin final concentration, $EC_{80}$) were prepared using Ham's F12 with 30 mM HEPES, pH 7.5. Following coelenterazine incubation, an automated flash-luminometer platform was used to dispense the B1 antagonist compounds (dissolved in DMSO and diluted with buffer to the desired concentration (final DMSO concentration <1% DMSO)) to the cell plate, a CCD camera situated underneath the cell plate took 12 images of the cell plate at 5 second intervals to determine if there was any agonist activity with the compounds. The hB1 agonist, des-Arg$_{10}$-Kallidin, was added to the cell plate and another 12 images were recorded to determine the $IC_{50}$ of the antagonist(s). The compounds of examples 3c, 7, and 9-12 have binding $IC_{50}$'s to hB1 receptor function at a level below 1 µM.

In Vitro Assay of hB2 Receptor Function Using Calcium Flux

The intracellular calcium flux induced by hB2 receptor activation was analyzed using an hB2 recombinant cell line (CHO-K1) purchased from PerkinElmer (Catalog Number: RBHB2C000EA) on a fluorometric imaging plate reader (FLIPR). The cells were cultured in T225 flask containing Ham's F12 Nutrient Mixture (Invitrogen Corp., Cat # 11765-047), 10% Fetal Clone II Bovine Serum (HyClone, Cat # SH3006603), 1 mM Sodium pyruvate (100 mM stock, Invitrogen Corp., Cat# 12454-013), and 0.4 mg/mL Geneticin (G418; 50 mg/mL active geneticin, Invitrogen, Cat# 10131-207). Culture medium was changed every other day. 24 h prior to the FLIPR assay, the hB2/CHO cells were washed once with PBS (Invitrogen, Cat.#) and 10 ML of Versene (1:5000, Invitrogen, Cat# 15040-066) was added to each flask. After 5 min incubation at 37° C., Versene was removed and cells were detached from the flask and resuspended in culture medium. Cells were counted and 25,000 cells/well were plated in 96-well black-sided clear bottom assay plates (Costar #3904). Cells were incubated in a 37° C. $CO_2$ incubator overnight.

The media was aspirated from the cells and replaced with 65 µl of dye-loading buffer. The loading buffer was prepared by diluting a stock solution of 0.5 mM Fluo-4 AM (Molecular Probes, dissolved in DMSO containing 10% [w/v] pluronic acid) to a concentration of 1 µM in Clear Dulbecco's Modified Eagle Medium (DMEM) containing 0.1% BSA, 20 mM HEPES, and 2.5 mM probenecid. The cells were dye-loaded for 1 h at RT. The excess dye was removed by washing the cells 2× with assay buffer. The assay buffer consists of Hank's Balanced Salt Solution (HBSS) containing 20 mM HEPES, 0.1% BSA, and 2.5 mM probenecid. After the wash cycles, a volume of 100 µL was left in each well, and the plate was ready to be assayed in the FLIPR System. Single point (10 µM final concentration) POC antagonist compound plates or ten point $IC_{50}$ compound plates containing 1:3 or 1:5 dilutions of antagonist compounds (dissolved in DMSO and diluted with buffer to the desired concentration (final DMSO concentration <1% DMSO)) and an agonist activator plate (0.3 nM bradykinin final concentration, $EC_{80}$) were prepared using assay buffer. The cell plate and the compound plates were loaded onto the FLIPR and during the assay, fluorescence readings are taken simultaneously from all 96 wells of the cell plate. Ten 1-second readings were taken to establish a stable baseline for each well, then 25 µL from the B1 antagonist plate was rapidly (50 µL/sec.) added. The fluorescence signal was measured in 1-second (1 min) followed by 6-second (2 min) intervals for a total of 3 min to determine if there is any agonist activity with the compounds. The B2 agonist, bradykinin, was added to the cell plate and another 3 min were recorded to determine the percent inhibition at 10 µM (POC plates) or the $IC_{50}$ of the antagonist.

Cell and Tissue Based In Vitro Assays of hB1 Receptor Binding

These studies established the antagonist activity of several compounds at the bradykinin B1 receptors in in vitro cell-based and isolated organ assays.

1. Rabbit endothelial cell B1-specific $PGI_2$ secretion Assay
2. B1 and B2 umblical vein Assay In Vitro B1-Inhibition Activity The effectiveness of the compounds as inhibitors of B1 activity (i.e., B1 "neutralization") can be evaluated by measuring the ability of each compound to block B1 stimulated CGRP and substance P release and calcium signaling in Dorsal Root Ganglion (DRG) neuronal cultures.

Dorsal Root Ganglion Neuronal Cultures

Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Mass.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$— and $Mg^{2+}$-free Dulbecco's phosphate buffered saline (DPBS), pH 7.4 (GibcoBRL). The DRG are dissociated into single cell suspension using a papain dissociation system (Worthington Biochemical Corp., Freehold, N.J.). Briefly, DRG are incubated in a digestion solution containing 20 U/mL of papain in Earle's Balanced Salt Solution (EBSS) at 37° C. for fifty minutes. Cells are dissociated by trituration through fire-polished Pasteur pipettes in a dissociation medium consisting of MEM/Ham's F12, 1:1, 1 mg/mL ovomucoid inhibitor and 1 mg/mL ovalbumin, and 0.005% deoxyribonuclease I (DNase). The dissociated cells are pelleted at 200×g for 5 min and re-suspended in EBSS containing 1 mg/mL ovomucoid inhibitor, 1 mg/mL ovalbumin and 0.005% DNase. Cell suspension is centrifuged through a gradient solution containing 10 mg/mL ovomucoid inhibitor, 10 mg/mL ovalbumin at 200×g for 6 min to remove cell debris, then filtered through a 88-µM nylon mesh (Fisher Scientific, Pittsburgh, Pa.) to remove any clumps. Cell number is determined with a hemocytometer, and cells are seeded into poly-ornithine 100 µg/mL (Sigma, St. Louis, Mo.) and mouse laminin 1 µg/mL (GibcoBRL)-coated 96-well plates at $10 \times 10^3$ cells/well in complete medium. The complete medium consists of minimal essential medium (MEM) and Ham's F12, 1:1, penicillin (100 U/mL), streptomycin (100 µg/mL), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 µM) and uridine (180 µM) are included in the medium. Two hours after plating, cells are treated with recombinant human O-B1 or recombinant rat P-B1 at a concentration of 10 mg/mL (0.38 nM). Positive controls comprising serial-diluted anti-B1 antibody (R&D Systems, Minneapolis, Minn.) are applied to each culture plate. Compounds are added at ten concentrations using 3.16-fold serial dilutions. All samples are diluted in complete medium before being added to the cultures. Incubation time is generally around 40 h prior to measurement of VR1 expression.

Measurement of VR1 Expression in DRG Neurons.

Cultures are fixed with 4% paraformaldehyde in Hanks' balanced salt solution for 15 min, blocked with Superblock (Pierce, Rockford, Ill.), and permeabilized with 0.25% Nonidet P40 (Sigma) in Tris.HCl (Sigma)-buffered saline (TBS) for 1 h at RT. Cultures are rinsed once with TBS containing 0.1% Tween 20 (Sigma) and incubated with rabbit anti-VR1 IgG (prepared at Amgen) for 1.5 h at RT, followed by incubation of Eu-labeled anti-rabbit second antibody (Wallac Oy, Turku, Finland) for 1 h at RT. Washes with TBS (3× five min with slow shaking) are applied after each antibody incubation. Enhance solution (150 mL/well, Wallac Oy) is added to the cultures. The fluorescence signal is measured in a time-resolved fluorometer (Wallac Oy). VR1 expression in samples treated with the compounds is determined by comparing to a standard curve of B1 titration from 0-1000 ng/mL. Percent inhibition (compared to maximum possible inhibition) of B1 effect on VR1 expression in DRG neurons is determined by comparing to controls that are not B1-treated.

In Vivo Antinociceptive Activity in Rat and Monkey Pain Models

Rat Neuropathic Pain Model

Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355-363, (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth., 53:55-63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with compounds (usually a screening dose of 60 mg/kg) or control diluent (PBS) once by s.c. injection and PWT was determined each day thereafter for 7 days.

Rat CFA Inflammatory Pain Model

Male Sprague-Dawley rats (200 g) are lightly anesthetized with isoflurane inhalant anesthesia and the left hindpaw is injected with complete Freund's adjuvant (CFA), 0.15 mL. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with compounds (usually a screening dose of 60 mg/kg) or control solution (PBS) once by s.c. injection and PWT is determined each day thereafter for 7 days. Average paw withdrawal threshold (PWT) is converted to percent of maximum possible effect (% MPE) using the following formula: % MPE=100 * (PWT of treated rats—PWT of control rats)/(15-PWT of control rats). Thus, the cutoff value of 15 g (148.1 mN) is equivalent to 100% of the MPE and the control response is equivalent to 0% MPE.

At the screening dose of 60 mg/kg, compounds in vehicle are expected to produce an antinociceptive effect with a PD relationship.

Green Monkey LPS Inflammation Model

The effectiveness of the compounds as inhibitors of B1 activity are evaluated in Male green monkeys (*Cercopithaecus aethiops St Kitts*) challenged locally with B1 agonists essentially as described by deBlois and Horlick (British Journal of Pharmacology, 132:327-335 (2002), which is hereby incorporated by reference in its entirety).

In order to determine whether compounds of the present invention inhibit B1 induced oedema the studies described below are conducted on male green monkeys (*Cercopithaecus aethiops St Kitts*) at the Caribbean Primates Ltd. experimental farm (St Kitts, West Indies). Procedures are reviewed and accepted by the Animal Care Commnittees of the CR-CHUM (Montreal, Canada) and of Caribbean Primates Ltd. (St Kitts, West Indies). Animals weighing 6.0±0.5 kg (n=67) were anaesthetized (50 mg ketamine $kg^{-1}$) and pretreated with a single intravenous injection of LPS (90 µg $kg^{-1}$) or saline (1 mL) via the saphenous vein.

Inflammation Studies

Kinin-induced oedema is evaluated by the ventral skin fold assay (Sciberras et al., 1987). Briefly, anaesthetized monkeys were injected with captopril (1 mg $kg^{-1}$ 30 min before assay). A single subcutaneous injection of dKD, BK or the vehicle (2 mM amastatin in 100 µl Ringer's lactate) is given in the ventral area and the increase in thickness of skin folds is monitored for 30-45 min using a calibrated caliper. The results are expressed as the difference between the skin fold thickness before and after the subcutaneous injection. Captopril and amastatin are used to reduce degradation of kinins at the carboxyl- and amino-terminus, respectively.

Antagonist Schild Analysis

The dose-response relationship for dKD (1-100 nmol)-induced oedema is determined at 24 h post-LPS in the absence or presence of different concentrations of antagonist. BK (30 nmol) is used as a positive control.

Antagonst Time Course

The time course of inhibition by antagonist is determined at 4, 24 and 48 h, 72 and/or 96 h after single bolus administration. BK (30 nmol) is used as a positive control.

Drugs

Ketamine hydrochloride, LPS, amastatin and captopril are from Sigma (MO, U.S.A.). All peptides are from Phoenix Pharmaceuticals (CA, U.S.A.).

Statistics

Values are presented as mean +standard error of the mean (s.e. mean). In edema studies, the pre-injection thickness of the skin folds was subtracted from the values after subcutaneous challenge. Curve fitting and EC50 calculations were obtained using the Delta Graph 4.0 software for Apple Computers. Data were compared by two-way analysis of variance followed by unpaired, one tail Student's t-test with Bonferroni correction. $P < 0.05$ was considered statistically significant.

Formulations

Also embraced within this invention is a class of pharmaceutical compositions comprising the active compounds of Formula I-V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

What is claimed is:

1. A compound of Formula I wherein q is 1;
wherein t is 1;
wherein X is selected from NH;
wherein R is selected from:
  a) 1,2,3,4-tetrahydronaphth-1-yl; or 1,2,3,4-tetrahydronaphth-2-yl which may be substituted with one to three basic moieties, and optionally substituted with one to three groups independently selected from halo, hydroxyl, cyano, oxo, $(C_1-C_6)$alkoxy, $(C_2-C_6)$alkenyl, $(C_2-C_6)$alkynyl, —C(O)$R^8$, —COO$R^8$, —C(O)N$R^8R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl wherein $R^1$ is selected from H, $C_{1-4}$-alkyl;
wherein $R^2$ is selected from aryl wherein $R^2$ is optionally substituted with one to five groups independently selected from halo, —NH$_2$, hydroxyl, cyano, $(C_1-C_6)$alkylamino, $(C_1-C_6)$alkoxy, $(C_2-C_6)$alkenyl, $(C_2-C_6)$alkynyl, —C(O)$R^8$, —COO$R^8$, —C(O)N$R^8R^{8'}$, —N$R^8$C(O)$R^{8'}$, or $(C_1-C_6)$alkyl;

wherein $R^3$, $R^{3a}$, $R^4$, $R^{4a}$, $R^5$ and $R^{5a}$ are independently selected from H, $C_{1-3}$ alkyl and substituted $C_{1-3}$ alkyl;
or wherein $R^3$ and $R^{3a}$ together form oxo, or $R^4$ and $R^{4a}$ together form oxo, or $R^5$ and $R^{5a}$ together form oxo;

wherein $R^8$ and $R^{8'}$ independently are H or selected from lower alkyl, aryl and heteroaryl, each of which is optionally substituted with one, two or three groups independently, selected from lower alkyl, halogen, lower alkoxy, hydroxy, amino, mono- or dialkylamino, and trifluoromethyl;

wherein $R^x$ is selected from H, $(C_1-C_3)$haloalkyl, and $(C_1-C_3)$alkyl; and wherein each substituted alkyl, substituted aryl, substituted heteroaryl, substituted cycloalkyl and substituted saturated or partially saturated heterocyclyl is substituted with one to three groups independently selected from halo, —NH$_2$, hydroxyl, cyano, $(C_1-C_6)$alkylamino, $(C_1-C_6)$haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, and —N$R^8$C(O)$R^{8'}$, or pharmaceutically acceptable salts thereto provided the basic substiuent is not 2-pyridyl, 3-pyridyl or 2-oxo-piperaziny-4-ylmethyl.

2. Compound of claim 1 wherein R is selected from 1,2,3,4-tetrahydronaphth-1-yl, or 1,2,3,4-tetrahydronaphth-2-yl substituted with one to two basic moieties, and optionally substituted with one to three groups independently selected from halo, hydroxyl, cyano, oxo, $(C_1-C_6)$alkoxy, $(C_2-C_6)$alkenyl, $(C_2-C_6)$alkynyl, —C(O)$R^8$, —COO$R^8$, —C(O)N$R^8R^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl.

3. The compound of claim 2 wherein R is selected from 1,2,3,4-tetrahydronaphth-1-yl or 1,2,3,4-tetrahydronaphth-2-yl substituted with a basic moiety, optionally substituted with chloro.

4. Compound of claim 1 wherein $R^1$ is H or methyl.

5. Compound of claim 1 wherein $R^2$ is selected from naphthyl or phenyl wherein $R^2$ is optionally substituted with one to five groups independently selected from halo, —NH$_2$, hydroxyl, cyano, $(C_1-C_6)$alkylamino, $(C_1-C_6)$alkoxy, $(C_2-C_6)$alkenyl, $(C_2-C_6)$alkynyl, —C(O)$R^8$, —COO$R^8$, —C(O)N$R^8R^{8'}$, —N$R^8$C(O)$R^{8'}$, or $(C_1-C_6)$alkyl.

6. Compound of claim 1 wherein $R^2$ is selected from 2,4,6-trimethylphenyl, 3,4-dichlorophenyl, 3-chloro-4-methylphenyl, 4-chloro-3-methylphenyl, 4-methoxyphenyl, 4-methylphenyl, 4-chlorophenyl and 4-tert-butylphenyl.

7. Compound of claim 1 wherein the basic substituent on R is selected from amino, cycloalkylamino$(C_1-C_6)$alkyl, cycloalkyl$(C_1-C_6)$alkylamino$(C_1-C_6)$alkyl, heterocyclylamino$(C_1-C_6)$alkyl, heterocyclyl$(C_1-C_6)$alkylamino$(C_1-C_6)$alkyl, arylamino$(C_1-C_6)$alkyl, aryl$(C_1-C_6)$alkylamino$(C_1-C_6)$alkyl, $C_{1-6}$-alkylamino-$C_{1-6}$-alkoxy, $C_{1-6}$-alkylamino-$C_{1-6}$-alkoxy-$C_{1-6}$-alkoxy, amino$(C_1-C_6)$alkoxy, amino$(C_1-C_6)$alkyl, $(C_1-C_6)$alkylamino$(C_1-C_6)$alkyl, $C_{1-4}$-alkylamino-$C_{2-6}$-alkenyl, di-$C_{1-4-alkylamino-C2-4-alkenyl}$, 5-8 membered nitrogen-containing heterocyclyl-$C_{2-6}$-alkenyl, heterocyclyl-$(C_1-C_6)$alkylamino$(C_2-C_6)$alkyl, 5-6 membered heterocycly-loxy, 5-6 membered nitrogen-containing heterocyclyl and 5-7 membered nitrogen-containing heterocyclyl-alkyl; and wherein each of said basic substituents is optionally substituted with one to three groups independently selected from halo, —NH$_2$, hydroxyl, cyano, —CF$_3$, $(C_1-C_6)$alkylamino, oxo, $(C_1-C_6)$alkoxy, $(C_2-C_6)$alkenyl, $(C_2-C_6)$alkynyl, di$(C_1$-

$C_6$)alkylamino, —C(O)R$^8$, —COOR$^8$, —C(O)NR$^8$R$^{8'}$, —NR$^8$C(O)R$^{8'}$, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —NH$_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)R$^8$, —COOR$^8$, —C(O)NR$^8$R$^{8'}$, and —NR$^8$C(O)R$^{8'}$.

8. The compound of claim 7 wherein the basic substituent on R is selected from amino, mono-$C_{1-4}$-alkylamino-$C_{1-4}$ alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocycyl-$C_{2-4}$-alkenyl, optionally substituted 5-6 membered nitrogen-containing heterocyclyl and 5-8 membered nitrogen-containing heterocyclyl-$C_{1-4}$-alkyl.

9. The compound of claim 8 wherein the basic substituent on R is selected from amino, aminomethyl, isopropylaminomethyl, t-butylaminomethyl, 2-t-butylaminomethyl, 2-tert-butylamino-1-methyl-ethyl, 1-tert-butylaminoethyl, 1-(tert-butylamino-methyl)-vinyl, 1-piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropyl-aminomethyl, N,N-di(isopropyl)aminomethyl, N,N-dimethylaminomethyl, N,N-diethyl-aminomethyl, N,N-di(t-butyl)-aminomethyl, cyclopropylaminomethyl, cyclopropylaminomethyl, cyclopropylmethylaminomethyl, cyclopropylmethylaminomethyl, cyclobutylaminomethyl, cyclobutylaminoetyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-methyl, 4-(piperidin-1-yl)piperidinylmethyl, 4-(dimethylamino)-piperidin-1-ylmethyl, 2,6-dimethylpiperidin-1-ylmethyl, 4-morpholinylmethyl, 1-pyrrolidinylmethyl, 2-methylpyrrolidin-1-methyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl.

10. The compound of claim 1 wherein R$^3$ and R$^{3a}$ together form oxo; wherein R$^4$ and R$^{4a}$ are independently selected from H and $C_{1-3}$ alkyl; and wherein R$^5$ and R$^{5a}$ are independently H.

11. The compound of claim 10 wherein R$^3$ and R$^{3a}$ together form oxo; wherein R$^4$ and R$^{4a}$ are independently selected from H and methyl; and wherein R$^2$ and R$^{5a}$ are independently H.

12. The compound of claim 1 wherein R$^8$ and R$^{8'}$ independently are H or selected from lower alkyl, aryl and heteroaryl, each of which is optionally substituted with one, two or three groups independently selected from lower alkyl, halogen, lower alkoxy, hydroxy, amino, mono-alkylamino, dialkylamino, and trifluoromethyl.

13. Compound of claim 1 wherein R$^x$ is H, methyl or trifluoromethyl.

14. Compound of claim 1 wherein R$^x$ is H.

15. A compound of Formula III:

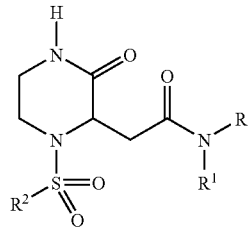

wherein R is selected from 1,2,3,4-tetrahydronaphth-1-yl or 1,2,3,4-tetrahydronaphth-2-yl substituted with one to two basic moieties, and optionally substituted with one to three groups independently selected from halo, hydroxyl, cyano, oxo, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, ($C_1$-$C_6$alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted ($C_1$-$C_6$)alkyl, substituted aryl, substituted heteroaryl, substituted cycloalkyl and substituted saturated or partially saturated heterocyclyl is substituted with one to three groups independently selected from halo, —NH$_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)R$^8$, —COOR$^8$, —C(O)NR$^8$R$^{8'}$, and —NR$^8$C(O)R$^{8'}$;

wherein R$^1$ is selected from H, and $C_{1-2}$-alkyl;

wherein R$^2$ is selected from aryl wherein R$^2$ is optionally substituted with one to five groups independently selected from halo, —NH$_2$, hydroxyl, cyano, ($C_1$-$C_6$)alkylamino, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, or ($C_1$-$C_6$)alkyl; and wherein R$^8$ and R$^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; or pharmaceutically acceptable salts thereof; provided the basic substiuent is not 2-pyridyl, 3-pyridyl or 2-oxo-piperaziny-4-ylmethyl.

16. The compound of claim 15 wherein R is selected from 1,2,3,4-tetrahydronaphth-1-yl or 1,2,3,4-tetrahydronaphth-2-yl substituted with a basic moiety, optionally substituted with chloro.

17. The compound of claim 15 wherein each R$^2$ is selected from naphthyl or phenyl wherein R$^2$ is optionally substituted with one to five groups independently selected from halo, —NH$_2$, hydroxyl, cyano, ($C_1$-$C_6$)alkylamino, ($C_1$-$C_6$)alkoxy, ($C_2$-$C_6$)alkenyl, ($C_2$-$C_6$)alkynyl, —C(O)R$^8$, —COOR$^8$, —C(O)NR$^8$R$^{8'}$, —NR$^8$C(O)R$^{8'}$, or ($C_1$-$C_6$)alkyl;

wherein R$^1$ is selected from H and $C_{1-2}$-alkyl;

wherein the basic substituent on R is selected from amino, cycloalkylamino($C_1$-$C_6$)alkyl, cycloalkyl($C_1$-$C_6$)alkylamino($C_1$-$C_6$)alkyl, heterocyclylamino($C_1$-$C_6$)alkyl, heterocyclyl($C_1$-$C_6$)alkylamino($C_1$-$C_6$)alkyl, arylamino($C_1$-$C_6$)alkyl, aryl($C_1$-$C_6$)alkylamino($C_1$-$C_6$) alkyl, $C_{1-6}$-alkylamino-$C_{1-6}$-alkoxy, $C_{1-6}$-alkylamino-$C_{1-6}$-alkoxy-$C_{1-6}$-alkoxy, amino($C_1$-$C_6$)alkoxy, amino ($C_1$-$C_6$)alkyl, ($C_1$-$C_6$)alkylamino($C_1$-$C_6$)alkyl, $C_{1-4}$-alkylamino-$C_{2-6}$-alkenyl, di-$C_{1-4}$-alkylamino-$C_{2-4}$-alkenyl, 5-8 membered nitrogen-containing heterocyclyl-$C_{2-6}$-alkenyl, heterocyclyl-($C_1$-$C_6$)alkylamino($C_2$-$C_6$)alkyl, 5-6 membered heterocyclyloxy, 5-6 membered nitrogen-containing heterocyclyl and 5-8 membered nitrogen-containing heterocyclyl-alkyl; and wherein each of said basic substituents is optionally substituted with one to three groups independently selected from halo, —$NH_2$, hydroxyl, cyano, —$CF_2$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —$NR^8$C(O)$R^{8'}$, ($C_1$-$C_6$) alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted ($C_1$-$C_6$)alkyl, substituted aryl substituted heteroaryl and substituted saturated or partially saturated heterocyclyl is optionally substituted with one to three groups independently selected from halo, —$NH_2$, hydroxyl, cyano, ($C_1$-$C_4$)alkylamino, ($C_1$-$C_4$)haloalkyl, oxo, ($C_1$-$C_4$) alkoxy, ($C_1$-$C_4$)alkoxy($C_1$-$C_4$)alkyl, ($C_2$-$C_4$)alkenyl, ($C_2$-$C_4$)alkynyl, di($C_1$-$C_4$)alkylamino, —C(O)$R^8$, —COO$R^8$, —C(O)N$R^8R^{8'}$, and —$NR^8$C(O)$R^{8'}$.

18. The compound of claim 17 wherein $R^2$ is selected from 2-naphthyl or phenyl wherein each $R^2$ is optionally substituted; 
wherein $R^1$ is H; and
wherein the basic substituent on R is selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-($C_2$-$C_4$)-alkenyl, di-$C_{1-4}$-alkylamino-($C_2$-$C_4$)-alkenyl, 5-8 membered nitrogen-containing heterocyclyl-($C_2$-$C_4$)-alkenyl, optionally substituted 5-6 membered nitrogen-containing heterocyclyl and 5-8 membered nitrogen-containing heterocyclyl-$C_{1-4}$-alkyl.

19. The compound of claim 15 wherein $R^1$ is H.

20. The compound of claim 15 wherein the basic substituent on R is selected from amino, aminomethyl, isopropylaminomethyl, t-butylaminomethyl, 2-t-butylaminomethyl, 2-tert-butylamino-1-methyl-ethyl, 1-tert-butylaminomethyl, 1-(tert-butylamino-methyl)-vinyl, 1-(piperidin-1-ylmethyl)-vinyl, N-isobutyl-aminoethyl, N-isobutyl-aminomethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methyl-aminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxy-piperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl.

21. The compound of claim 15 or pharmaceutically acceptable salts thereof selected from:
2-[3-Oxo-1-(2,4,6-trimethylbenzenesulfonyl)-piperizin-2(R,S)-yl]-N-(1,2,3,4-tetrahydronaphthalen-1-yl)-acetamide;
N-((1R)-6-(((1,1-Dimethylethyl)amino)methyl}-1,2,3,4-tetrahydro-1-naphthalenyl)-2-((2R,S)-1-((4-methylphenyl)sulfonyl)-3-oxo-2-piperazinyl)acetamide; and
2-[3-Oxo-1-(toluene-4-sulfonyl)piperizin-2-yl]-N-(6-piperidin-1-ylmethyl-1,2,3,4-tetrahydronaphthalen-1-yl)-acetamide.

22. A compound of Formula IV

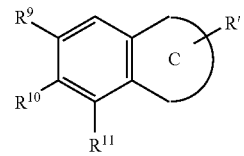

IV wherein the C ring is a 6 membered saturated carbocyclic moiety; optionally substituted with halo, hydroxyl, cyano, oxo, ($C_1$-$C_6$)alkoxy, ($C_2$-$C_6$)alkenyl, ($C_2$-$C_6$) alkynyl, —C(O)$R^8$, —COO$R^8$, —C(O)N$R^8R^{8'}$, —($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl;
wherein $R^1$ is selected from

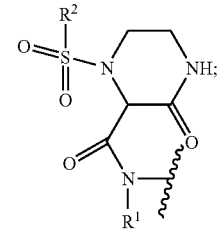

wherein $R^1$ is independently selected from H and $C_{1-2}$alkyl;
wherein $R^2$ is selected from aryl wherein $R^2$ is optionally substituted with one to five groups independently selected from halo, —$NH_2$, hydroxyl, cyano, ($C_1$-$C_6$) alkylamino, ($C_1$-$C_6$)alkoxy, ($C_2$-$C_6$)alkenyl, ($C_2$-$C_6$) alkynyl, —C(O)$R^8$, —COO$R^8$, —C(O)N$R^8R^{8'}$, —$NR^8$C(O)$R^{8'}$, or ($C_1$-$C_6$)alkyl;
wherein $R^8$ and $R^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl; and
wherein $R^9$, $R^{10}$ and $R^{11}$ are the same or different and represent H, halo, —$NH_2$, hydroxyl, cyano, —$CF_3$, ($C_1$-$C_6$)alkylamino, ($C_1$-$C_6$)alkoxy, ($C_2$-$C_6$)alkenyl, ($C_2$-$C_6$) alkynyl, di($C_1$-$C_6$)alkylamino, —C(O)$R^8$, —COO$R^8$, —C(O)N$R^8R^{8'}$, a basic moiety, ($C_1$-$C_6$)alkyl, substituted ($C_1$-$C_6$)alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted ($C_1$-$C_6$)alkyl, substituted aryl, substituted heteroaryl, substituted cycloalkyl and substituted saturated or partially saturated heterocyclyl is substituted with one to three groups independently selected from halo, —$NH_2$, hydroxyl, cyano, ($C_1$-$C_6$)alkylamino, ($C_1$-$C_6$)haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —$C(O)R^8$, —$COOR^8$, —$C(O)NR^8R^{8'}$, and —$NR^8C(O)R^{8'}$;

and pharmaceutically acceptable salts thereof provided at least one of $R^9$, $R^{10}$ and $R^{11}$ is a basic moiety; further provided the basic substiuent is not 2-pyridyl, 3-pyridyl or 2-oxo-piperaziny-4-ylmethyl.

23. The compound of claim 22 wherein $R^9$ and $R^{11}$ are H; and
wherein $R^{10}$ is selected from amino, aminomethyl, isopropylaminomethyl, t-butylaminomethyl, 2-t-butylaminomethyl, 2-tert-butylamino-1-methyl-ethyl, 1-tert-butylaminomethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6yl)methyl, 2-piperidinyl and 4-methylpiperazin-1-ylmethyl.

24. The compound of claim 22 wherein $R^{10}$ and $R^{11}$ are H; and
wherein $R^9$ is selected from amino, aminomethyl, isopropylaminomethyl, t-butylaminomethyl, 2-t-butylaminomethyl, 2-tert-butylamino-1-methyl-ethyl, 1-tert-butylaminomethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinyl-methyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6yl)methyl, 2-piperidinyl and 4-methylpiperazin-1-ylmethyl.

25. The compound of claim 22 wherein $R^9$ and $R^{10}$ are H; and
wherein $R^{11}$ is selected from amino, aminomethyl, isopropylaminomethyl, t-butylaminomethyl, 2-t-butylaminomethyl, 2-tert-butylamino-1-methyl-ethyl, 1-tert-butylaminomethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinyl-methyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6yl)methyl, 2-piperidinyl and 4-methylpiperazin-1-ylmethyl.

26. The compound of claim 22 wherein $R^2$ is selected from 2-naphthyl or phenyl wherein each $R^2$ is optionally substituted with one to five groups independently selected from halo, —$NH_2$, hydroxyl, cyano, ($C_1$-$C_6$)alkyl-amino, ($C_1$-$C_6$)alkoxy, ($C_2$-$C_6$)alkenyl, ($C_2$-$C_6$)alkynyl, —$C(O)R^8$, —$COOR^8$, —$C(O)NR^8R^{8'}$, —$NR^8C(O)R^{8'}$, or ($C_1$-$C_6$)alkyl.

27. The compound of claim 22 wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 3-chloro-4-methylphenyl, 4-chloro-3-methylphenyl, and 3-methylphenyl.

28. The compound of claim 22 wherein $R^1$ is H or methyl.

29. The compound of claim 22 wherein $R^2$ is 2-naphthyl.

30. The compound of claim 22 wherein $R^2$ is 3,4-dichlorophenyl.

31. A compound of Formula VI:

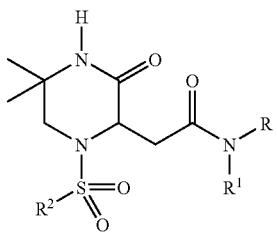

VI wherein R is selected from 1,2,3,4-tetrahydronaphth-1-yl or 1,2,3,4-tetrahydronaphth-2-yl substituted with one to two basic moieties, and optionally substituted with one to three groups independently selected from halo, hydroxyl, cyano, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, $(C_1-C_6)$alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl; wherein each substituted, $(C_1-C_6)$alkyl, substituted aryl, substituted heteroaryl, substituted cycloalkyl and substituted saturated or partially saturated heterocyclyl is substituted with one to three groups independently selected from halo, —NH$_2$, hydroxyl, cyano, $(C_1-C_6)$alkylamino, $(C_1-C_6)$haloalkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$^8$, —COOR$^8$, —C(O)NR$^8$R$^{8'}$, and —NR$^8$C(O)R$^{8'}$;

wherein R$^1$ is selected from H, and $C_{1-2}$-alkyl;

wherein R$^2$ is aryl wherein R$^2$ is optionally substituted with one to five groups independently selected from halo, —NH$_2$, hydroxyl, cyano, $(C_1-C_6)$alkylamino, oxo, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, or $(C_1-C_6)$ alkyl; and wherein R$^8$ and R$^{8'}$ independently are H or selected from lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable salts thereof; provided the basic substiuent is not 2-pyridyl, 3-pyridyl or 2-oxopiperaziny-4-ylmethyl.

32. The compound of claim 31 wherein R is selected from 1,2,3,4-tetrahydronaphth-1-yl or 1,2,3,4-tetrahydronaphth-2-yl substituted with a basic moiety, optionally substituted with chloro.

33. The compound of claim 31 wherein R$^2$ is naphthyl, or phenyl wherein R$^2$ is optionally substituted with one to five groups independently selected from halo, —NH$_2$, hydroxyl, cyano, $(C_1-C_6)$alkylamino, $(C_1-C_6)$alkoxy, $(C_2-C_6)$alkenyl, $(C_2-C_6)$alkynyl, —C(O)R$^8$, —COOR$^8$, —C(O)NR$^8$R$^{8'}$, —NR$^8$C(O)R$^{8'}$, or $(C_1-C_6)$alkyl wherein R$^1$ is selected from H and $C_{1-2}$-alkyl;

wherein the basic substituent on R is selected from amino, cycloalkylamino$(C_1-C_6)$alkyl, cycloalkyl$(C_1-C_6)$alkylamino$(C_1-C_6)$alkyl, heterocyclylamino$(C_1-C_6)$alkyl, heterocyclyl$(C_1-C_6)$alkylamino$(C_1-C_6)$alkyl, aryl amino$(C_1-C_6)$alkyl, aryl$(C_1-C_6)$alkylamino$(C_1-C_6)$alkyl, $C_{1-6}$-alkylamino-$C_{1-6}$-alkoxy, $C_{1-6}$-alkylamino-$C_{1-6}$-alkoxy-$C_{1-6}$-alkoxy, amino$(C_1-C_6)$alkoxy, amino $(C_1-C_6)$alkyl, $(C_1-C_6)$alkylamino$(C_1-C_6)$alkyl, $C_{1-4}$-alkylamino-$C_{2-6}$-alkenyl, di-$C_{1-4-alkylamino-C}$-hd 2-4-alkenyl, 5-8 membered nitrogen-containing heterocyclyl-$C_{2-6}$-alkenyl, heterocyclyl-$(C_1-C_6)$alkylamino$(C_2-C_6)$alkyl, 5-6 membered heterocyclyloxy, 5-6 membered nitrogen-containing heterocyclyl and 5-7 membered nitrogen-containing heterocyclyl-alkyl; and wherein each of said basic substituents is optionally substituted with one to three groups independently selected from halo, —NH$_2$, hydroxyl, cyano, —CF$_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)R$^8$, —COOR$^8$, —C(O)NR$^8$R$^{8'}$, —NR$^8$C(O)R$^{8'}$, $(C_1-C_6)$ alkyl, substituted $(C_1-C_6)$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $(C_1-C_6)$alkyl, substituted aryl substituted heteroaryl and substituted saturated or partially saturated heterocyclyl is optionally substituted with one to three groups independently selected from halo, —NH$_2$, hydroxyl, cyano, $(C_1-C_4)$alkylamino, $(C_1-C_4)$haloalkyl, oxo, $(C_1-C_4)$ alkoxy, $(C_1-C_4)$alkoxy$(C_1-C_4)$alkyl, $(C_1-C_4)$alkyl, $(C_2-C_4)$alkenyl, $(C_2-C_4)$alkynyl, di$(C_1-C_4)$alkylamino, —C(O)R$^8$, —COOR$^8$, —C(O)NR$^8$R$^{8'}$, and —NR$^8$C(O)R$^{8'}$.

34. The compound of claim 33 wherein R$^2$ is 2-naphthyl or phenyl wherein each R$^2$ is optionally substituted;

wherein R$^1$ is H; and wherein the basic substituent on R is selected from amino, mono-CC$_{1-4}$-alkylamino-C$_{1-4}$-alkyl, di-C$_{1-4}$-alkylamino-C$_{1-4}$-alkyl, mono-C$_{1-4}$-alkylamino-C$_{2-4}$-alkenyl, di-C$_{1-4}$-alkylamino-C$_{2-4}$-alkenyl, 5-8 membered nitrogen-containing heterocyclyl-C$_{2-4}$-alkenyl, optionally substituted 5-6 membered nitrogen-containing heterocyclyl and 5-8 membered nitrogen-containing heterocyclyl-C$_{1-4}$-alkyl;

and pharmaceutically acceptable derivatives thereof.

35. The compound of claim 31 wherein R$^1$ is H.

36. The compound of claim 31 wherein the basic substituent on R is selected from amino, aminomethyl, isopropylaminomethyl, t-butylaminomethyl, 2-t-butylaminomethyl, 2-tert-butylamino-1-methyl-ethyl, 1-tert-butylaminomethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinylmethyl, 4-(dimethylamino)piperidin-1-methyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6yl)methyl, 2-piperidinyl and 4-methylpiperazin-1-ylmethyl.

37. The compound of claim 31 or pharmaceutically acceptable salts thereof selected from:

2-((2R,S)-5,5-dimethyl-3-oxo-1-((2,4,6-trimethylphenyl) sulfonyl)-2-piperazinyl)-N-(1,2,3,4-tetrahydro-1-naphthalenyl)acetamide;

N-[6-(tert-Butylamino-methyl)-1,2,3,4-tetrahydro-naphthalen-1-yl]-2-[5,5-dimethyl-3-oxo-1-(2,4,6-trimethyl-benzenesulfonyl)-piperazin-2(R,S)-yl]-acetamide N-((1R,S)-6-(((1,1-dimethylethyl)amino)methyl)-1,2,3,4-tetrahydro-1-naphthalenyl)-2-((2R,S)-5,5-dimethyl-1-((4-methylphenyl)sulfonyl)-3-oxo-2-piperazinyl)acetamide; and 2-[5,5-Dimethyl-3-oxo-1-(toluene-4-sulfonyl)-piperizin-2(R,S)-yl]-N-(6-piperidin-1-ylmethyl-1,2,3,4-tetrahydronaphthalen-1(R)-yl)-acetamide.

38. The compound of claim 1 or pharmaceutically acceptable salts thereof selected from:

2-((2R)-1-((4-methylphenyl)sulfonyl)-3-oxo-2-piperazinyl)-N-((1R)-6-((1R,S)-1-((2-methylpropyl)amino)ethyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1,2,3,6-tetrahydro-4-pyridinyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-(2-methylpropyl)-1,2,3,6-tetrahydro-4-pyridinyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-propyl-1,2,3,6-tetrahydro-4-pyridinyl)-1,2,3,4-tetrahydro-1-naphthalenyl)acetamide;

2-((2R)-1-((4-methylphenyl)sulfonyl)-3-oxo-2-piperazinyl)-N-((1R)-6-((1R,S)-1-((2-methylpropyl)amino)ethyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-(phenylmethyl)-1,2,3,6-tetrahydro-4-pyridinyl)-1,2,3,4-tetrahydro-1-naphthalenyl)acetamide;

2-((2R)-1-((4-methylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((4-methylphenyl)sulfonyl)-5-oxo-2-piperazinyl)-N-((1R)-6-(1-piperidinylmethyl)-1,2,3,4-tetrahydro-1-naphthalenyl)acetamide;

2-((2R,S)-1-((4-methylphenyl)sulfonyl)-5-oxo-2-piperazinyl)-N-((1R)-6-(1-(1-piperidinylmethyl)ethenyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(3-pyridinyl)-1,2,3,4-tetrahydro-1-naphthalenyl)acetamide;

2-(1-((4-methylphenyl)sulfonyl)-3-oxo-2-piperazinyl)-N-((1R)-6-(3-((2-methylpropyl)amino)-1-propynyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(3-((2-methylpropyl)amino)propyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(3-piperidinyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(2-pyridinyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(2-piperidinyl)-1,2,3,4-tetrahydro-1-naphthalenyl)acetamide;

2-((2R)-1-((4-methylphenyl)sulfonyl)-3-oxo-2-piperazinyl)-N-((1R)-6-(3-((2-methylpropyl)amino)propyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-(1-piperidinylmethyl)ethenyl)-1,2,3,4-tetrahydro-1-naphthalenyl)acetamide;

2-((2R,S)-1-((4-methylphenyl)sulfonyl)-3-oxo-2-piperazinyl)-N-((1R)-6-((1S)-1-methyl-2-(1-piperidinyl)ethyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-(((2-methylpropyl)amino)methyl)ethenyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-(1-pyrrolidinylmethyl)ethenyl)-1,2,3,4-tetrahydro-1-naphthalenyl)acetamide;

3-((5R)-5-((((2R,S)-1-((4-methylphenyl)sulfonyl)-3-oxo-2-piperazinyl)acetyl)amino)-5,6,7,8-tetrahydro-2-naphthalenyl)benzamide;

methyl 3-((5R)-5-((((2R,S)-1-((4-methylphenyl)sulfonyl)-3-oxo-2-piperazinyl)acetyl)amino)-5,6,7,8-tetrahydro-2-naphthalenyl)benzoate;

2-((2R,S)-1-((4-methylphenyl)sulfonyl)-3-oxo-2-piperazinyl)-N-((1R)-6-(3-(methylsulfonyl)phenyl)-1,2,3,4-tetrahydro-1-naphthalenyl)acetamide;

3-((5R)-5-((((2R,S)-1-((4-methylphenyl)sulfonyl)-3-oxo-2-piperazinyl)acetyl)amino)-5,6,7,8-tetrahydro-2-naphthalenyl)benzoic acid;

2-fluoro-4-((5R)-5-((((2R,S)-1-((4-methylphenyl)sulfonyl)-3-oxo-2-piperazinyl)acetyl)amino)-5,6,7,8-tetrahydro-2-naphthalenyl)benzoic acid;

2-((2R,S)-1-((4-methylphenyl)sulfonyl)-3-oxo-2-piperazinyl)-N-((1R)-6-(3-(((2-methylpropyl)amino)methyl)phenyl)-1,2,3,4-tetrahydro-1-naphthalenyl)acetamide;

2-((2R)-1-((4-methylphenyl)sulfonyl)-3-oxo-2-piperazinyl)-N-((1R)-6-(1-(1-piperidinylmethyl)ethenyl)-1,2,3,4-tetrahydro-1-naphthalenyl)acetamide;

2-((2R)-1-((4-methylphenyl)sulfonyl)-3-oxo-2-piperazinyl)-N-((1R)-6-(1-(1-pyrrolidinylmethyl)ethenyl)-1,2,3,4-tetrahydro-1-naphthalenyl)acetamide;

2-((2R)-1-((4-methylphenyl)sulfonyl)-3-oxo-2-piperazinyl)-N-((1R)-6-((4-methyl-1-piperazinyl)methyl)-1,2,3,4-tetrahydro-1-naphthalenyl)acetamide;

2-((2R,S)-1-((3-methylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((2-methylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((3-chloro-4-fluorophenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((4-chloro-2-methylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((2-chlorophenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-3-oxo-1-(phenylsulfonyl)-2-piperazinyl)-N-((1R)-6-(1-piperidinylmethyl)-1,2,3,4-tetrahydro-1-naphthalenyl)acetamide;

2-((2R)-1-((4-chlorophenyl)sulfonyl)-3-oxo-2-piperazinyl)-N-((1R)-6-(1-piperidinylmethyl)-1,2,3,4-tetrahydro-1-naphthalenyl)acetamide;

2-((2R)-1-((4-chlorophenyl)sulfonyl)-3-oxo-2-piperazinyl)-N-((1R)-6-(((1,1-dimethylethyl)amino)methyl)-1,2,3,4-tetrahydro-1-naphthalenyl)acetamide;

2-((2R)-1-((4-chlorophenyl)sulfonyl)-3-oxo-2-piperazinyl)-N-((1R)-6-(((2,2-dimethylpropyl)amino)methyl)-1,2,3,4-tetrahydro-1-naphthalenyl)acetamide;

2-((2R)-1-((4-chlorophenyl)sulfonyl)-3-oxo-2-piperazinyl)-N-((1R)-6-(((2-methylpropyl)amino)methyl)-1,2,3,4-tetrahydro-1-naphthalenyl)acetamide;

2-((2R)-1-((4-chlorophenyl)sulfonyl)-3-oxo-2-piperazinyl)-N-((1R)-6-((cyclobutylamino)methyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(((2-(1-pyrrolidinyl)ethyl)amino)methyl)-1,2,3,4-tetrahydro-1-naphthalenyl)acetamide;

2-((2R,S) 1-((4-methylphenyl)sulfonyl)-3-oxo-2-piperazinyl)-N-((1R)-6-(4-morpholinylmethyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(((phenylmethyl)amino)methyl)-1,2,3,4-tetrahydro-1-naphthalenyl)acetamide;

2-((2R,S)-1-((4-methylphenyl)sulfonyl)-3-oxo-2-piperazinyl)-N-((1R)-6-(2-(1-piperidinyl)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(1-piperidinylmethyl)-1,2,3,4-tetrahydro-1-naphthalenyl)acetamide;

methyl (2E)-3-((5R)-5-(((((2R,S)-1-((4-methylphenyl)sulfonyl)-3-oxo-2-piperazinyl)acetyl)amino)-5,6,7,8-tetrahydro-2-naphthalenyl)-2-propenoate;

2-((2R,S)-1-((4-chlorophenyl)sulfonyl)-3-oxo-2-piperazinyl)-N-((1R)-6-(4-morpholinylmethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-((4-methyl-1-piperazinyl)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2,2-dimethylpropyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2-methylpropyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((phenylmethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2-phenylethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2-(2-fluorophenyl)ethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-((cyclobutylamino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2-(1-pyrrolidinyl)ethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((3-methylbutyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-((4-fluoro-1-piperidinyl)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((1-naphthalenylmethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(((2-(2-(methyloxy)phenyl)ethyl)amino)methyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(1-piperidinyl)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-((2-methylpropyl)amino)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(((1,1-dimethylethyl)amino)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(((2,2-dimethylpropyl)amino)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(cyclobutylamino)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-((phenylmethyl)amino)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(4-morpholinyl)ethyl)-1,2,3,4-tetrahydro-1-naphthalenyl)acetamide;

2-((2R,S)-1-((4-chlorophenyl)sulfonyl)-3-oxo-2-piperazinyl)-N-((1R)-6-(2-(1-pyrrolidinyl)ethyl)-1,2,3,4-tetrahydro-1-naphthalenyl)acetamide;

2-((2R,S)-1-((4-chlorophenyl)sulfonyl)-3-oxo-2-piperazinyl)-N-((2R)-6-(1-piperidinylmethyl)-1,2,3,4-tetrahydro-2-naphthalenyl)acetamide;

2-((2R,S)-1-((4-chlorophenyl)sulfonyl)-3-oxo-2-piperazinyl)-N-((2R)-6-(2-((2-(1-pyrrolidinyl)ethyl)amino)ethyl)-1,2,3,4-tetrahydro-2-naphthalenyl)acetamide;

2-((2R)-1-((4-methylphenyl)sulfonyl)-3-oxo-2-piperazinyl)-N-((1R)-6-(((2-methylpropyl)amino)methyl)-1,2,3,4-tetrahydro-1-naphthalenyl)acetamide;

2-((2R)-1-((4-methylphenyl)sulfonyl)-3-oxo-2-piperazinyl)-N-((1R)-6-((((1 S)-1-methylpropyl)amino)methyl)-1,2,3,4-tetrahydro-1-naphthalenyl)acetamide;

2-((2R)-1-((4-methylphenyl)sulfonyl)-3-oxo-2-piperazinyl)-N-((1R)-6-(((2-(1-pyrrolidinyl)ethyl)amino)methyl)-1,2,3,4-tetrahydro-1-naphthalenyl)acetamide;

2-((2R)-1-((4-methylphenyl)sulfonyl)-3-oxo-2-piperazinyl)-N-((1R)-6-(2-(1-piperidinyl)ethyl)-1,2,3,4-tetrahydro-1-naphthalenyl)acetamide;

2-((2R)-1-((4-chlorophenyl)sulfonyl)-3-oxo-2-piperazinyl)-N-((1R)-6-(2-(1-piperidinyl)ethyl)-1,2,3,4-tetrahydro-1-naphthalenyl)acetamide;

2-((2R)-1-((4-methylphenyl)sulfonyl)-3-oxo-2-piperazinyl)-N-((1R)-6-(4-morpholinylmethyl)-1,2,3,4-tetrahydro-1-naphthalenyl)acetamide;

N-((1R)-6-((1R,S)-1-(cyclopentylamino)ethyl)-1,2,3,4-tetrahydro-1-naphthalenyl)-2-((2R)-1-((4-methylphenyl)sulfonyl)-3-oxo-2-piperazinyl)acetamide;

N-((1R)-6-(((1,1-dimethylethyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((2,2-dimethylpropyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-((4-fluoro-1-piperidinyl)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(3-cyanophenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-(bis(2-methylpropyl)amino)propyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-((cyclopentylmethyl)amino)propyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-aminopropyl)-1,2,3,4-tetrahydro-1-naphthalenyl)-2-((2R,S)-1-((4-chloro-2,5-dimethylphenyl)sulfonyl)-3-oxo-2-piperazinyl)acetamide;

N-((1R)-6-(3-aminopropyl)-1,2,3,4-tetrahydro-1-naphthalenyl)-2-((2R)-1-((4-methylphenyl)sulfonyl)-3-oxo-2-piperazinyl)acetamide;

N-((1R)-6-(3-(bis(2-methylpropyl)amino)propyl)-1,2,3,4-tetrahydro-1-naphthalenyl)-2-((2R)-1-((4-methylphenyl)sulfonyl)-3-oxo-2-piperazinyl)acetamide;

N-((1R)-6-(((1,1-dimethylethyl)amino)methyl)-1,2,3,4-tetrahydro-1-naphthalenyl)-2-((2R,S)-3-oxo-1-((4-((trifluoromethyl)oxy)phenyl)sulfonyl)-2-piperazinyl)acetamide;

N-((1R)-6-(((2-methylpropyl)amino)methyl)-1,2,3,4-tetrahydro-1-naphthalenyl)-2-((2R,S)-3-oxo-1-((4-((trifluoromethyl)oxy)phenyl)sulfonyl)-2-piperazinyl)acetamide;

N-((1R)-6-(((cyclopropylmethyl)amino)methyl)-1,2,3,4-tetrahydro-1-naphthalenyl)-2-((2R,S)-3-oxo-1-((4-((trifluoromethyl)oxy)phenyl)sulfonyl)-2-piperazinyl)acetamide;

N-((1R)-6-(((1-methylethyl)amino)methyl)-1,2,3,4-tetrahydro-1-naphthalenyl)-2-((2R,S)-3-oxo-1-((4-((trifluoromethyl)oxy)phenyl)sulfonyl)-2-piperazinyl)acetamide;

N-((1R)-6-((cyclobutylamino)methyl)-1,2,3,4-tetrahydro-1-naphthalenyl)-2-((2R,S)-3-oxo-1-((4-((trifluoromethyl)oxy)phenyl)sulfonyl)-2-piperazinyl)acetamide;

N-((1R)-6-(1-(((1,1-dimethylethyl)amino)methyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(1-(((cyclopropylmethyl)amino)methyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(1-((cyclobutylamino)methyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(1-(1-azetidinylmethyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(1-((4-fluoro-1-piperidinyl)methyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-(acetylamino)phenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-(hydroxymethyl)phenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-((cyclobutylamino)methyl)phenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(3-((cyclopentylamino)methyl)phenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(1-(((2,2-dimethylpropyl)amino)methyl)ethenyl)-1,2,3,4-tetrahydro-1-naphthalenyl)-2-((2R,S)-1-((4-methylphenyl)sulfonyl)-3-oxo-2-piperazinyl)acetamide;

N-((1R)-6-((4-fluoro-1-piperidinyl)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((3-methylbutyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((3,3-dimethylbutyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((cyclohexylmethyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((2-(2-fluorophenyl)ethyl)amino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((1,1-dimethylethyl)amino)methyl)-1,2,3,4-tetrahydro-1-naphthalenyl)-2-((2S)-1-((4-methylphenyl)sulfonyl)-3-oxo-2-piperazinyl)acetamide;

N-((1R)-6-(((1,1-dimethylethyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(((2,2-dimethylpropyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-((cyclopentylamino)methyl)-1,2,3,4-tetrahydro-1-naphthalenyl)-2-((2R,S)-1-((4-methylphenyl)sulfonyl)-3-oxo-2-piperazinyl)acetamide;

N-((1R)-6-(((3-methylbutyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(((cyclohexylmethyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-((cyclohexylamino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(((cyclopropylmethyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-((cyclopentylamino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-((cyclopropylamino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(1-azepanylmethyl)-1,2,3,4-tetrahydro-1-naphthalenyl)-2-((2R)-1-((4-methylphenyl)sulfonyl)-3-oxo-2-piperazinyl)acetamide;

N-((1R)-6-(((3R,S)-3-hydroxy-1-piperidinyl)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(((2-(methyloxy)ethyl)amino)methyl)-1,2,3,4-tetrahydro-1-naphthalenyl)-2-((2R)-1-((4-methylphenyl)sulfonyl)-3-oxo-2-piperazinyl)acetamide;

N-((1R)-6-(((2-hydroxyethyl)amino)methyl)-1,2,3,4-tetrahydro-1-naphthalenyl)-2-((2R)-1-((4-methylphenyl)sulfonyl)-3-oxo-2-piperazinyl)acetamide;

2-((2R,S)-1-((4-chloro-2,5-dimethylphenyl)sulfonyl)-3-oxo-2-piperazinyl)-N-((1R)-6-((cyclopentylamino)methyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-((4-methyl-1-piperazinyl)methyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-((tetrahydro-2H-pyran4-ylamino)methyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-(((cyclopropylmethyl)amino)methyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-(3-((4-pyridinylmethyl)amino)propyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-(3-((tetrahydro-2H-pyran-4-ylmethyl)amino)propyl)-1,2,3,4-tetrahydro-1-naphthalenyl)acetamide;

2-((2R,S)-1-((4-chloro-2,5-dimethylphenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((3,4-dichlorophenyl)sulfonyl)-5,5-dimethyl-3-oxo-2-piperazinyl)-N-((1R)-6-(((1,1-dimethylethyl)amino)methyl)-1,2,3,4-tetrahydro-1-naphthalenyl)acetamide;

1,1-dimethylethyl 4-((5R)-5-(((((2R,S)-1-((4-methylphenyl)sulfonyl)-3-oxo-2-piperazinyl)acetyl)amino)-5,6,7,8-tetrahydro-2-naphthalenyl)-3,6-dihydro-1(2H)-pyridinecarboxylate;

2-((2R,S)-1-((4-(1,1-dimethylethyl)phenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((2,5-dichlorophenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((3,4-dichlorophenyl)sulfonyl)-5-oxo-2-piperazinyl)-N-((1R)-6-(1-piperidinylmethyl)-1,2,3,4-tetrahydro-1-naphthalenyl)acetamide;

2-((2R,S)-1-((3,4-dichlorophenyl)sulfonyl)-3-oxo-2-piperazinyl)-N-((1R)-1,2,3,4-tetrahydro-1-naphthalenyl)acetamide;

2-((2R,S)-1-((3,4-dichlorophenyl)sulfonyl)-3-oxo-2-piperazinyl)-N-((1R)-6-(((1,1-dimethylethyl)amino)methyl)-1,2,3,4-tetrahydro-1-naphthalenyl)acetamide;

2-((2R,S)-1-((3,4-dichlorophenyl)sulfonyl)-3-oxo-2-piperazinyl)-N-((1R)-6-(1-piperidinylmethyl)-1,2,3,4-tetrahydro-1-naphthalenyl)acetamide;

2-((2R,S)-1-((3,4-dichlorophenyl)sulfonyl)-3-oxo-2-piperazinyl)-N-((1R)-6-((4-fluoro-1-piperidinyl)methyl)-1,2,3,4-tetrahydro-1-naphthalenyl)acetamide;

2-((2R,S)-1-((3,4-dichlorophenyl)sulfonyl)-3-oxo-2-piperazinyl)-N-((1R)-6-(1-pyrrolidinylmethyl)-1,2,3,4-tetrahydro-1-naphthalenyl)acetamide;

2-((2R,S)-1-((3,4-dichlorophenyl)sulfonyl)-3-oxo-2-piperazinyl)-N-((1R)-6-(((2-methylpropyl)amino)methyl)-1,2,3,4-tetrahydro-1-naphthalenyl)acetamide;

2-((2R,S)-1R-((3,5-dibromo-4-methylphenyl)sulfonyl)-3-oxo-2-piperazinyl)-N-((1R)-6-(((1,1-dimethylethyl)amino)methyl)-1,2,3,4-tetrahydro-1-naphthalenyl)acetamide;

2-((2R)-1-((3,5-dibromo-4-methylphenyl)sulfonyl)-3-oxo-2-piperazinyl)-N-((1R)-6-(((2,2-dimethylpropyl)amino)methyl)-1,2,3,4-tetrahydro-1-naphthalenyl)acetamide;

2-((2S)-1-((3,5-dibromo-4-methylphenyl)sulfonyl)-3-oxo-2-piperazinyl)-N-((1R)-6-(((1,1-dimethylethyl)amino)methyl)-1,2,3,4-tetrahydro-1-naphthalenyl)acetamide;

N-((1R)-6-(1-(cyclopropylmethyl)-1,2,3,6-tetrahydro-4-pyridinyl)-1,2,3,4-tetrahydro-1-naphthalenyl)-2-((2R,S)-1-((4-methylphenyl)sulfonyl)-3-oxo-2-piperazinyl)acetamide; and N-((1R)-6-(1-(cyclohexylmethyl)-1,2,3,6-tetrahydro-4-pyridinyl)-1,2,3,4-tetrahydro-1-naphthalenyl)-2-((2R,S)-1-((4-methylphenyl)sulfonyl)-3-oxo-2-piperazinyl)acetamide.

39. A compound selected from the group consisting of:

2-((R)-3-oxo-1-tosylpiperazin-2-yl)-N-((R)-6-(3-(piperidin1-yl)prop-1-en-2-yl)-1,2,3,4-tetrahydronaphthalen-1-yl)acetamide;

N-((R)-6-((4-fluoropiperidin-1-yl)methyl)-1,2,3,4-tetrahydronaphthalen-1-yl)-2-((R)-3-oxo-1-tosylpiperazin-2-yl)acetamide;

N-((R)-6-((neopentylamino)methyl)-1,2,3,4-tetrahydronaphthalen-1-yl)-2-((R)-3-oxo-1-tosylpiperazin-2-yl)acetamide;

N-((R)-6-(azepan-1-ylmethyl)-1,2,3,4-tetrahydronaphthalen-1-yl)-2-((R)-3-oxo-1-(phenylsulfonyl)piperazin-2-yl)acetamide;

2-((R)-1-(4-chlorophenylsulfonyl)3-oxopiperazin-2-N-(R)-6-(piperidin-1-ylmethyl)-1,2,3,4-tetrahydronaphthalen-1-yl)acetamide; and N-methyl-2-((R)-3-oxo-1-tosylpiperazin-2-yl)-N-((R)-6-(piperidin-1-ylmethyl)-1,2,3,4-tetrahydronaphthalen-1-yl)acetamide; or a pharmaceutically acceptable salt thereof.

40. A pharmaceutical composition comprising a pharmaceutically acceptable carrier and a compound according to claim 1.

41. A pharmaceutical composition for the treatment of disease conditions mediated by bradykinin consisting of pain and inflammation, in a mammalian subject, which comprises a therapeutically effective amount of a compound according to claim 1 and a pharmaceutically acceptable carrier.

42. A pharmaceutical composition comprising a pharmaceutically acceptable carrier and a compound according to claim 39.

* * * * *

UNITED STATES PATENT AND TRADEMARK OFFICE
CERTIFICATE OF CORRECTION

PATENT NO. : 7,393,852 B2
APPLICATION NO. : 10/874086
DATED : July 1, 2008
INVENTOR(S) : Jian J. Chen et al.

It is certified that error appears in the above-identified patent and that said Letters Patent is hereby corrected as shown below:

Column 145, line 61, after "alkyl" insert --, or substituted $C_{1-4}$alkyl;--.

Column 146, line 22, delete "thereto" and insert --thereof--; line 63, delete "5-7" and insert --5-8--.

Column 147, line 23, delete "claim 8" and insert --claim 7--; lines 42 and 46, delete "4-hydroxypiperidin-1-methyl" and insert --4-hydroxypiperidin-1-ylmethyl--.

Column 149, line 24, delete "$(C_1-C_4)$alkoxy$(C_1-C_4)$alkyl, $(C_2-C_4)$alkenyl," and insert --$(C_1-C_4)$alkoxy$(C_1-C_4)$alkyl, $(C_1-C_4)$alkyl, $(C_2-C_4)$alkenyl,--.

Column 151, lines 42-44, delete "1-ylmethyl, piperazin-1-ylmethyl, azocan-1-ylmethyl, azepan-1-ylmethyl, (7azabicyclo".

Column 152, lines 12 and 47, delete "(1,3,3-trimethyl-6-azaicyclo[3.2.1]oct-6yl)methyl" and insert --(1,3,3-trimethyl-6-azaicyclo[3.2.1]oct-6-yl)methyl--.

Column 153, line 33, delete "$C(O)^{8}$" and insert --$C(O)R^8$--; line 38, delete "oxo,".

Column 154, lines 3 and 4, delete "di-$C_{1-4-alkylamino}$ hd 2-4-alkenyl" and insert --di-$C_{1-4}$-alkylamino-$C_{2-4}$-alkenyl--; line 33, delete "mono-$CC_{1-4}$-alkylamino-$C_{1-4}$-alkyl" and insert -- mono-$C_{1-4}$-alkylamino-$C_{1-4}$-alkyl--; line 63, delete "piperidin-1-methyl" and insert --piperidin-1-ylmethyl--.

Column 159, delete lines 19-38.

Column 162, line 4, delete "2-((2R,S)-1R-((4-methylphenyl)" and insert --2-((2R,S)-1-((4-methylphenyl)--.

Signed and Sealed this

Twenty-fifth Day of May, 2010

David J. Kappos
*Director of the United States Patent and Trademark Office*